(12) United States Patent
Akino et al.

(10) Patent No.: US 8,592,544 B2
(45) Date of Patent: *Nov. 26, 2013

(54) POLYMERIC COMPOUND CONTAINING METAL COMPLEX RESIDUE AND ELEMENT COMPRISING SAME

(75) Inventors: Nobuhiko Akino, Tsukuba (JP); Rei Okamura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 305 days.

This patent is subject to a terminal disclaimer.

(21) Appl. No.: 13/000,984

(22) PCT Filed: Jun. 23, 2009

(86) PCT No.: PCT/JP2009/061361
§ 371 (c)(1),
(2), (4) Date: Dec. 22, 2010

(87) PCT Pub. No.: WO2009/157424
PCT Pub. Date: Dec. 30, 2009

(65) Prior Publication Data
US 2011/0124808 A1 May 26, 2011

(30) Foreign Application Priority Data
Jun. 23, 2008 (JP) ................................. 2008-163038

(51) Int. Cl.
*C08G 79/00* (2006.01)

(52) U.S. Cl.
USPC .......................................................... 528/9

(58) Field of Classification Search
USPC .......................................................... 528/9
See application file for complete search history.

(56) References Cited

U.S. PATENT DOCUMENTS

| | | | |
|---|---|---|---|
| 6,303,238 B1 * | 10/2001 | Thompson et al. | 428/690 |
| 6,821,645 B2 * | 11/2004 | Igarashi et al. | 428/690 |
| 7,691,493 B2 * | 4/2010 | Kamatani et al. | 428/690 |
| 7,767,777 B2 * | 8/2010 | Buesing et al. | 528/9 |
| 7,820,305 B2 * | 10/2010 | Schulte et al. | 428/690 |
| 8,008,418 B2 * | 8/2011 | Morishita et al. | 528/9 |
| 8,206,838 B2 * | 6/2012 | Marrocco et al. | 428/690 |
| 2002/0193532 A1 | 12/2002 | Ikehira et al. | |
| 2003/0068536 A1 * | 4/2003 | Tsuboyama et al. | 428/704 |
| 2003/0091862 A1 | 5/2003 | Tokito et al. | |
| 2004/0072018 A1 | 4/2004 | Herron et al. | |
| 2004/0091739 A1 | 5/2004 | Eriyama et al. | |
| 2004/0121184 A1 * | 6/2004 | Thompson et al. | 428/690 |
| 2004/0138455 A1 | 7/2004 | Stossel et al. | |
| 2005/0037233 A1 * | 2/2005 | Dobbs et al. | 428/690 |
| 2005/0147843 A1 | 7/2005 | Kobayashi et al. | |
| 2005/0165235 A1 * | 7/2005 | Grushin et al. | 546/2 |
| 2006/0063026 A1 | 3/2006 | Holmes et al. | |
| 2006/0093852 A1 * | 5/2006 | Marsitzky et al. | 428/690 |
| 2007/0043001 A1 | 2/2007 | Bilobeau et al. | |
| 2008/0114151 A1 * | 5/2008 | Shirasawa et al. | 528/395 |
| 2008/0248220 A1 * | 10/2008 | Sekine et al. | 428/1.4 |
| 2008/0290792 A1 * | 11/2008 | Takeuchi et al. | 313/504 |
| 2008/0312396 A1 * | 12/2008 | Stoessel et al. | 528/9 |
| 2009/0048415 A1 * | 2/2009 | Buesing et al. | 528/9 |
| 2009/0206326 A1 * | 8/2009 | Grushin et al. | 257/40 |
| 2010/0019669 A1 * | 1/2010 | Akino et al. | 313/504 |
| 2010/0038592 A1 * | 2/2010 | Akino et al. | 252/301.35 |
| 2010/0264812 A1 * | 10/2010 | Akino et al. | 313/504 |
| 2010/0283038 A1 * | 11/2010 | Sekine et al. | 257/40 |
| 2010/0331506 A1 * | 12/2010 | Fortte et al. | 526/241 |
| 2011/0227050 A1 * | 9/2011 | Kobayashi et al. | 257/40 |
| 2012/0205585 A1 * | 8/2012 | Okamura et al. | 252/301.35 |

FOREIGN PATENT DOCUMENTS

| | | |
|---|---|---|
| EP | 1932851 A1 | 6/2008 |
| EP | 2128168 A1 | 12/2009 |
| JP | 6-009960 A | 1/1994 |
| JP | 2003-073479 A | 3/2003 |
| JP | 2003-253258 A | 9/2003 |
| JP | 2005-524725 A | 11/2003 |
| JP | 2003-342325 A | 12/2003 |
| JP | 2004-002755 A | 1/2004 |
| JP | 2004-531485 A | 10/2004 |
| JP | 2005-528508 A | 9/2005 |
| JP | 2006-503126 A1 | 1/2006 |
| JP | 2006-524696 T | 11/2006 |
| JP | 2007-277558 A | 10/2007 |
| WO | WO 2007020952 A1 * | 2/2007 |

OTHER PUBLICATIONS

European Patent Office, "Communication with Extended European Search Report," issued in connection with European Patent Application No. 09770134.6, dated Apr. 5, 2013.
State Intellectual Property Office of People's Republic of China, "First Office Action," issued in connection with Chinese Patent Application No. 200980124003.3, dated Jan. 14, 2013.

* cited by examiner

*Primary Examiner* — Liam Heincer
(74) *Attorney, Agent, or Firm* — Sughrue Mion, PLLC

(57) ABSTRACT

A polymeric compound containing a residue of a metal complex represented by formula (1) [wherein M represents a metal atom selected from ruthenium, rhodium, palladium, osmium, iridium and platinum; $R^1$, $R^2$, $R^3$, $R^4$, $R^5$, $R^6$ and $R^8$ independently represent a hydrogen atom, a halogen atom, an alkyl group, or the like; m represents an integer of 1 to 3; n represents an integer of 0 to 2; $Z^1$, $Z^2$, $Z^3$, $Z^4$ and $Z^5$ independently represent a carbon atom or a nitrogen atom, provided that at least two member of $Z^1$, $Z^2$, $Z^3$, $Z^4$ and $Z^5$ represent a nitrogen atom, and when any one member of $Z^1$, $Z^2$, $Z^3$, $Z^4$ and $Z^5$ represents a carbon atom, a hydrogen atom bound to the carbon atom may be substituted by a substituent; a moiety represented by formula (2) represents a bidentate monoanionic ligand; and Rx and Ry are atoms bound to the metal atom M and independently represent a carbon atom, an oxygen atom or a nitrogen atom] and a bivalent group.

15 Claims, No Drawings

POLYMERIC COMPOUND CONTAINING METAL COMPLEX RESIDUE AND ELEMENT COMPRISING SAME

CROSS REFERENCE TO RELATED APPLICATIONS

This application is a National Stage of International Application No. PCT/JP2009/061361 filed Jun. 23, 2009, claiming priority based on Japanese Patent Application No. 2008-163038 filed Jun. 23, 2008, the contents of all of which are incorporated herein by reference in their entirety.

TECHNICAL FIELD

The present invention relates to a polymer compound containing a metal complex residue and a device comprising these.

BACKGROUND ART

Various metal complexes have been used as light-emitting materials used for a light-emitting layer of electroluminescent devices. Moreover, light-emitting materials using the structure of a metal complex as a repeating unit of a polymer have also been proposed. For example, a polymer compound having a structure of an orthometalated complex having iridium as a central metal, (Ir(ppy)$_3$: a tris(orthometalated)iridium(III) complex having a 2-phenylpyridine as a ligand) and a fluorenediyl group as a repeating unit is proposed (PATENT DOCUMENT 1).

CITATION LIST

Patent Document

Patent Document 1: JP 2003-73479 A

SUMMARY OF THE INVENTION

Problems to be Solved by the Invention

However, in the case where the polymer compound is used for production of an electroluminescent device and the like, a device having excellent luminous efficiency is not obtained.

Then, an object of the present invention is to provide a polymer compound and the like in which a device having excellent luminous efficiency is obtained in the case where the polymer compound is used for production of an electroluminescent device and the like.

Means for Solving the Problems

Firstly, the present invention provides a polymer compound containing:

a residue of a metal complex represented by the following formula (1):

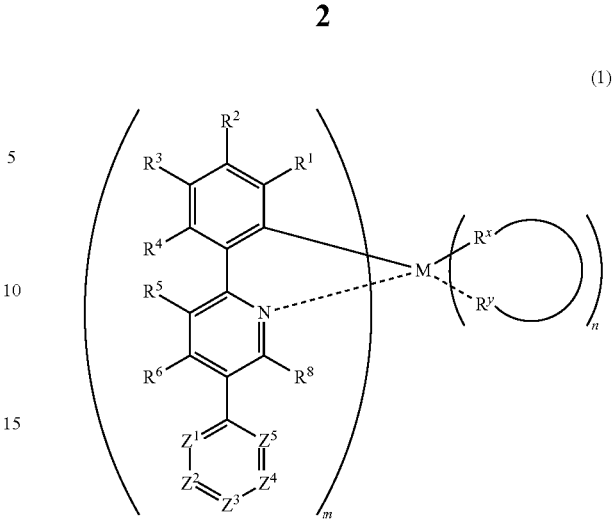

(wherein M represents a metal atom of ruthenium, rhodium, palladium, osmium, iridium, or platinum; $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group, or $R^1$ and $R^2$, $R^2$ and $R^3$, $R^3$ and $R^4$, $R^4$ and $R^5$, or $R^5$ and $R^6$ may be bonded to form a ring; m is an integer of 1 to 3 and n is an integer of 0 to 2; in the case where each of $R^1$, $R^2$, $R^3$, $R^4$, $R^5$, $R^6$, and $R^8$ is plural, a plurality of $R^1$ may be the same or different, a plurality of $R^2$ may be the same or different, a plurality of $R^3$ may be the same or different, a plurality of $R^4$ may be the same or different, a plurality of $R^5$ may be the same or different, a plurality of $R^6$ may be the same or different, and a plurality of $R^8$ may be the same or different; $Z^1$, $Z^2$, $Z^3$, $Z^4$, and $Z^5$ each independently represent a carbon atom or a nitrogen atom; in the case where each of $Z^1$, $Z^2$, $Z^3$, $Z^4$, and $Z^5$ is plural, a plurality of $Z^1$ may be the same or different, a plurality of $Z^2$ may be the same or different, a plurality of $Z^3$ may be the same or different, a plurality of $Z^4$ may be the same or different, a plurality of $Z^5$ may be the same or different, wherein at least two of $Z^1$, $Z^2$, $Z^3$, $Z^4$, and $Z^5$ are nitrogen atoms; in the case where one of $Z^1$, $Z^2$, $Z^3$, $Z^4$, and $Z^5$ is a carbon atom, a hydrogen atom bonded to the carbon atom may be replaced by a substituent; a portion represented by the following formula (2):

represents a monoanionic bidentate ligand, wherein $R^x$ and $R^y$ are an atom bonded to the metal atom M, and each independently represent a carbon atom, an oxygen atom, or a nitrogen atom; in the case where a plurality of monoanionic bidentate ligands exist, the monoanionic bidentate ligands may be the same or different.); and a divalent group represented by the following formula (3-1), (3-2), (3-3), (3-4), or (3-5):

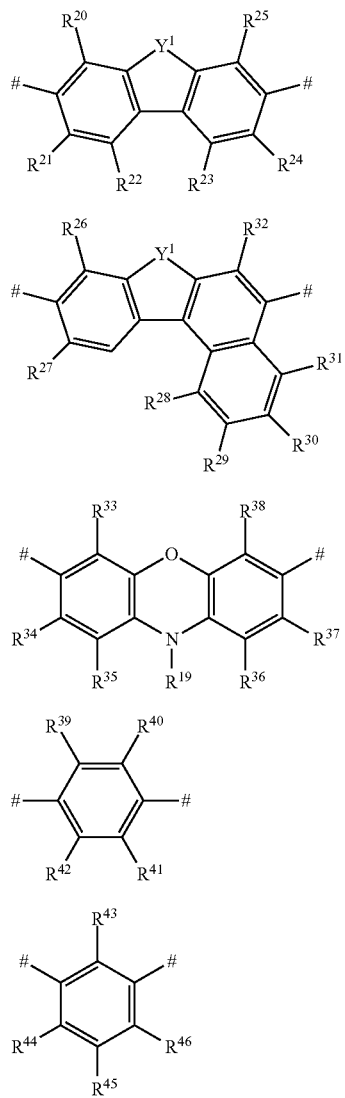

(wherein # represents a bond; $Y^1$ represents $-C(R^9)(R^{10})-$, $-O-C(R^{17})(R^{18})-$, $-O-$, $-S-$, $-B(R^{11})-$, $-Si(R^{12})(R^{13})-$, $-P(R^{14})-$, $-P(R^{15})(=O)-$, or $-N(R^{16})-$; $R^9$, $R^{10}$, $R^{11}$, $R^{12}$, $R^{13}$, $R^{14}$, $R^{15}$, $R^{16}$, $R^{17}$, $R^{18}$, and $R^{19}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group.)

Secondly, the present invention provides a composition, a film, and a device that contain the polymer compound.

Thirdly, the present invention provides a surface light source and lighting using the device.

Fourthly, the present invention provides a method for producing a polymer compound containing the residue of a metal complex represented by the formula (1) and the divalent group represented by the formula (3-1), (3-2), (3-3), (3-4), or (3-5), including the method of reacting a metal complex represented by the following formula (5):

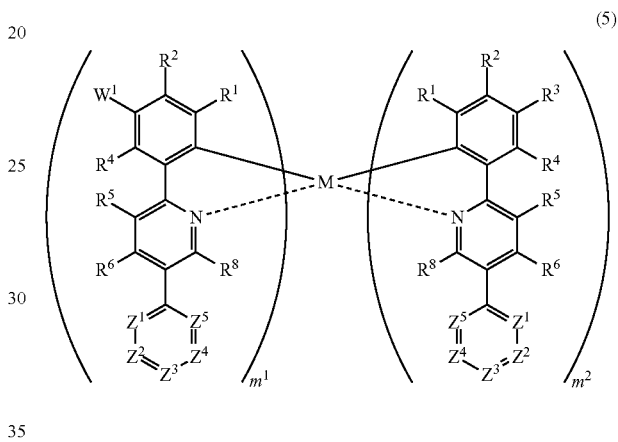

(wherein $W^1$ represents a polymerization reactive group; $m^1$ is an integer of 1 to 3, and $m^2$ is an integer of 0 to 2; in the case where a plurality of $W^1$ exists, the plurality of $W^1$ may be the same or different; M represents a metal atom of ruthenium, rhodium, palladium, osmium, iridium, or platinum; $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or $R^1$ and $R^2$, $R^2$ and $R^3$, $R^3$ and $R^4$, $R^4$ and $R^5$, or $R^5$ and $R^6$ may be bonded to form a ring; $Z^1$, $Z^2$, $Z^3$, $Z^4$, and $Z^5$ each independently represent a carbon atom or a nitrogen atom; in the case where each of $Z^1$, $Z^2$, $Z^3$, $Z^4$, and $Z^5$ is plural, a plurality of $Z^1$ may be the same or different, a plurality of $Z^2$ may be the same or different, a plurality of $Z^3$ may be the same or different, a plurality of $Z^4$ may be the same or different, a plurality of $Z^5$ may be the same or different, wherein at least two of $Z^1$, $Z^2$, $Z^3$, $Z^4$, and $Z^5$ are nitrogen atoms; in the case where one of $Z^1$, $Z^2$, $Z^3$, $Z^4$, and $Z^5$ is a carbon atom, a hydrogen atom bonded to the carbon atom may be replaced by a substituent.) with a compound represented by the following formula (6-1), (6-2), (6-3), (6-4), or (6-5):

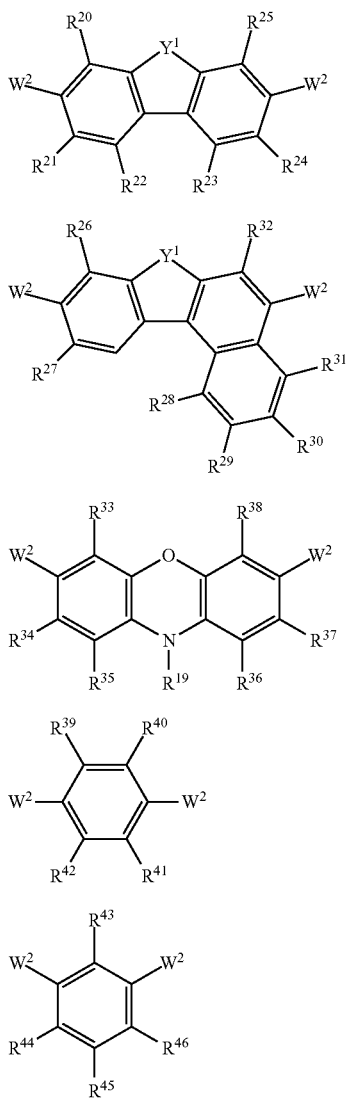

(6-1)
(6-2)
(6-3)
(6-4)
(6-5)

(wherein $W^2$ represents a polymerization reactive group; a plurality of $W^2$ may be the same or different; $Y^1$ represents —C($R^9$)($R^{10}$)—, —O—C($R^{17}$)($R^{18}$)—, —O—, —S—, —B($R^{11}$)—, —Si($R^{12}$)($R^{13}$)—, —P($R^{14}$)—, —P($R^{15}$) (=O)—, or —N($R^{16}$)—; $R^9$, $R^{10}$, $R^{11}$, $R^{12}$, $R^{13}$, $R^{14}$, $R^{15}$, $R^{16}$, $R^{17}$, $R^{18}$, and $R^{19}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group.)

Fifthly, the present invention provides a compound represented by the following formula (11a) or (11b):

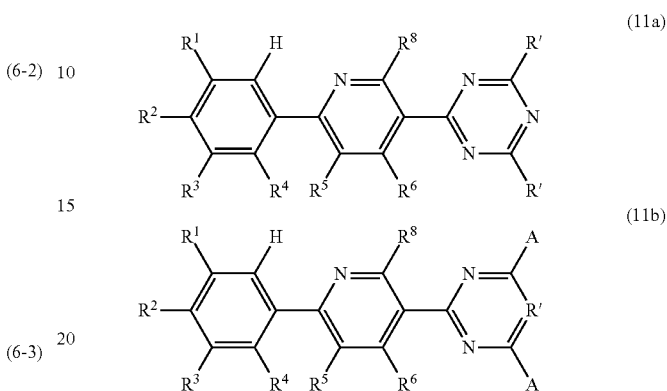

(11a)
(11b)

(wherein $R^1$, $R^2$, $R^3$, $R^4$, $R^5$, $R^6$, $R^8$, and R' are as defined above; A represents an aryl group or a monovalent heterocyclic group; a plurality of R' may be the same or different, and a plurality of A may be the same or different.)

Sixthly, the present invention provides a compound represented by the following formula (12):

$$W^3-Ar'-W^3 \quad (12)$$

(wherein $W^3$ represents a polymerization reactive group; a plurality of $W^3$ may be the same or different; Ar' represents a divalent aromatic group having a group represented by 1 to 4 -L-$M^3$, or a divalent heterocyclic group having an atom selected from the group consisting of an oxygen atom, a silicon atom, a phosphorus atom, a boron atom, and a sulfur atom, and a group represented by 1 to 4 -L-$M^3$; L represents a single bond, —O—, —S—, —C(=O)—, —C(=O)O—, —S(=O)—, —S(=O)$_2$—, —Si($R^{68}$)($R^{69}$)—, N($R^{70}$)—, —B($R^{71}$)—, —P($R^{72}$)—, —P(=O)($R^{73}$)—, an alkylene group that may be substituted, an alkenylene group that may be substituted, an alkynylene group that may be substituted, an arylene group that may be substituted, or a divalent heterocyclic group that may be substituted; $M^3$ represents a monovalent residue of a metal complex represented by the formula (1); in the case where a plurality of L and a plurality of $M^3$ exist, the plurality of L may be the same or different and the plurality of $M^3$ may be the same or different; $R^{68}$, $R^{69}$, $R^{70}$, $R^{71}$, $R^{72}$, and $R^{73}$ each independently represent a hydrogen atom, an alkyl group, an aryl group, a monovalent heterocyclic group, or a cyano group.)

Advantages of the Invention

In the case where the polymer compound and the like according to the present invention are used for production of an electroluminescent device and the like, an electroluminescent device and the like having excellent luminous efficiency are obtained. Additionally, an effect of low driver voltage is attained in a preferable embodiment. Accordingly, the polymer compound and the like according to the present invention are particularly useful for production of devices such as light-emitting devices (for example, electroluminescent devices) and photoelectric devices.

MODE FOR CARRYING OUT THE INVENTION

Hereinafter, the present invention will be described in detail. In the structural formulas herein, a bond shown by a dashed line represents a coordinate bond.

<Polymer Compound>

First, a polymer compound according to the present invention will be described.

The polymer compound according to the present invention is a polymer compound containing a residue of a metal complex represented by the formula (1) and a divalent group represented by the formula (3-1), (3-2), (3-3), (3-4), or (3-5). A polymer compound containing the residue of the metal complex represented by the formula (1) and a group represented by the formula (3-1) is preferable. From the viewpoint of solubility, conductivity, and easiness of synthesis of the polymer compound, in the polymer compound according to the present invention, the divalent group represented by the formula (3-1), (3-2), (3-3), (3-4), or (3-5) and the group represented by the formula (4) described later are preferably contained as a repeating unit. Further, from the viewpoint of easiness to synthesize the polymer compound and luminous efficiency when the polymer compound is used for a light-emitting device, the residue of the metal complex represented by the formula (1) is preferably contained in a repeating unit.

In the polymer compound according to the present invention, from the viewpoint of high luminous efficiency, luminescent color and conductivity, a weight ratio of "residue of a metal complex represented by the formula (1)":"divalent group represented by the formula (3-1), (3-2), (3-3), (3-4), or (3-5)" is preferably 1:2 to 1:1000, and more preferably 1:3 to 1:400.

In the polymer compound according to the present invention, from the viewpoint of high luminous efficiency, the proportion of the residue of the metal complex represented by the formula (1) is preferably 0.01 to 50% by weight based on the polymer compound of the present invention, and more preferably 0.01 to 25% by weight.

In the polymer compound according to the present invention, from the viewpoint of conductivity, the proportion of the divalent group represented by the formula (3-1), (3-2), (3-3), (3-4), or (3-5) is preferably 10 to 99.99% by weight based on the polymer compound of the present invention, and more preferably 50 to 99.99% by weight.

In the polymer compound according to the present invention, in the case where the metal complex represented by the formula (1) is contained in a repeating unit, the proportion of the repeating unit containing the residue of the metal complex represented by the formula (1) is preferably 0.01 to 50% by weight based on the polymer compound of the present invention from the viewpoint of easiness to synthesize the polymer compound and high luminous efficiency, more preferably 0.01 to 30% by weight, and particularly preferably 0.01 to 25% by weight.

In the polymer compound according to the present invention, in the case where the divalent group represented by the formula (3-1), (3-2), (3-3), (3-4), or (3-5) is contained as a repeating unit, the proportion of the repeating unit is preferably 10 to 99.99% by weight of the polymer compound of the present invention from the viewpoint of easiness to synthesis and conductivity, more preferably 30 to 99.99% by weight, and particularly preferably 50 to 99.99% by weight.

In the polymer compound according to the present invention, only one or two or more residues of the metal complex represented by the formula (1) and only one or two or more divalent groups represented by the formula (3-1), (3-2), (3-3), (3-4), or (3-5) may be contained.

The polymer compound according to the present invention may be a non-conjugated polymer or may be a conjugated polymer, and a conjugated polymer is preferable from the viewpoint of conductivity. The conjugated polymers mean a polymer compound in which 80 to 100%, particularly 85 to 100%, and specially 90 to 100% of all the bonds in the main chain is conjugated. Conjugated polymers containing an aromatic ring in the main chain are preferable.

In the polymer compound according to the present invention, the polystyrene equivalent number average molecular weight is preferably $1 \times 10^3$ to $1 \times 10^8$ from the viewpoint of device characteristics such as luminous efficiency and life span when the polymer compound is used for a light-emitting device, and more preferably $1 \times 10^4$ to $1 \times 10^7$.

—Metal Complex—

Herein, the residue of the metal complex means an atomic group (k-valent group) that remains by removing k hydrogen atoms (k is an integer of not less than 1) from the metal complex. For example, the residue of the metal complex represented by the formula (1) means an atomic group (group of k value) that remains by removing k hydrogen atoms from the metal complex represented by the formula (1), and the atomic group is preferably a monovalent to trivalent group (namely, k is an integer of 1 to 3).

The metal complex represented by the formula (1) is composed of a metal atom represented by M, a ligand whose number is defined by a suffix m (hereinafter, referred to as a "bidentate chelating ligand" in some cases), and a monoanionic bidentate ligand that is represented by the formula (2) and whose number is defined by a suffix n (hereinafter, referred to as a "monoanionic bidentate ligand"). In the case where only a "ligand" is referred to below, it means both ligands of the bidentate chelating ligand and the monoanionic bidentate ligand.

m is an integer of 1 to 3 in the formula (1).

In the formula (1), n is an integer of 0 to 2, preferably 0 or 1, and more preferably 0.

However, m+n is the total number of ligands that can be bonded to the central metal M. For example, in the case where the central metal is iridium, m=1 and n=2, m=2 and n=1, or m=3 and n=0; preferably, m=3 and n=0, or m=2 and n=1; and more preferably m=3 and n=0.

In the formula (1), at least two of $Z^1$, $Z^2$, $Z^3$, $Z^4$, and $Z^5$ are nitrogen atoms, and preferably two or three thereof are nitrogen atoms. As the metal complex represented by the formula (1), a metal complex having a combination in which these plural nitrogen atoms are not adjacent to each other (namely, these plural nitrogen atoms do not exist in adjacent sites) is particularly preferable. Specifically, the metal complex represented by the formula (1) is a metal complex in which two or three of $Z^1$, $Z^2$, $Z^3$, $Z^4$, and $Z^5$ are nitrogen atoms, and the nitrogen atoms are not adjacent to each other. In the case where one of $Z^1$, $Z^2$, $Z^3$, $Z^4$, and $Z^5$ is a carbon atom, a hydrogen atom bonded to the carbon atom may be replaced by a substituent.

From the viewpoint of stability of the metal complex, easiness of synthesis, and luminous efficiency, the metal complex represented by the formula (1) is preferably a metal complex represented by the following formula (1a) or (1b):

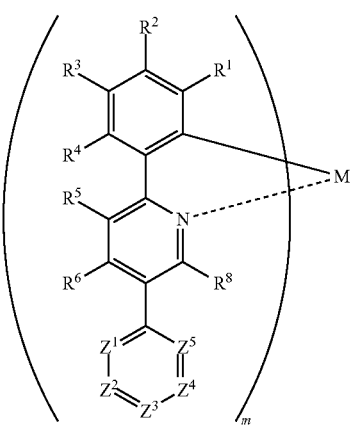

(1a)

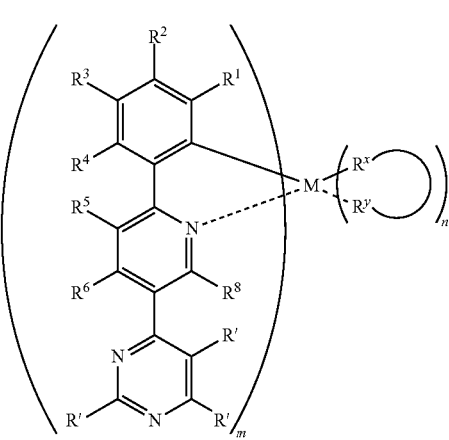

(7-1)

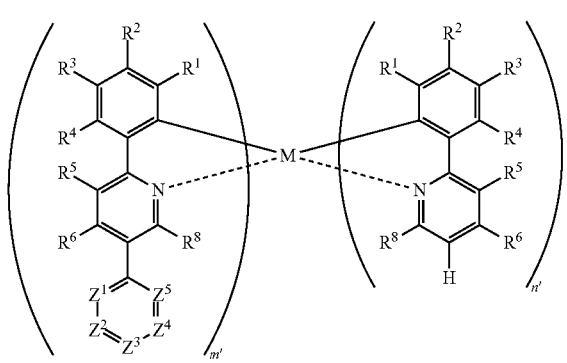

(1b)

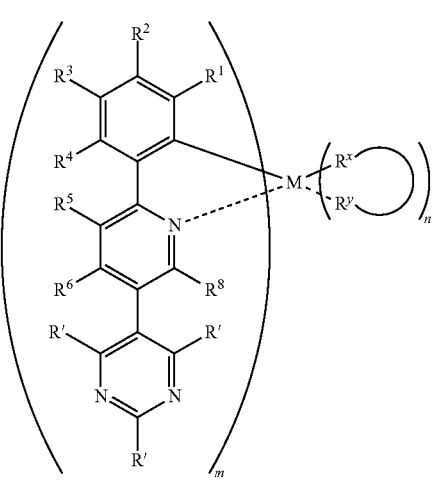

(7-2)

(wherein M, $R^1$, $R^2$, $R^3$, $R^4$, $R^5$, $R^6$, $R^8$, $Z^1$, $Z^2$, $Z^3$, $Z^4$, $Z^5$, and m are as defined above; m' and n' each independently are 1 or 2), and more preferably is a metal complex represented by the formula (1a). However, in the formula (1b), m'+n' is the total number of ligands that can be bonded to the central metal M. An atom and a group represented by $R^1$, $R^2$, $R^3$, $R^4$, $R^5$, $R^6$, and $R^8$ are the same as those described and exemplified as R mentioned later.

From the viewpoint of easiness to adjust luminescent color, as the metal complex represented by the formula (1), a metal complex is preferable in which $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group. In this metal complex, $R^3$ and $R^4$, or $R^5$ and $R^6$ may be bonded to form a ring.

From the viewpoint of luminous properties, a metal complex represented by the following formulas (7-1) to (7-6), (1c), or (1d) is preferable as the metal complex represented by the formula (1), and a metal complex represented by the following formula (1c) or (1d) is more preferable.

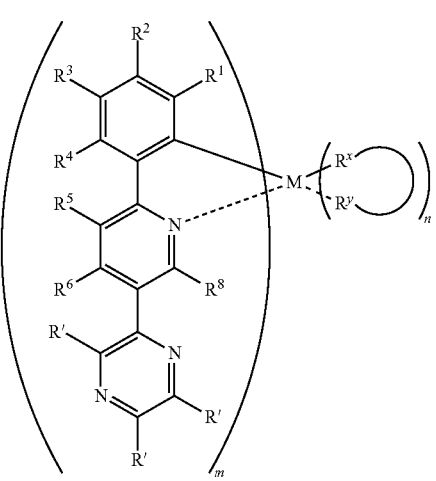

(7-3)

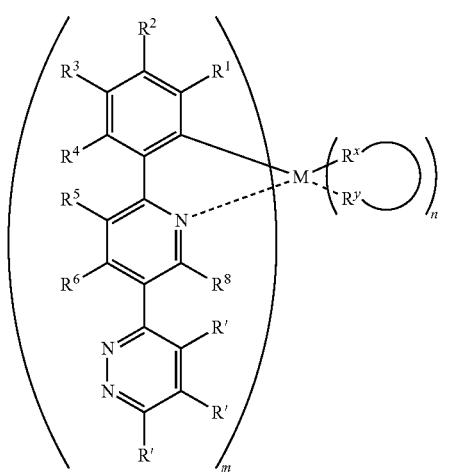

(7-4)

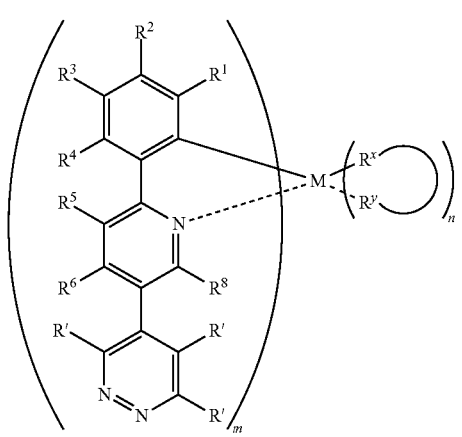

(7-5)

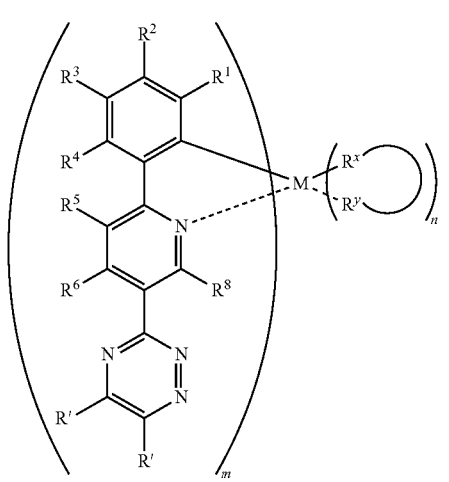

(7-6)

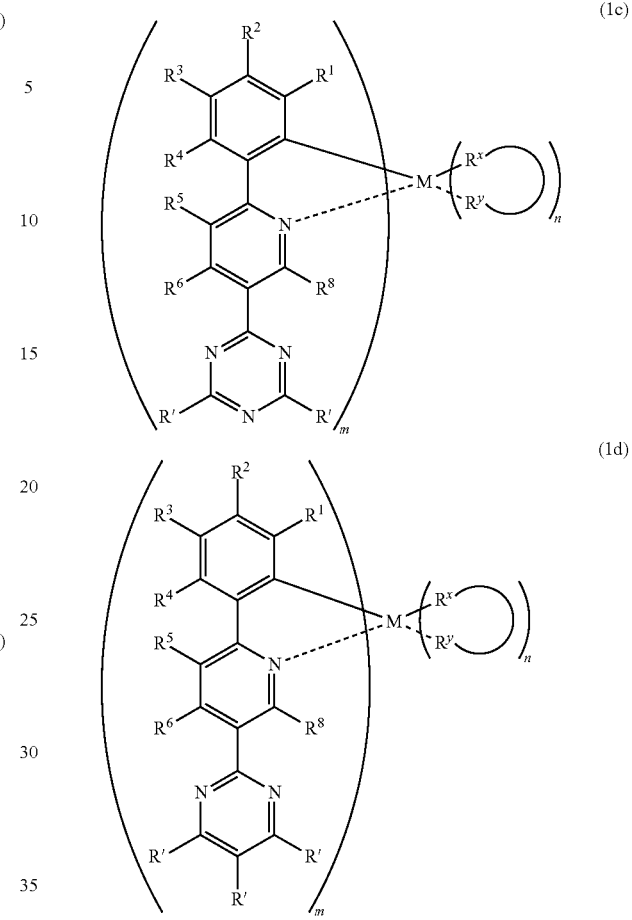

(wherein a monoanionic bidentate ligand represented by M, $R^1$, $R^2$, $R^3$, $R^4$, $R^5$, $R^6$, $R^8$, m, n, and the formula (2) are as defined above; R' represents a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group; a plurality of R' may be the same or different.)

In the formulas (7-1) to (7-6), (1c), and (1d), the halogen atom, the alkyl group, the alkoxy group, the alkylthio group, the aryl group, the aryloxy group, the arylthio group, the arylalkyl group, the arylalkoxy group, the arylalkylthio group, the acyl group, the acyloxy group, the amide group, the acid imide group, the imine residue, the substituted amino group, the substituted silyl group, the substituted silyloxy group, the substituted silylthio group, the substituted silylamino group, the monovalent heterocyclic group, the heteroaryloxy group, the heteroarylthio group, the arylalkenyl group, the arylalkynyl group, the substituted carboxyl group, and the cyano group represented by R' are the same as those described and exemplified as R mentioned later.

The ligand that forms the metal complex influences the luminescent color, luminescence intensity, luminous efficiency of the metal complex, and the like. Accordingly, as the metal complex, a metal complex having a ligand that minimizes a deactivation process of energy in the ligand is preferable. Further, because a kind of a substituent that the ligand has and/or a substitution position influence the electronic characteristics of the ligand, these influence properties of the metal complex. From the above viewpoint, it is thought that in the polymer compound according to the present invention, a polymer compound having high luminous efficiency is obtained by having the residue of the metal complex represented by the formula (1).

Preferably, the metal complex is represented by the formula (1c) or the formula (1d), and n is 0. More preferably, the metal complex is represented by the formula (1c), and n is 0.

The metal atom M serving as the central metal of the metal complex is a metal atom of ruthenium, rhodium, palladium, osmium, iridium, or platinum. Osmium, iridium, and platinum are preferable, iridium and platinum are more preferable, and iridium is particularly preferable. These metal atoms provide spin-orbit interaction on the metal complex, and can cause intersystem crossing between a singlet state and a triplet state.

In the metal complex represented by the formula (1), the formula (1a), or the formula (1b), examples of the bidentate chelating ligand include a ligand represented by the following formula:

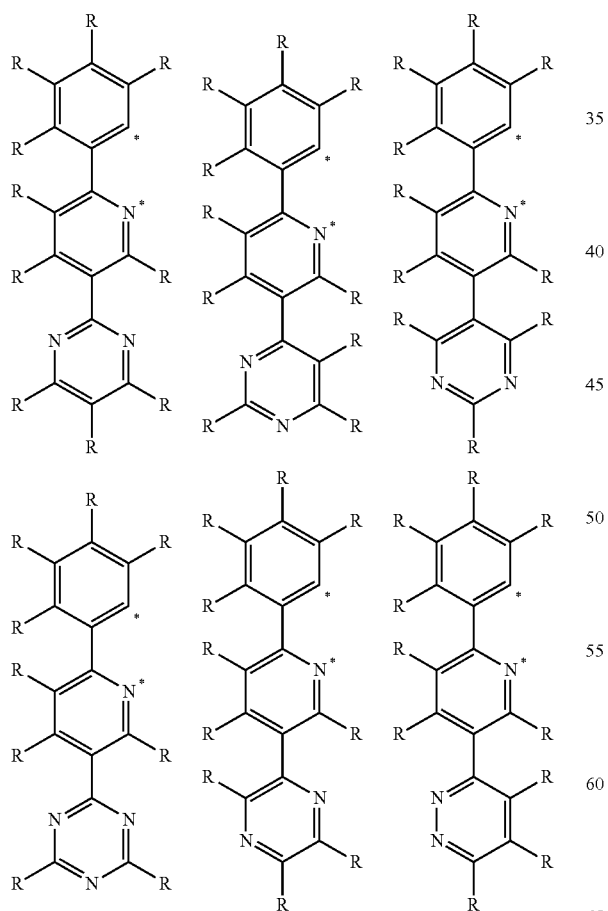

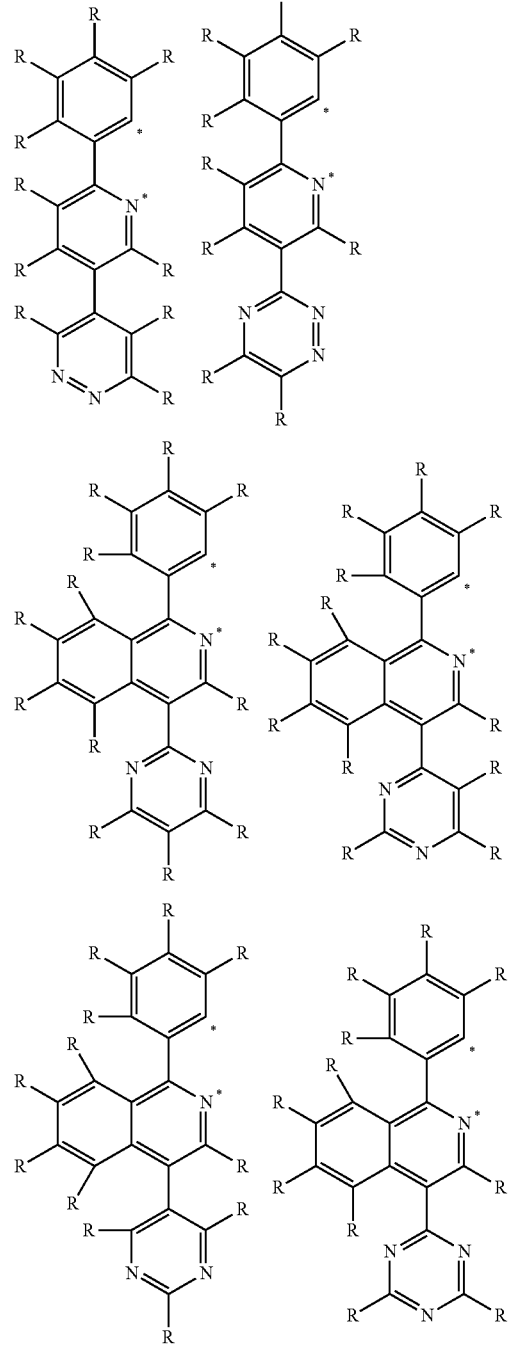

(wherein R is a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group; * represents a site bonded to the metal atom M; a plurality of R may be the same or different.)

Examples of the halogen atom represented by R include a fluorine atom, a chlorine atom, a bromine atom, and an iodine atom.

The alkyl group represented by R may be linear, branched, or cyclic. The number of carbon atoms of this alkyl group is usually 1 to 10. Examples of the alkyl group include a methyl group, an ethyl group, a propyl group, an isopropyl group, a butyl group, an s-butyl group, an isobutyl group, a t-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoro ethyl group, a perfluoro butyl group, a perfluoro hexyl group, and a perfluoro octyl group. The t-butyl group, pentyl group, the hexyl group, the octyl group, the 2-ethylhexyl group, the decyl group, and the 3,7-dimethyloctyl group are preferable.

The alkoxy group represented by R may be linear, branched, or cyclic. The number of carbon atoms of this alkoxy group is usually 1 to 10. Examples of the alkoxy group include a methoxy group, an ethoxy group, a propyloxy group, an isopropyloxy group, a butoxy group, an isobutoxy group, a t-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyl group, a perfluorooctyl group, a methoxymethyloxy group, and a 2-methoxyethyloxy group. The pentyloxy group, the hexyloxy group, the octyloxy group, the 2-ethylhexyloxy group, the decyloxy group, and the 3,7-dimethyloctyloxy group are preferable.

The alkylthio group represented by R may be linear, branched, or cyclic. The number of carbon atoms of this alkylthio group is usually 1 to 10. Examples of the alkylthio group include a methylthio group, an ethylthio group, a propylthio group, an isopropylthio group, a butylthio group, an s-butylthio group, an isobutylthio group, a t-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group, and a trifluoromethylthio group. The pentylthio group, the hexylthio group, the octylthio group, the 2-ethylhexylthio group, the decylthio group, and the 3,7-dimethyloctylthio group are preferable.

The number of carbon atoms of the aryl group represented by R is usually 6 to 60, and preferably 7 to 48. Examples of the aryl group include a phenyl group, a $C_1$ to $C_{12}$ alkoxyphenyl group ("$C_1$ to $C_{12}$ alkoxy" means that the number of carbon atoms of an alkoxy portion is 1 to 12. Hereinafter, the same applies), a $C_1$ to $C_{12}$ alkylphenyl group ("$C_1$ to $C_{12}$ alkyl" means that the number of carbon atoms of an alkyl portion is 1 to 12. Hereinafter, the same applies), a 1-naphthyl group, a 2-naphthyl group, a 1-anthracenyl group, a 2-anthracenyl group, a 9-anthracenyl group, and a pentafluorophenyl group. The $C_1$ to $C_{12}$ alkoxyphenyl group and $C_1$ to $C_{12}$ alkylphenyl group are preferable. Here, the aryl group is an atomic group in which one hydrogen atom is removed from an aromatic hydrocarbon. Examples of this aromatic hydrocarbon include those having a condensed ring, and those in which two or more independent benzene rings or two or more condensed rings are bonded directly or through a group such as vinylene. Further, the aryl group may have a substituent. Examples of the substituent include a $C_1$ to $C_{12}$ alkoxyphenyl group, and a $C_1$ to $C_{12}$ alkylphenyl group.

Examples of the $C_1$ to $C_{12}$ alkoxyphenyl group include a methoxyphenyl group, an ethoxyphenyl group, a propyloxyphenyl group, an isopropyloxyphenyl group, a butoxyphenyl group, an isobutoxyphenyl group, a t-butoxyphenyl group, a pentyloxyphenyl group, a hexyloxyphenyl group, a cyclohexyloxyphenyl group, a heptyloxyphenyl group, an octyloxyphenyl group, a 2-ethylhexyloxyphenyl group, a nonyloxyphenyl group, a decyloxyphenyl group, a 3,7-dimethyloctyloxyphenyl group, and a lauryloxyphenyl group.

Examples of the $C_1$ to $C_{12}$ alkylphenyl group include a methylphenyl group, an ethylphenyl group, a dimethylphenyl group, a propylphenyl group, a mesityl group, a methylethylphenyl group, an isopropylphenyl group, a butylphenyl group, an s-butylphenyl group, an isobutylphenyl group, a t-butylphenyl group, a pentylphenyl group, an isoamylphenyl group, a hexylphenyl group, a heptylphenyl group, an octylphenyl group, a nonylphenyl group, a decylphenyl group, and a dodecylphenyl group.

The number of carbon atoms of the aryloxy group represented by R is usually 6 to 60, and preferably 7 to 48. Examples of the aryloxy group include a phenoxy group, a $C_1$ to $C_{12}$ alkoxyphenoxy group, a $C_1$ to $C_{12}$ alkylphenoxy group, a 1-naphthyloxy group, 2-naphthyloxy group, and a pentafluorophenyloxy group. The $C_1$ to $C_{12}$ alkoxyphenoxy group and the $C_1$ to $C_{12}$ alkylphenoxy group are preferable.

Examples of the $C_1$ to $C_{12}$ alkoxyphenoxy group include a methoxyphenoxy group, an ethoxyphenoxy group, a propyloxyphenoxy group, an isopropyloxyphenoxy group, a butoxyphenoxy group, an isobutoxyphenoxy group, a t-butoxyphenoxy group, a pentyloxyphenoxy group, a hexyloxyphenoxy group, a cyclohexyloxyphenoxy group, a heptyloxyphenoxy group, an octyloxyphenoxy group, a 2-ethylhexyloxy phenoxy group, a nonyloxyphenoxy group, a decyloxyphenoxy group, a 3,7-dimethyloctyloxyphenoxy group, and a lauryloxyphenoxy group.

Examples of the $C_1$ to $C_{12}$ alkylphenoxy group include a methylphenoxy group, an ethylphenoxy group, a dimethylphenoxy group, a propylphenoxy group, a 1,3,5-trimethylphenoxy group, a methylethylphenoxy group, an isopropylphenoxy group, a butylphenoxy group, an s-butylphenoxy group, an isobutylphenoxy group, a t-butylphenoxy group, a pentylphenoxy group, an isoamylphenoxy group, a hexylphenoxy group, a heptylphenoxy group, an octylphenoxy group, a nonylphenoxy group, a decylphenoxy group, and a dodecylphenoxy group.

The number of carbon atoms of the arylthio group is usually 6 to 60, and preferably 7 to 48. Examples of the arylthio group include a phenylthio group, a $C_1$ to $C_{12}$ alkoxyphenylthio group, a $C_1$ to $C_{12}$ alkylphenylthio group, a 1-naphthylthio group, a 2-naphthylthio group, and a pentafluorophenylthio group. The $C_1$ to $C_{12}$ alkoxyphenylthio group and the $C_1$ to $C_{12}$ alkylphenylthio group are preferable.

The number of carbon atoms of the arylalkyl group represented by R is usually 7 to 60, and preferably 7 to 48. Examples of the arylalkyl group include a phenyl-$C_1$ to $C_{12}$ alkyl group, a $C_1$ to $C_{12}$ alkoxyphenyl-$C_1$ to $C_{12}$ alkyl group, a $C_1$ to $C_{12}$ alkylphenyl-$C_1$ to $C_{12}$ alkyl group, a 1-naphthyl-$C_1$ to $C_{12}$ alkyl group, and a 2-naphthyl-$C_1$ to $C_{12}$ alkyl group. The $C_1$ to $C_{12}$ alkoxyphenyl-$C_1$ to $C_{12}$ alkyl group and the $C_1$ to $C_{12}$ alkylphenyl-$C_1$ to $C_{12}$ alkyl group are preferable.

The number of carbon atoms of the aryl alkoxy group represented by R is usually 7 to 60, and preferably 7 to 48. Examples of the arylalkoxy group include a phenyl-$C_1$ to $C_{12}$ alkoxy group such as a phenylmethoxy group, a phenylethoxy group, a phenylbutoxy group, a phenylpentyloxy group, a phenylhexyloxy group, a phenylheptyloxy group, and a phenyloctyloxy group, a $C_1$ to $C_{12}$ alkoxyphenyl-$C_1$ to $C_{12}$ alkoxy group, $C_1$ to $C_{12}$ alkylphenyl-$C_1$ to $C_{12}$ alkoxy group, 1-naphthyl-$C_1$ to $C_{12}$ alkoxy group, and 2-naphthyl-$C_1$ to $C_{12}$ alkoxy group. The $C_1$ to $C_{12}$ alkoxyphenyl-$C_1$ to $C_{12}$ alkoxy group and the $C_1$ to $C_{12}$ alkylphenyl-$C_1$ to $C_{12}$ alkoxy group are preferable.

The number of carbon atoms of the aryl alkylthio group represented by R is usually 7 to 60, and preferably 7 to 48. Examples of the arylalkylthio group include a phenyl-$C_1$ to $C_{12}$ alkylthio group, a $C_1$ to $C_{12}$ alkoxyphenyl-$C_1$ to $C_{12}$ alkylthio group, a $C_1$ to $C_{12}$ alkylphenyl-$C_1$ to $C_{12}$ alkylthio group, a 1-naphthyl-$C_1$ to $C_{12}$-alkylthio group, and 2-naphthyl-$C_1$ to $C_{12}$ alkylthio group. The $C_1$ to $C_{12}$ alkoxyphenyl-$C_1$ to $C_{12}$ alkylthio group and the $C_1$ to $C_{12}$ alkylphenyl-$C_1$ to $C_{12}$ alkylthio group are preferable.

The number of carbon atoms of the acyl group represented by R is usually 2 to 20, and preferably 2 to 18. Examples of the acyl group include an acetyl group, a propionyl group, a butyryl group, an isobutyryl group, a pivaloyl group, a benzoyl group, a trifluoroacetyl group, and a pentafluorobenzoyl group.

The number of carbon atoms of the acyloxy group represented by R is usually 2 to 20, and preferably 2 to 18. Examples of the acyloxy group include an acetoxy group, a propionyloxy group, a butyryloxy group, an isobutyryloxy group, a pivaloyloxy group, a benzoyloxy group, a trifluoroacetyloxy group, and a pentafluorobenzoyloxy group.

The number of carbon atoms of the amide group represented by R is usually 2 to 20, and preferably 2 to 18. Examples of the amide group include a formamide group, an acetamide group, a propioamide group, a butyramide group, a benzamide group, a trifluoroacetamide group, a pentafluorobenzamide group, a diformamide group, a diacetoamide group, a dipropioamide group, a dibutyramide group, a dibenzamide group, a ditrifluoroacetamide group, and a dipentafluorobenzamide group.

The acid imide group represented by R means a monovalent residue obtained by removing one hydrogen atom bonded to the nitrogen atom from acid imide. The number of carbon atoms of this acid imide group is usually 2 to 60, and preferably 2 to 48. Examples of the acid imide group include a group shown by the following structural formula:

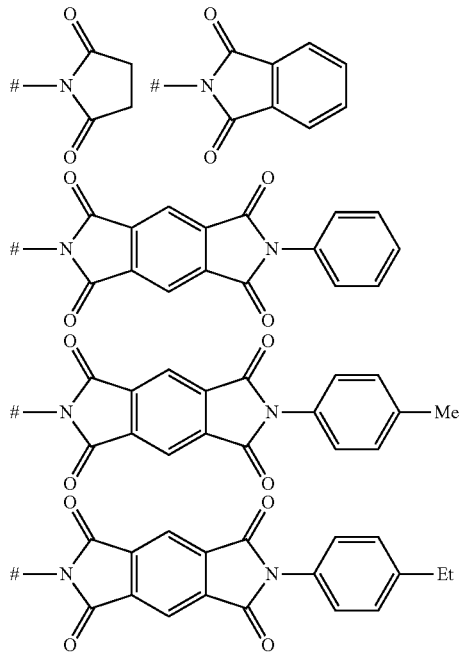

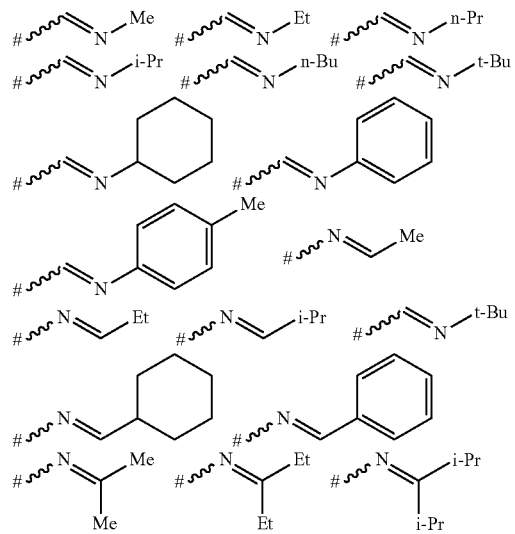

(wherein a line extended from a nitrogen atom represents a bond; Me represents a methyl group, Et represents an ethyl group, and n-Pr represents an n-propyl group; hereinafter, it is as defined above; # represents a bond.)

The imine residue represented by R means a monovalent residue obtained by removing one hydrogen atom from an imine compound (namely, it is an organic compound having —N=C— in the molecule. Examples thereof include a compound in which aldimine, ketimine, and a hydrogen atom bonded to a nitrogen atom in these molecules are substituted by an alkyl group or the like.) This imine residue usually has 2 to 20 carbon atoms, and preferably has 2 to 18 carbon atoms. Specifically, examples thereof include a group shown by the following structural formula:

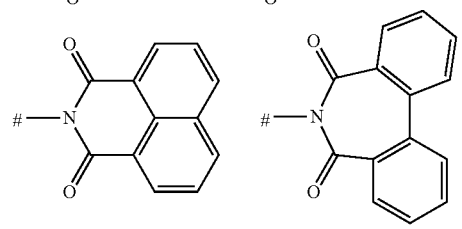

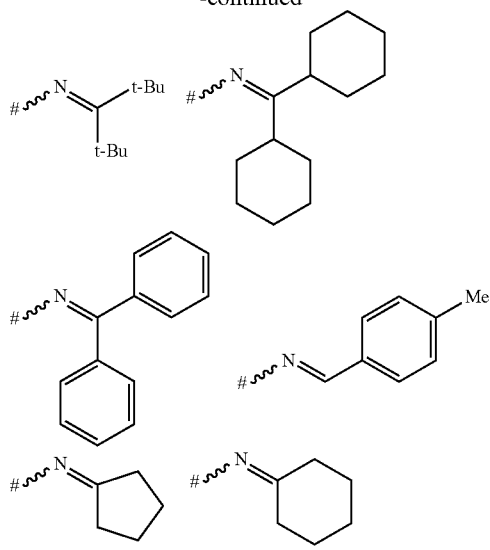

(wherein i-Pr represents an isopropyl group, n-Bu represents an n-butyl group, and t-Bu represents a t-butyl group; a bond shown by a wavy line means a "bond represented by a wedge shape" and/or a "bond represented by a dashed line"; here, the "bond represented by the wedge shape" means a bond projected from space toward the front, and the "bond represented by the dashed line" means a bond projected to the other side of space; # represents a bond.)

The substituted amino group represented by R means an amino group substituted by one or two groups selected from the group consisting of an alkyl group, an aryl group, an arylalkyl group, and a monovalent heterocyclic group. The alkyl group, the aryl group, the arylalkyl group, or the monovalent heterocyclic group may have a substituent. The number of carbon atoms of the substituted amino group is usually 1 to 60 without including carbon atoms of the substituent, and preferably 2 to 48. Examples of the substituted amino group include a methylamino group, a dimethylamino group, an ethylamino group, a diethylamino group, a propylamino group, a dipropylamino group, an isopropylamino group, a diisopropylamino group, a butylamino group, an s-butylamino group, an isobutylamino group, a t-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_1$ to $C_{12}$ alkoxyphenylamino group, a di($C_1$ to $C_{12}$ alkoxyphenyl)amino group, a di($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-$C_1$ to $C_{12}$ alkylamino group, a $C_1$ to $C_{12}$ alkoxyphenyl-$C_1$ to $C_{12}$ alkylamino group, $C_1$ to $C_{12}$ alkylphenyl-$C_1$ to $C_{12}$ alkylamino group, a di($C_1$ to $C_{12}$ alkoxyphenyl-$C_1$ to $C_{12}$ alkyl)amino group, a di($C_1$ to $C_{12}$ alkylphenyl-$C_1$ to $C_{12}$ alkyl)amino group, a 1-naphthyl-$C_1$ to $C_{12}$ alkylamino group, and a 2-naphthyl-$C_1$ to $C_{12}$ alkylamino group.

The substituted silyl group represented by R means a silyl group substituted by one, two, or three groups selected from the group consisting of an alkyl group, an aryl group, an arylalkyl group, and a monovalent heterocyclic group. The number of carbon atoms of the substituted silyl group is usually 1 to 60, and preferably 3 to 48. The alkyl group, the aryl group, the aryl alkyl group, or the monovalent heterocyclic group may have a substituent. Examples of the substituted silyl group include a trimethylsilyl group, a triethylsilyl group, a tripropylsilyl group, a triisopropylsilyl group, a dimethylisopropylsilyl group, a diethylisopropylsilyl group, a t-butyldimethylsilyl group, a pentyldimethylsilyl group, a hexyldimethylsilyl group, a heptyldimethylsilyl group, an octyldimethylsilyl group, a 2-ethylhexyldimethylsilyl group, a nonyldimethylsilyl group, a decyldimethylsilyl group, a 3,7-dimethyloctyldimethylsilyl group, a lauryldimethylsilyl group, a phenyl-$C_1$ to $C_{12}$ alkylsilyl group, a $C_1$ to $C_{12}$ alkoxyphenyl-$C_1$ to $C_{12}$ alkylsilyl group, a $C_1$ to $C_{12}$ alkylphenyl-$C_1$ to $C_{12}$ alkylsilyl group, a 1-naphthyl-$C_1$ to $C_{12}$ alkylsilyl group, a 2-naphthyl $C_1$ to $C_{12}$ alkylsilyl group, a phenyl-$C_1$ to $C_{12}$ alkyldimethylsilyl group, a triphenylsilyl group, a tri-p-xylylsilyl group, a tribenzylsilyl group, a diphenylmethylsilyl group, a t-butylphenylsilyl group, and a dimethylphenylsilyl group.

The substituted silyloxy group represented by R means a silyloxy group substituted by one, two, or three groups selected from the group consisting of an alkoxy group, an aryloxy group, an arylalkoxy group, and a monovalent heterocyclic-oxy group. The number of carbon atoms of the substituted silyloxy group is usually 1 to 60, and preferably 3 to 48. The alkoxy group, the aryloxy group, the aryl alkoxy group, or the monovalent heterocyclic oxy group may have a substituent. Examples of the substituted silyloxy group include a trimethylsilyloxy group, a triethylsilyloxy group, a tripropylsilyloxy group, a triisopropylsilyloxy group, a dimethylisopropylsilyloxy group, a diethylisopropylsilyloxy group, a t-butyldimethylsilyloxy group, a pentyldimethylsilyloxy group, a hexyldimethylsilyloxy group, a heptyldimethylsilyloxy group, an octyldimethylsilyloxy group, a 2-ethylhexyldimethylsilyloxy group, a nonyldimethylsilyloxy group, a decyldimethylsilyloxy group, a 3,7-dimethyloctyldimethylsilyloxy group, a lauryldimethylsilyloxy group, a phenyl-$C_1$ to $C_{12}$ alkylsilyloxy group, a $C_1$ to $C_{12}$ alkoxyphenyl-$C_1$ to $C_{12}$ alkylsilyloxy group, a $C_1$ to $C_{12}$ alkylphenyl-$C_1$ to $C_{12}$ alkylsilyloxy group, a 1-naphthyl-$C_1$ to $C_{12}$ alkylsilyloxy group, a 2-naphthyl-$C_1$ to $C_{12}$ alkylsilyloxy group, a phenyl-$C_1$ to $C_{12}$ alkyldimethylsilyloxy group, a triphenylsilyloxy group, a tri-p-xylylsilyloxy group, a tribenzylsilyloxy group, a diphenylmethylsilyloxy group, a t-butylphenylsilyloxy group, and a dimethylphenylsilyloxy group.

The substituted silylthio group represented by R means a silylthio group substituted by one, two, or three groups selected from the group consisting of an alkylthio group, an arylthio group, an arylalkylthio group, and a monovalent heterocyclic-thio group. The number of carbon atoms of the substituted silylthio group is usually 1 to 60, and preferably 3 to 48. The alkoxy group, the arylthio group, the arylalkylthio group, or the monovalent heterocyclic thio group may have a substituent. Examples of the substituted silylthio group include a trimethylsilylthio group, a triethylsilylthio group, a tripropylsilylthio group, a triisopropylsilylthio group, a dimethylisopropylsilylthio group, a diethylisopropylsilylthio group, a t-butyldimethylsilylthio group, a pentyldimethylsilylthio group, a hexyldimethylsilylthio group, a heptyldimethylsilylthio group, an octyldimethylsilylthio group, a 2-ethylhexyldimethylsilylthio group, a nonyldimethylsilylthio group, a decyldimethylsilylthio group, a 3,7-dimethyloctyldimethylsilylthio group, a lauryldimethylsilylthio group, a phenyl-$C_1$ to $C_{12}$ alkylsilylthio group, a $C_1$ to $C_{12}$ alkoxyphenyl-$C_1$ to $C_{12}$ alkylsilylthio group, a $C_1$ to $C_{12}$ alkylphenyl-$C_1$ to $C_{12}$ alkylsilylthio group, a 1-naphthyl-$C_1$ to $C_{12}$ alkylsilylthio group, a 2-naphthyl-$C_1$ to $C_{12}$ alkylsilylthio group, a phenyl-$C_1$ to $C_{12}$ alkyldimethylsilylthio group, a triphenylsilylthio group, a tri-p-xylylsilylthio group, a tribenzylsilylthio group, a diphenylmethylsilylthio group, a t-butylphenylsilylthio group, and a dimethylphenylsilylthio group.

The substituted silyl amino group represented by R means a silylamino group substituted by one, two, or three groups selected from the group consisting of an alkylamino group, an arylamino group, an arylalkylamino group, and a monovalent heterocyclic-amino group. The number of carbon atoms of the substituted silyl amino group is usually 1 to 60, and preferably 3 to 48. The alkoxy group, the arylamino group, the arylalkylamino group, or the monovalent heterocyclic amino group may have a substituent. Examples of the substituted silylamino group include a trimethylsilylamino group, a triethylsilylamino group, a tripropylsilylamino group, a triisopropylsilylamino group, a dimethylisopropylsilylamino group, a diethylisopropylsilylamino group, a t-butyldimethylsilylamino group, a pentyldimethylsilylamino group, a hexyldimethylsilylamino group, a heptyldimethylsilylamino group, an octyldimethylsilylamino group, a 2-ethylhexyldimethylsilylamino group, a nonyldimethylsilylamino group, a decyldimethylsilylamino group, a 3,7-dimethyloctyldimethylsilylamino group, a lauryldimethylsilylamino group, a phenyl-$C_1$ to $C_{12}$ alkylsilyloxy group, $C_1$ to $C_{12}$ alkoxyphenyl-$C_1$ to $C_{12}$ alkylsilylamino group, a $C_1$ to $C_{12}$ alkylphenyl-$C_1$ to $C_{12}$ alkylsilylamino group, a 1-naphthyl-$C_1$ to $C_{12}$ alkylsilylamino group, a 2-naphthyl-$C_1$ to $C_{12}$ alkylsilylamino group, a phenyl-$C_1$ to $C_{12}$ alkyldimethylsilylamino group, a triphenylsilylamino group, a tri-p-xylylsilylamino group, a tribenzylsilylamino group, a diphenylmethylsilylamino group, a t-butylphenylsilylamino group, and a dimethylphenylsilylamino group.

The monovalent heterocyclic group represented by R means an atomic group that remains by removing one hydrogen atom from a heterocyclic compound. The number of carbon atoms of the monovalent heterocyclic group is usually 3 to 60, and preferably 3 to 20. Carbon atoms of a substituent are not included in the carbon atoms of the monovalent heterocyclic group. Here, the heterocyclic compound refers to those in which a device that forms a ring includes not only a carbon atom but also a hetero atom such as oxygen, sulfur, nitrogen, phosphorus, boron in the ring among organic compounds having a cyclic structure. Examples of the monovalent heterocyclic group include a thienyl group, a $C_1$ to $C_{12}$ alkylthienyl group, a pyrrolyl group, a furyl group, a pyridyl group, a $C_1$ to $C_{12}$ alkylpyridyl group, a pyrimidyl group, a $C_1$ to $C_{12}$ alkylpyrimidyl group, a triazyl group, a $C_1$ to $C_{12}$ alkyltriazyl group, a piperidyl group, a quinolyl group, and an isoquinolyl group. The thienyl group, the $C_1$ to $C_{12}$ alkylthienyl group, the pyridyl group, the $C_1$ to $C_{12}$ alkylpyridyl group, the pyrimidyl group, the $C_1$ to $C_{12}$ alkylpyrimidyl group, the triazyl group, the $C_1$ to $C_{12}$ alkyltriazyl group are preferable. Preferably, the monovalent heterocyclic group is a monovalent aromatic heterocyclic group.

The number of carbon atoms of the heteroaryloxy group represented by R is usually 6 to 60, and preferably 7 to 48. Examples of the heteroaryloxy group include a thienyl group, a $C_1$ to $C_{12}$ alkoxythienyl group, a $C_1$ to $C_{12}$ alkylthienyl group, a pyridyloxy group, a pyridyloxy group, and an isoquinolyloxy group. The $C_1$ to $C_{12}$ alkoxypyridyl group and the $C_1$ to $C_{12}$ alkylpyridyl group are preferable.

Examples of the $C_1$ to $C_{12}$ alkoxypyridyl group include a methoxypyridyl group, an ethoxypyridyl group, a propyloxypyridyl group, an isopropyloxypyridyl group, a butoxypyridyl group, an isobutoxypyridyl group, a t-butoxypyridyl group, a pentyloxypyridyl group, a hexyloxypyridyl group, a cyclohexyloxypyridyl group, a heptyloxypyridyl group, an octyloxypyridyl group, a 2-ethylhexyloxypyridyl group, a nonyloxypyridyl group, a decyloxypyridyl group, a 3,7-dimethyloctyloxypyridyl group, and a lauryloxypyridyl group.

Examples of the $C_1$ to $C_{12}$ alkylpyridyloxy group include a methylpyridyloxy group, an ethylpyridyloxy group, a dimethylpyridyloxy group, a propylpyridyloxy group, a 1,3,5-trimethylpyridyloxy group, a methylethylpyridyloxy group, an isopropylpyridyloxy group, a butylpyridyloxy group, an s-butylpyridyloxy group, an isobutylpyridyloxy group, a t-butylpyridyloxy group, a pentylpyridyloxy group, an isoamylpyridyloxy group, a hexylpyridyloxy group, a heptylpyridyloxy group, an octylpyridyloxy group, a nonylpyridyloxy group, a decylpyridyloxy group, and a dodecylpyridyloxy group.

The number of carbon atoms of the heteroarylthio group represented by R is usually 6 to 60, and preferably 7 to 48. Examples of the heteroarylthio group include a pyridylthio group, a $C_1$ to $C_{12}$ alkoxypyridylthio group, a $C_1$ to $C_{12}$ alkylpyridylthio group, and an isoquinolylthio group. The $C_1$ to $C_{12}$ alkoxypyridylthio group and the $C_1$ to $C_{12}$ alkylpyridylthio group are preferable.

The number of carbon atoms of the arylalkenyl group represented by R is usually 8 to 60, and preferably 8 to 48. Examples of the arylalkenyl group include a phenyl-$C_2$ to $C_{12}$ alkenyl group ("$C_2$ to $C_{12}$ alkenyl" means that the number of carbon atoms of an alkenyl portion is 2 to 12. Hereinafter, the same applies), a $C_1$ to $C_{12}$ alkoxyphenyl-$C_2$ to $C_{12}$ alkenyl group, a $C_1$ to $C_{12}$ alkylphenyl-$C_2$ to $C_{12}$ alkenyl group, a 1-naphthyl-$C_2$ to $C_{12}$ alkenyl group, and a 2-naphthyl-$C_2$ to $C_{12}$ alkenyl group. The $C_1$ to $C_{12}$ alkoxyphenyl-$C_2$ to $C_{12}$ alkenyl group and a $C_2$ to $C_{12}$ alkylphenyl-$C_1$ to $C_{12}$ alkenyl group are preferable.

The number of carbon atoms of the arylalkynyl group represented by R is usually 8 to 60, and preferably 8 to 48. Examples of the arylalkynyl group include a phenyl-$C_2$ to $C_{12}$-alkynyl group ("$C_2$ to $C_{12}$ alkynyl" means that the number of carbon atoms of an alkynyl portion is 2 to 12. Hereinafter, the same applies), a $C_1$ to $C_{12}$ alkoxyphenyl-$C_2$ to $C_{12}$ alkynyl group, a $C_1$ to $C_{12}$ alkylphenyl-$C_2$ to $C_{12}$ alkynyl group, a 1-naphthyl-$C_2$ to $C_{12}$ alkynyl group, and a 2-naphthyl-$C_2$ to $C_{12}$ alkynyl group. The $C_1$ to $C_{12}$ alkoxyphenyl-$C_2$ to $C_{12}$ alkynyl group and the $C_1$ to $C_{12}$ alkylphenyl-$C_2$ to $C_{12}$ alkynyl group are preferable.

The number of carbon atoms of the substituted carboxyl group represented by R is usually 2 to 60, and preferably 2 to 48. The substituted carboxyl group represented by R means a carboxyl group substituted by an alkyl group, an aryl group, an arylalkyl group, or a monovalent heterocyclic group. Examples of the substituted carboxyl group include a methoxycarbonyl group, an ethoxycarbonyl group, a carbopropoxy group, an isopropoxycarbonyl group, a butoxycarbonyl group, an isocarbobutoxy group, a t-butoxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethoxycarbonyl group, a pentafluoroethoxycarbonyl group, a perfluorobutoxycarbonyl group, a perfluorohexyloxycarbonyl group, a perfluorooctyloxycarbonyl group, a pyridyloxycarbonyl group, a naphthoxycarbonyl group, and a pyridyloxycarbonyl group. The alkyl group, the aryl group, the arylalkyl group, or the monovalent heterocyclic group may have a substituent. The carbon atoms of the substituent are not included in the carbon atoms of the substituted carboxyl group.

The monoanionic bidentate ligand is preferably a bidentate ligand having the number of atoms of 3 to 30 other than a hydrogen atom in the bidentate ligand represented by the formula (2). Examples thereof include bidentate ligands represented by the following formulas:

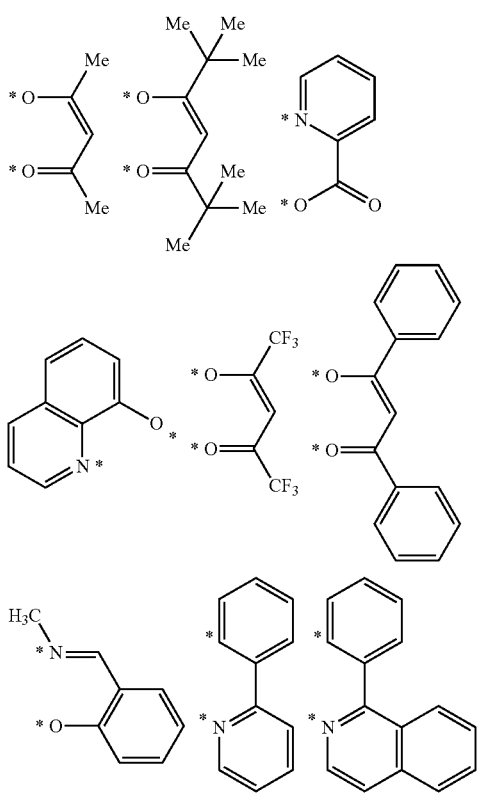

(wherein * represents a site bonded to a metal atom M.)

Examples of the metal complex include compounds shown below:

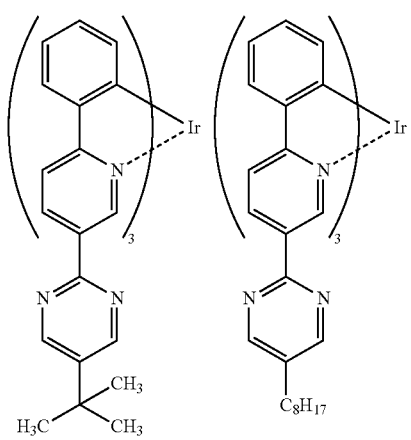

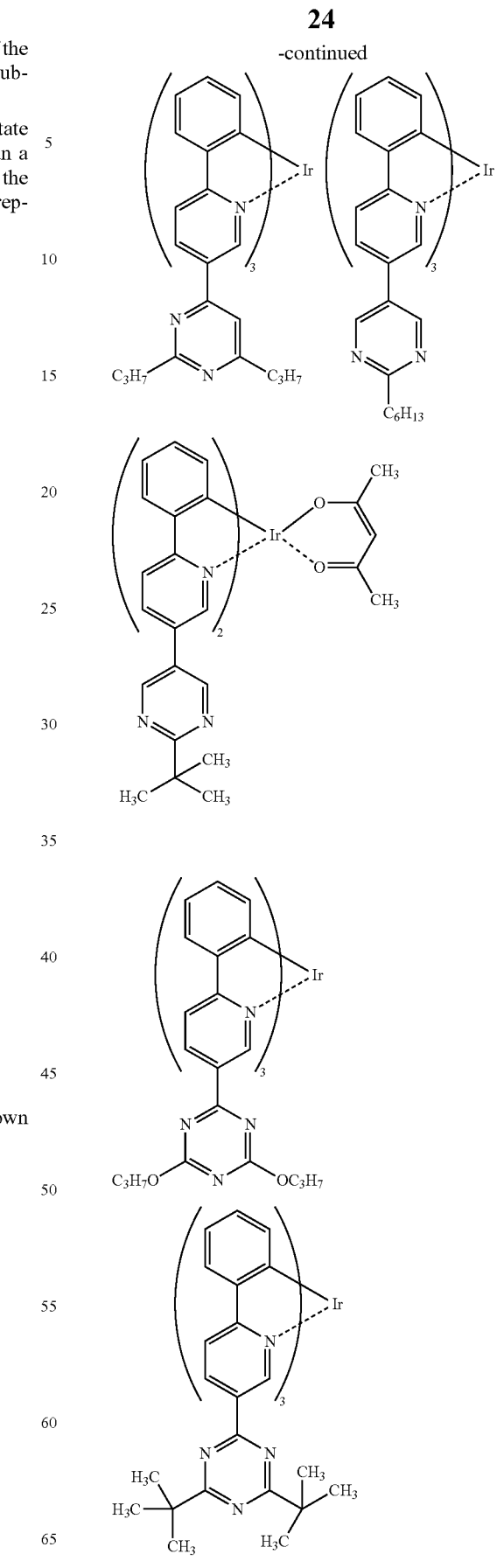

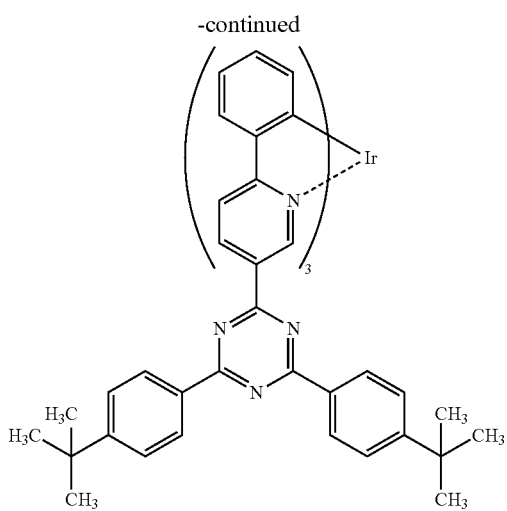
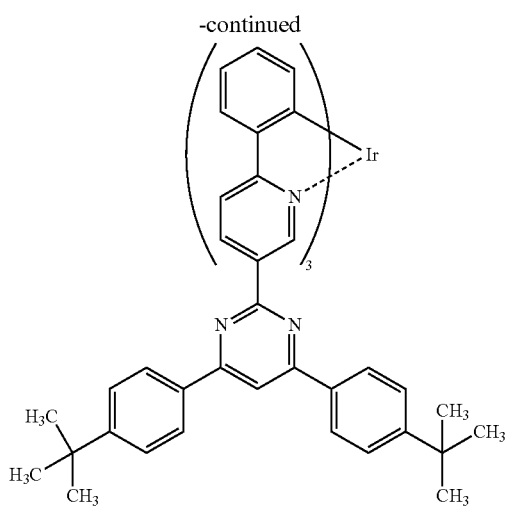
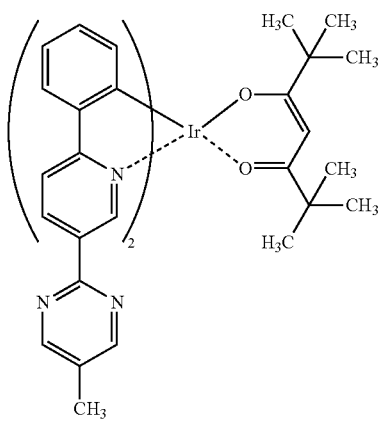
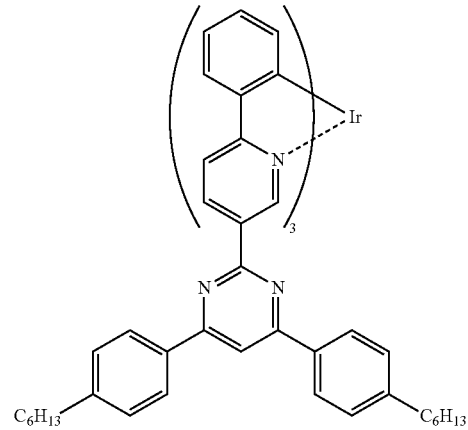
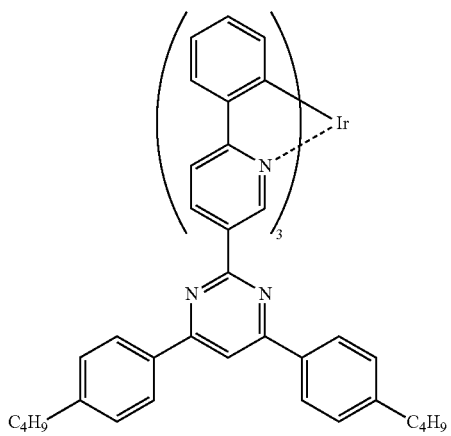
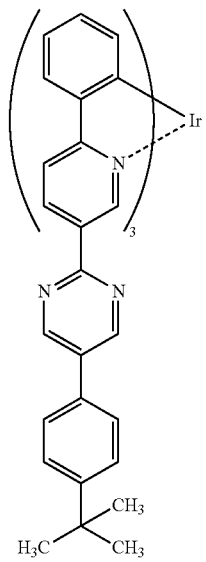

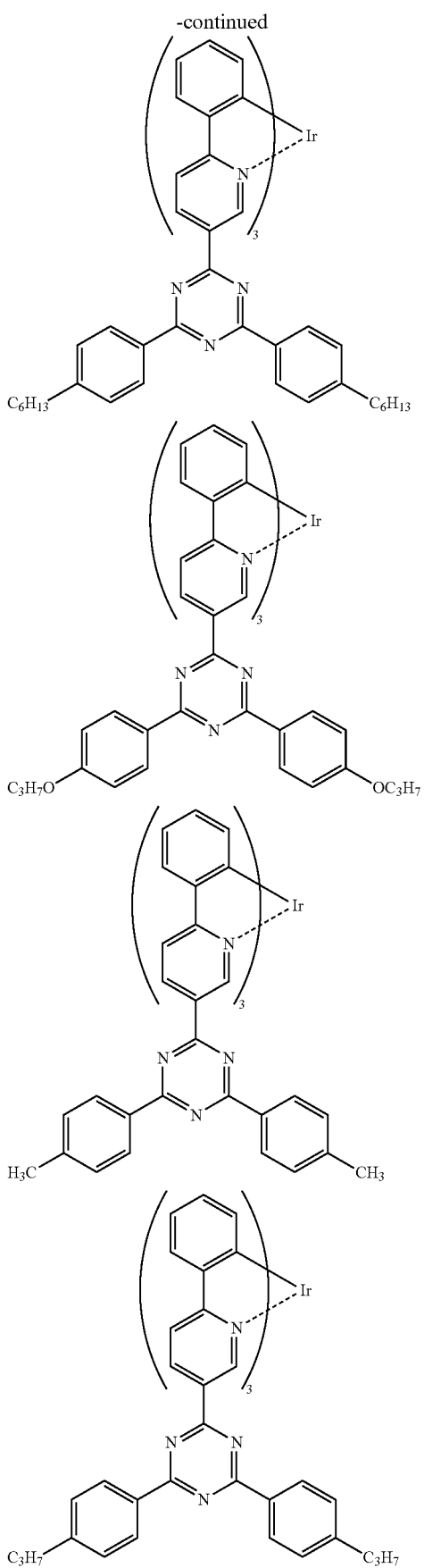
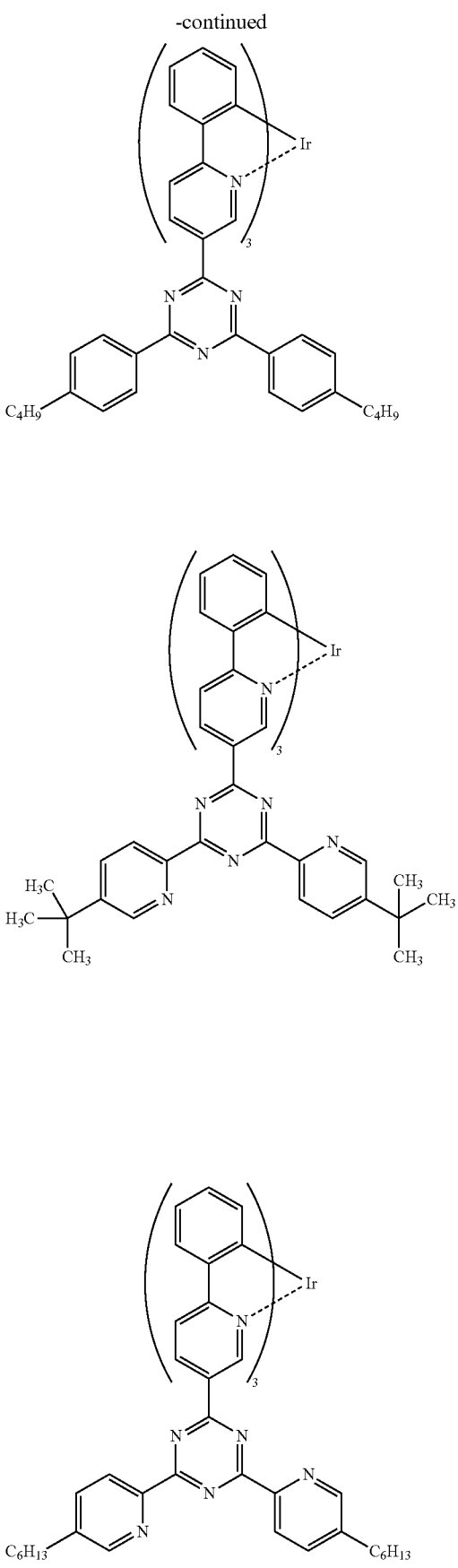

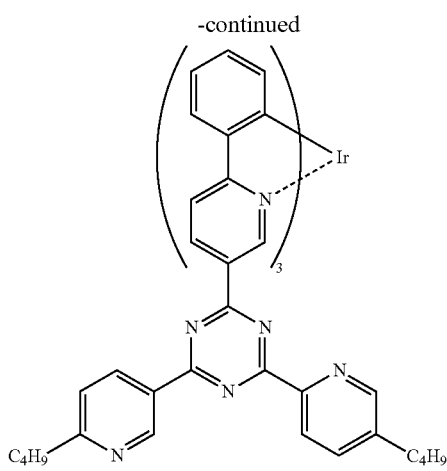
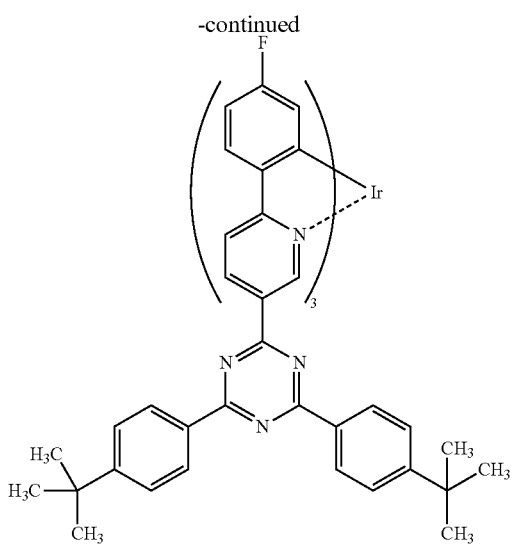
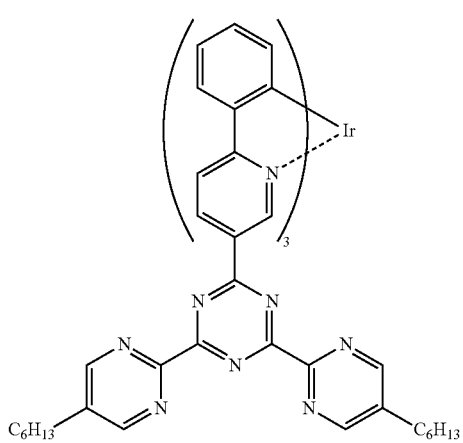
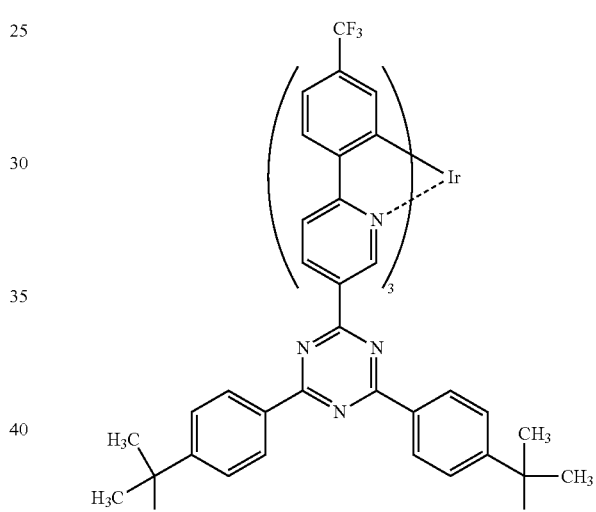
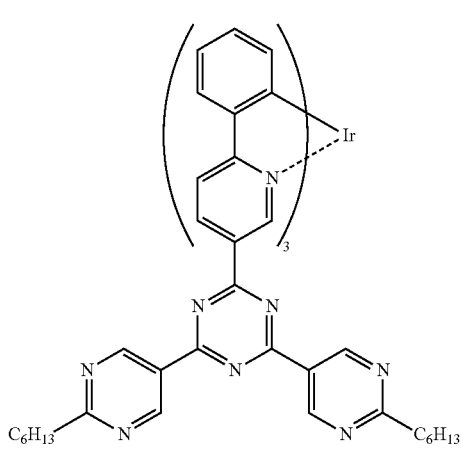
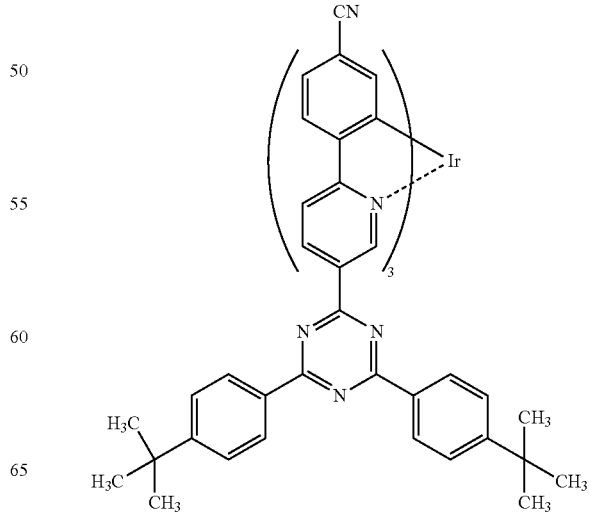

31
-continued
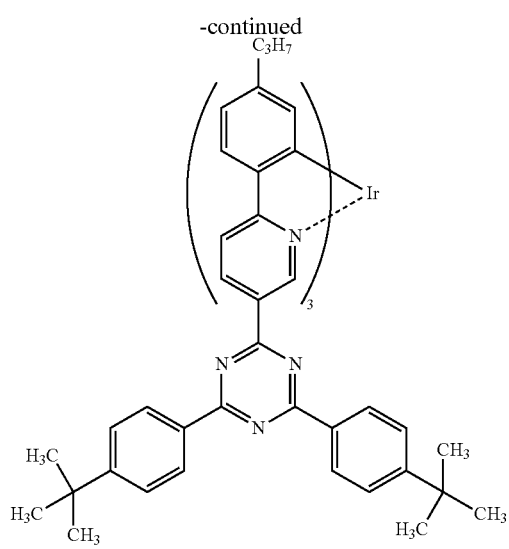
32
-continued
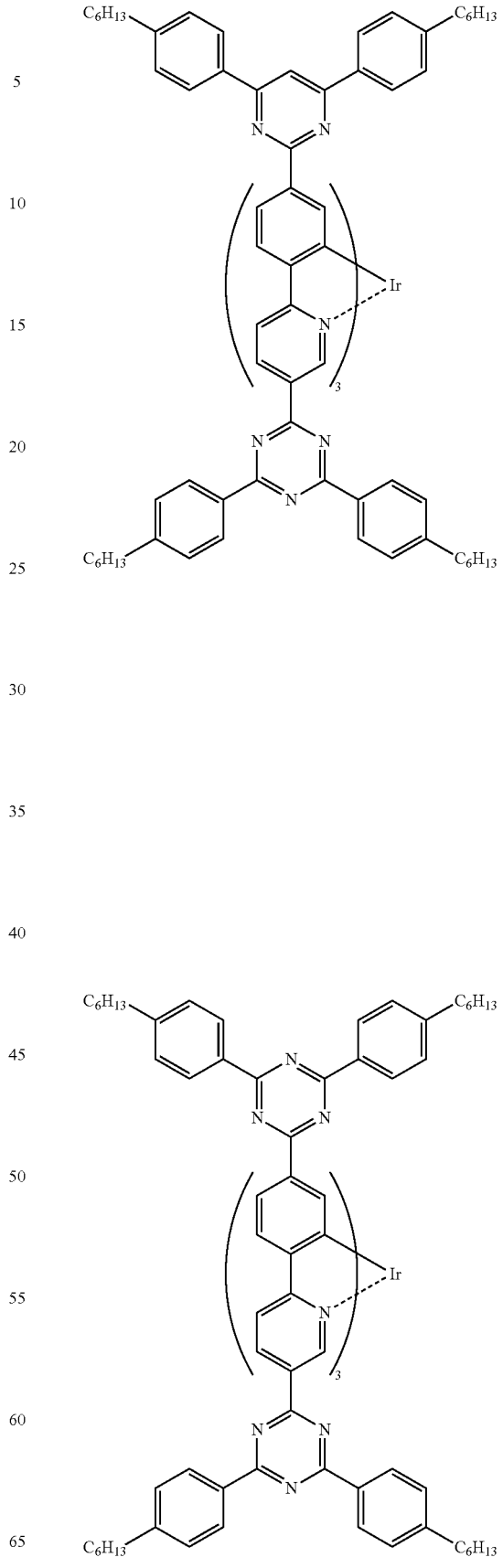

33
-continued
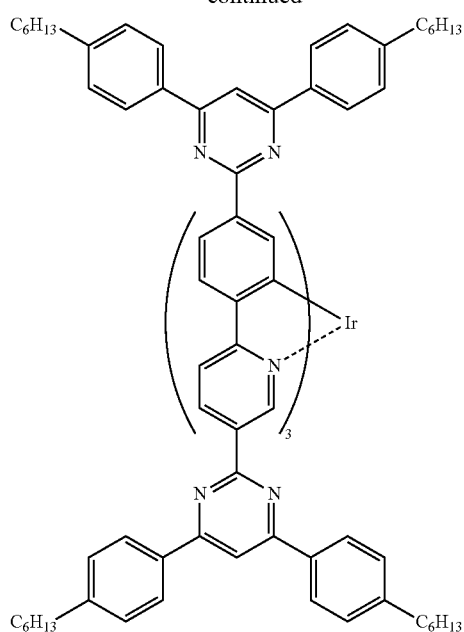
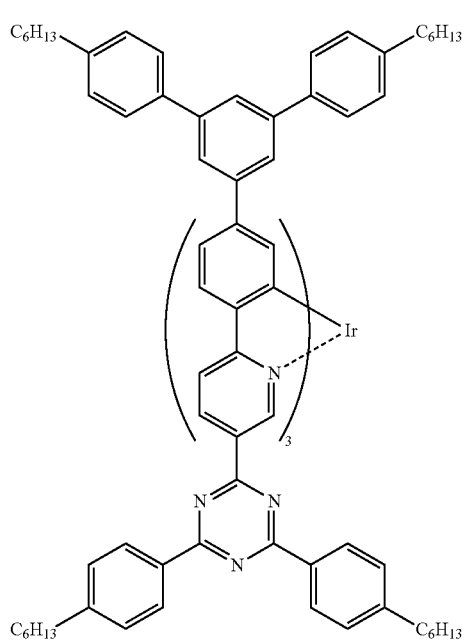
34
-continued
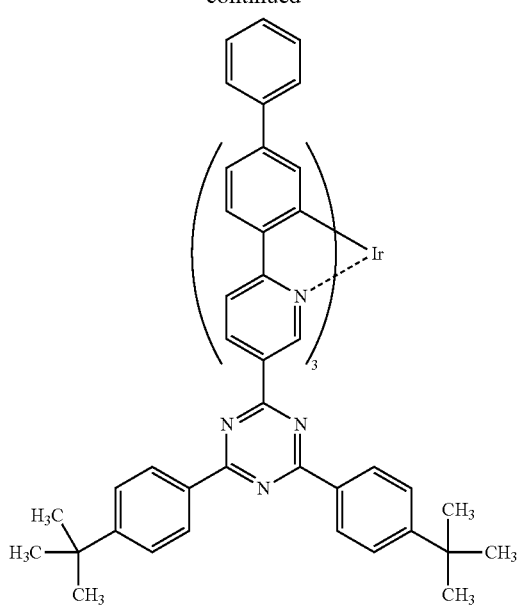
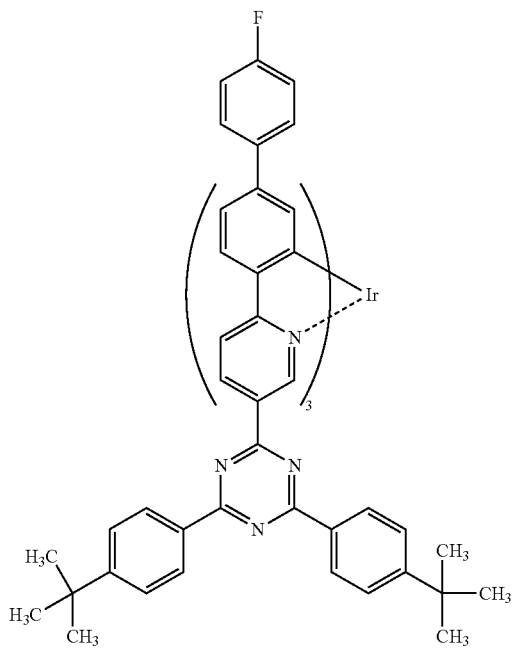

35
-continued
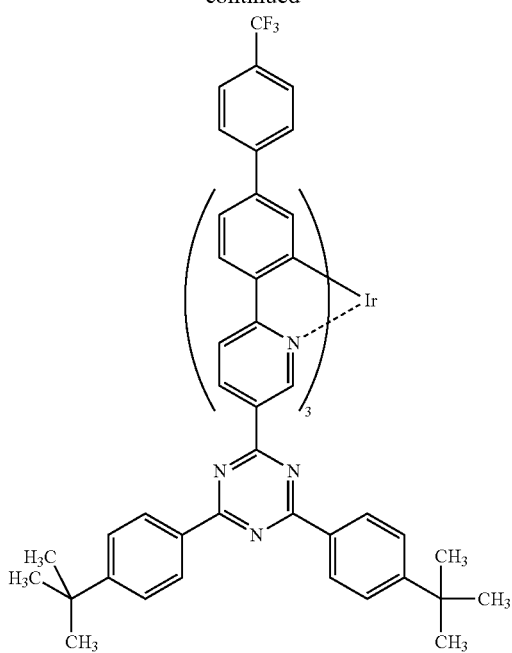
36
-continued
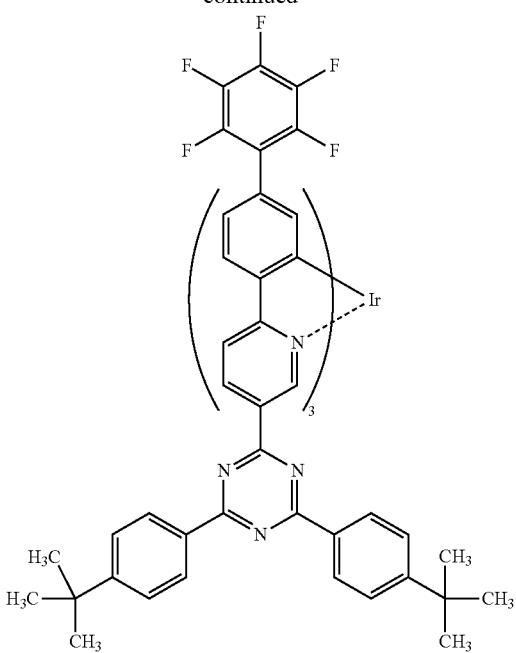
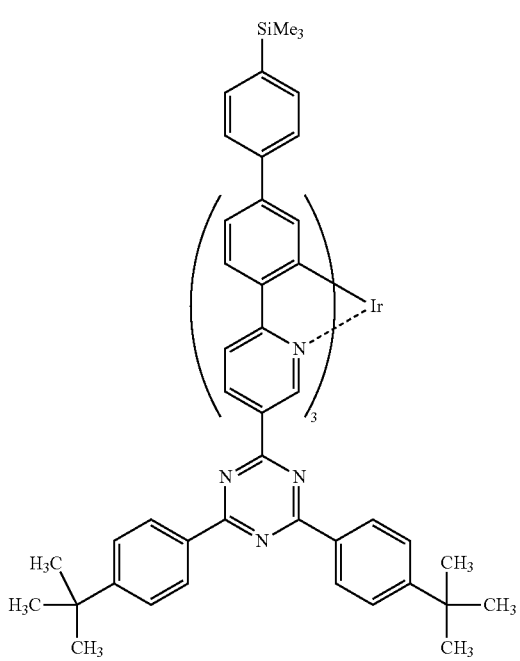
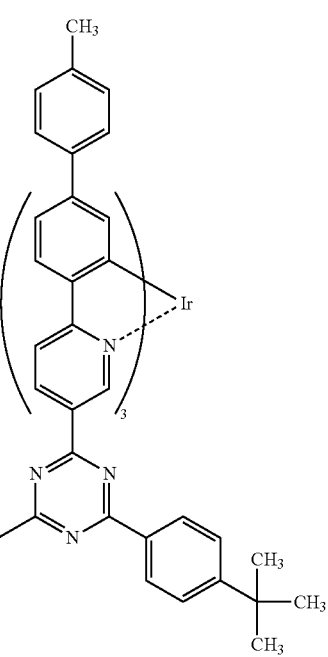

37
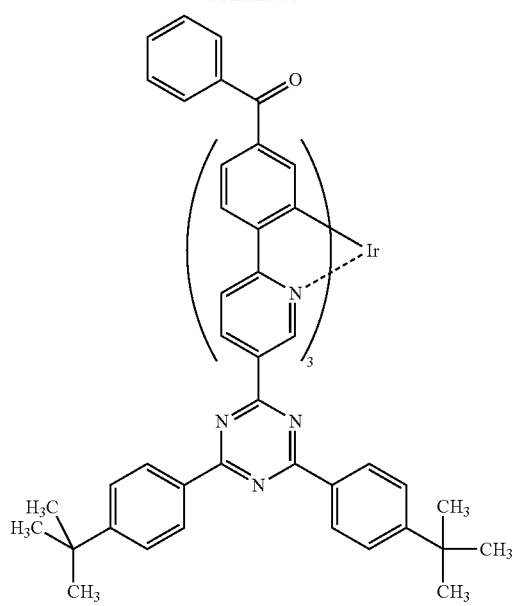
38
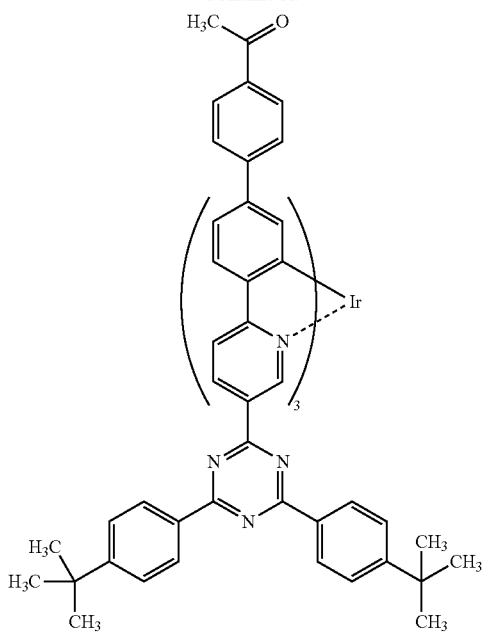
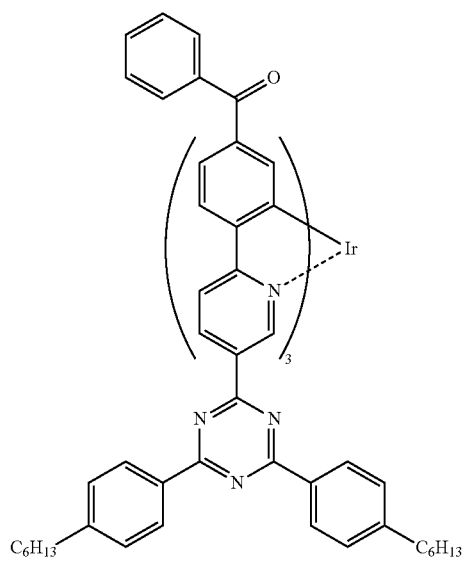
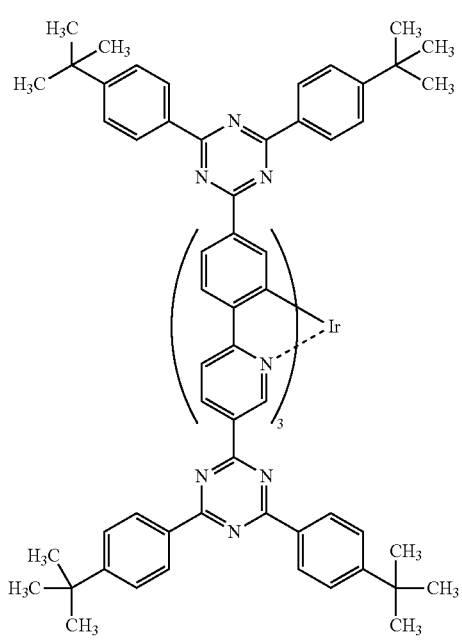

39
-continued
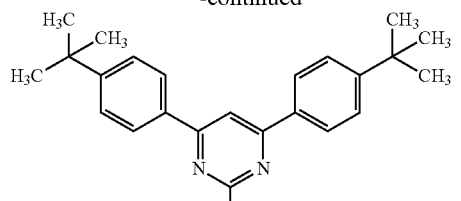
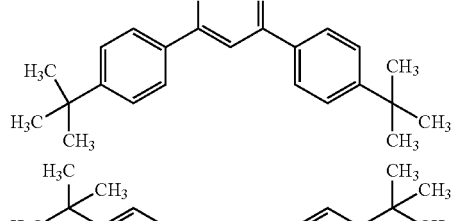
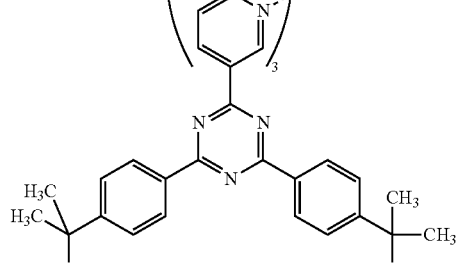
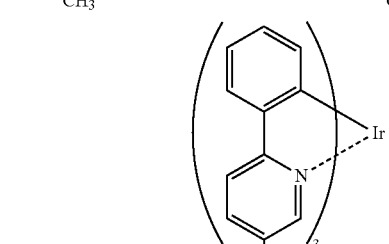
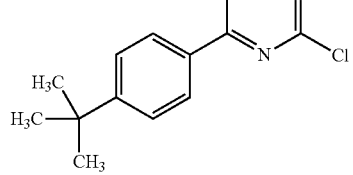
40
-continued
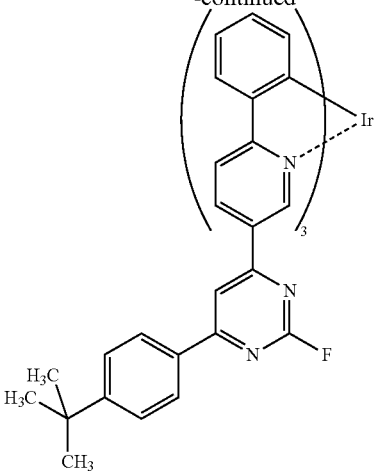
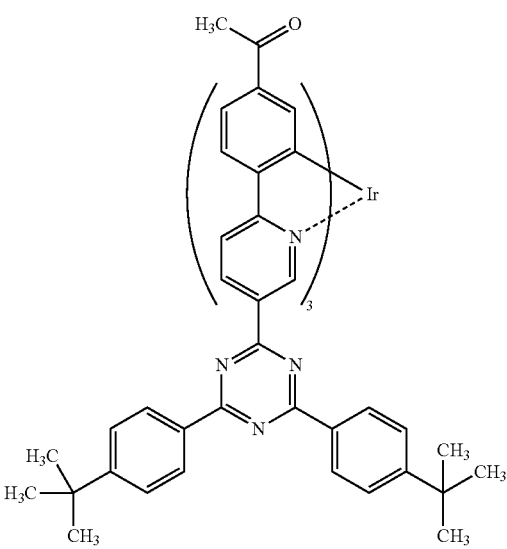
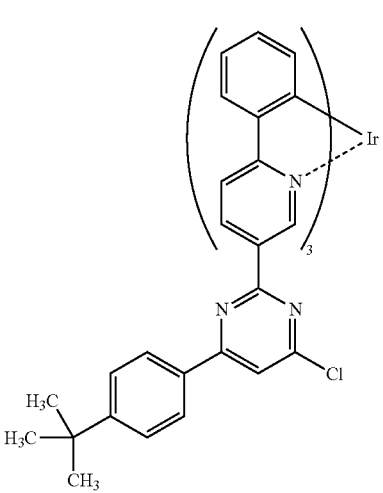

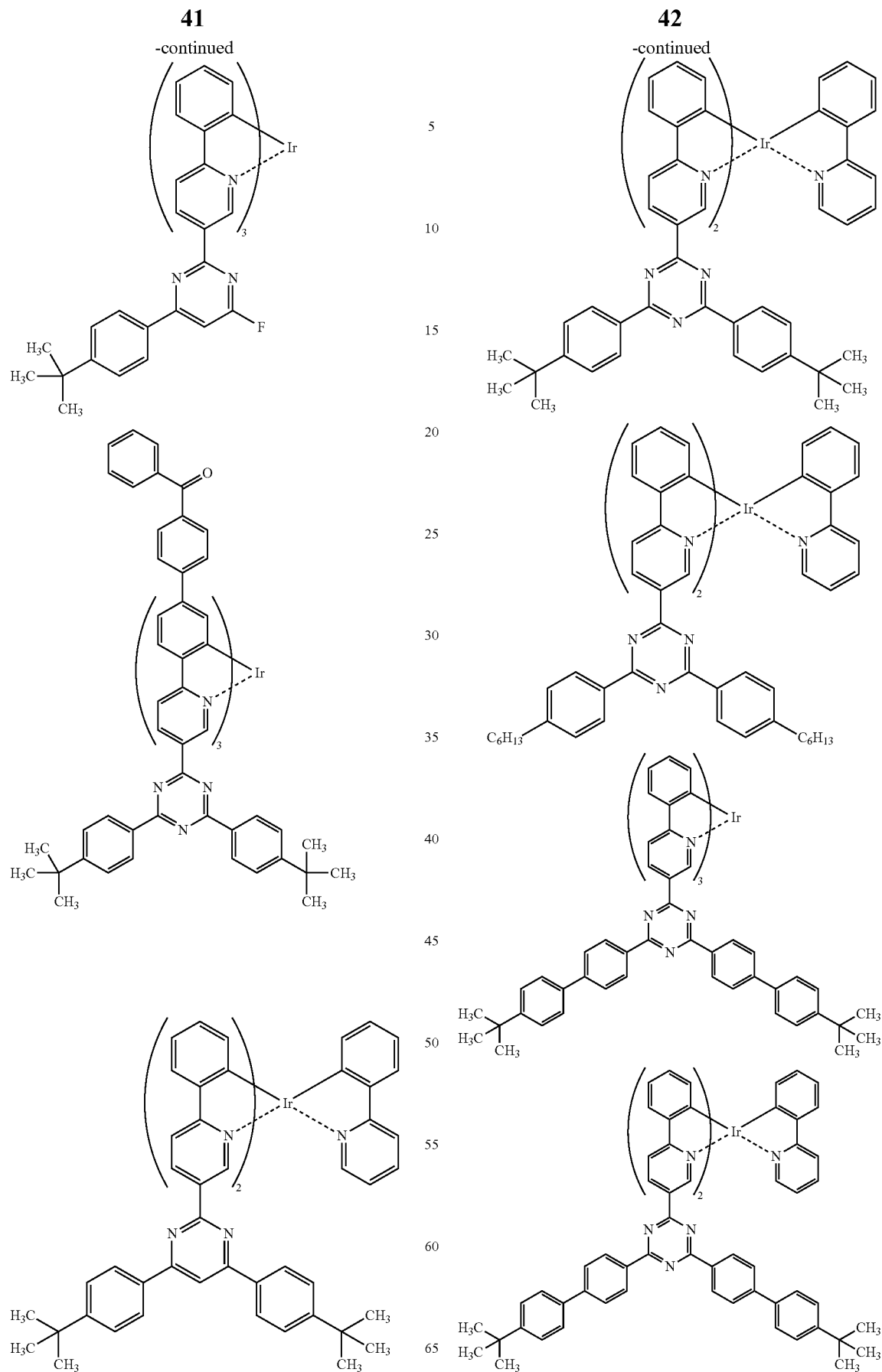

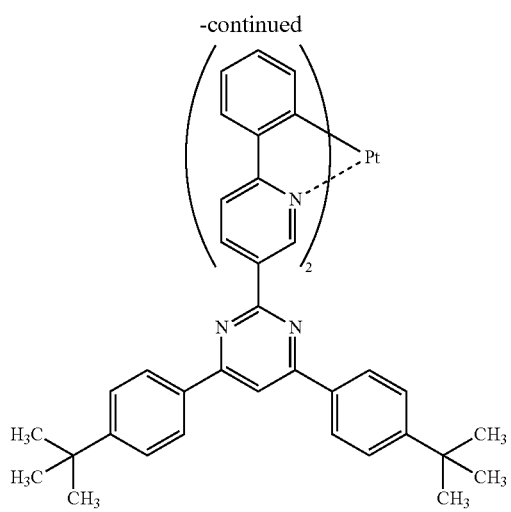
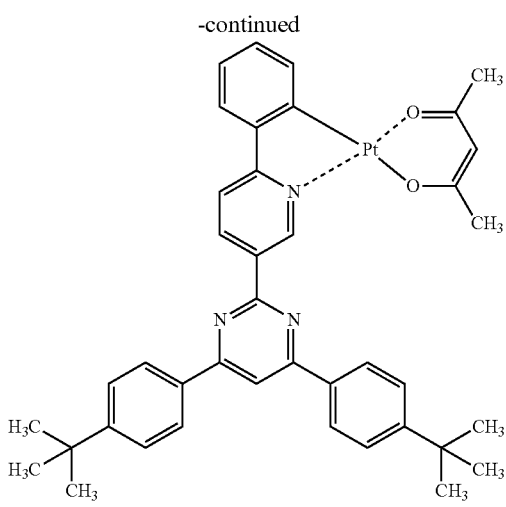
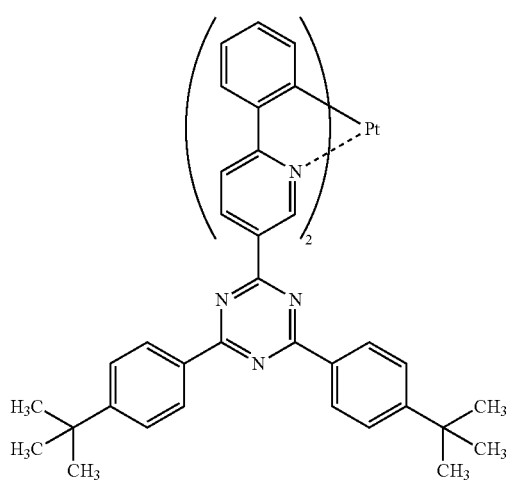
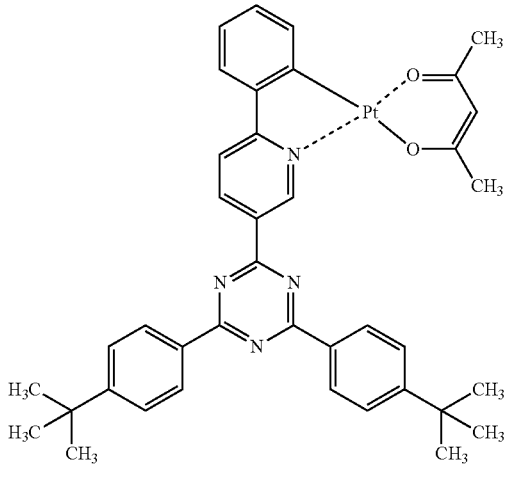
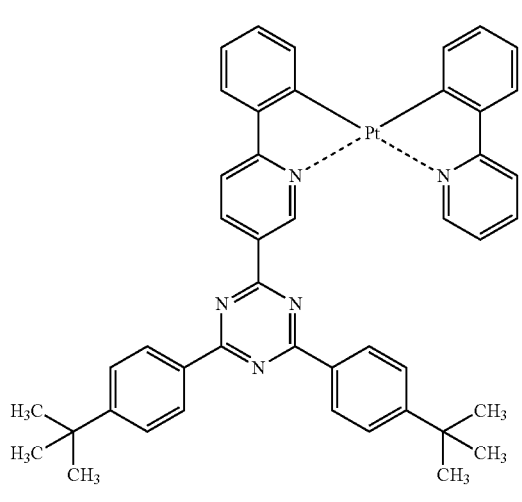
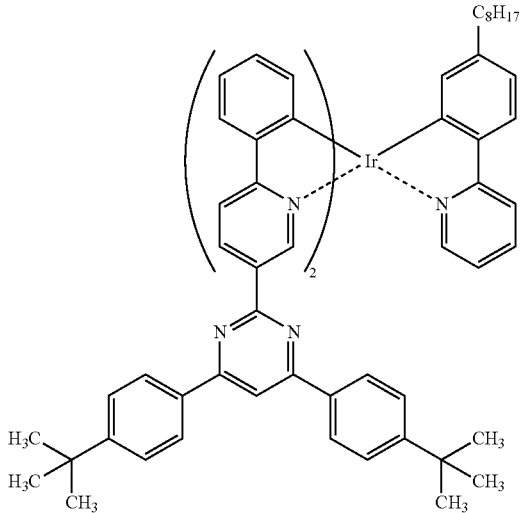

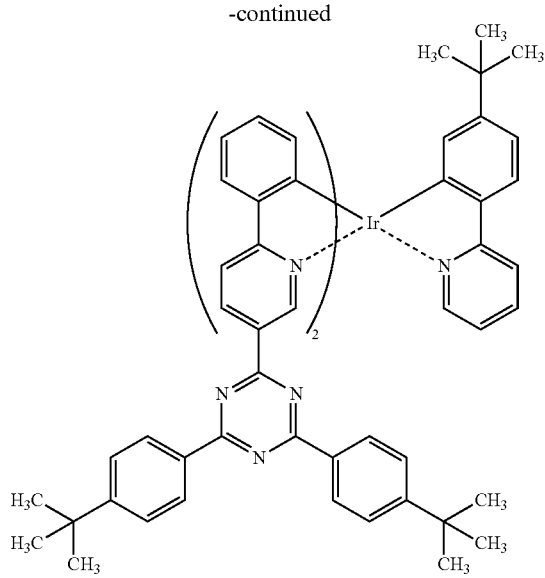

The metal complex of the present invention is preferably a metal complex whose triplet excited state has a short lifetime, which effectively makes forbidden transition allowable, from the viewpoint of stable light emission with high efficiency.

—Method for Producing a Metal Complex—

Next, a method for producing the metal complex will be described.

The metal complex can be synthesized by reacting a compound serving as a ligand with a metallic compound in a solution, for example. A base, a silver halide compound, and the like may exist in the reaction system when necessary. The metal complex can also be synthesized by coupling reaction of a metal complex having a 2-phenylpyridine derivative in a ligand with a heterocyclic aromatic compound.

Examples of a method for forming a complex (namely, a method for reacting a compound serving as a ligand with a metallic compound in a solution) include methods described in J. Am. Chem. Soc. 1984, 106, 6647; Inorg. Chem. 1991, 30, 1685; Inorg. Chem. 1994, 33, 545; Inorg. Chem. 2001, 40, 1704; Chem. Lett., 2003, 32, 252 and the like in the cases of an iridium complex; methods described in Inorg. Chem., 1984, 23, 4249; Chem. Mater. 1999, 11, 3709; Organometallics, 1999, 18, 1801 and the like in the cases of a platinum complex; and a method described in J. Org. Chem., 1987, 52, 73 and the like in the cases of a palladium complex.

With respect to a reaction temperature for forming a complex, usually, the reaction can be performed between the melting point of solvent and the boiling point thereof, and a temperature of −78° C. to the boiling point of the solvent is preferable. The reaction time is usually approximately from 30 minutes to 30 hours. However, in the case where a microwave reactor is used in the complex forming reaction, the reaction can also be performed at a temperature of not less than the boiling point of the solvent. The reaction time is usually approximately from a few minutes to a few hours.

The compound serving as the ligand can be synthesized by Suzuki coupling of a 2-phenylpyridine derivative and a heterocyclic aromatic compound, Grignard coupling thereof, and Stille coupling thereof, for example. By dissolving the raw material compounds in an organic solvent when necessary and reacting the raw material compounds at a temperature of not less than the melting point of the organic solvent and not more than the boiling point thereof using an alkali or an appropriate catalyst, for example, the compound serving as the ligand can be synthesized. For this synthesis, the following methods can be used: "Organic Syntheses," Collective Volume VI, pp. 407-411, John Wiley & Sons, Inc., 1988; Chem. Rev., vol. 106, p. 2651 (2006); Chem. Rev., vol. 102, p. 1359 (2002); Chem. Rev., vol. 95, p. 2457 (1995); and J. Organomet. Chem., vol. 576, p. 147 (1999), for example.

The heterocyclic aromatic compound can be synthesized by the method described in: "HOUBEN-WEYL METHODS OF ORGANIC CHEMISTRY 4$^{TH}$ EDITION," vol. E9b, p. 1, GEORG THIEME VERLAG STUTTGART; HOUBEN-WEYL METHODS OF ORGANIC CHEMISTRY 4$^{TH}$ EDITION, vol. E9c, p. 667, GEORG THIEME VERLAG STUTTGART, and the like.

As a catalyst used for the coupling reaction, a palladium catalyst is preferable. Examples of the palladium catalyst include palladium acetate, bis(triphenylphosphine)palladium (II) dichloride, tetrakis(triphenylphosphine)palladium(0), [1,1'-bis(diphenylphosphino)ferrocene]dichloropalladium (II), and tris(dibenzylideneacetone)dipalladium (O). Tetrakis(triphenylphosphine)palladium(0), [1,1'-bis(diphenylphosphino)ferrocene]dichloropalladium(II), and tris(dibenzylideneacetone)dipalladium(O) are preferable. A phosphorus ligand may be made to exist when necessary. Examples of the phosphorus ligand include triphenyl phosphine, tri(o-tolyl)phosphine, tri(t-butyl)phosphine, tri-cyclohexylphosphine, and 1,1'-bis(diphenylphosphino)ferrocene.

Examples of the compound serving as the ligand include compounds shown below:

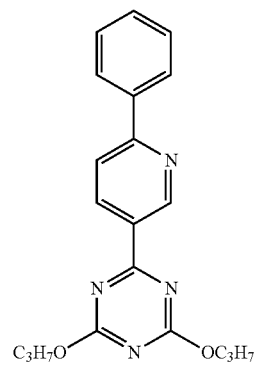

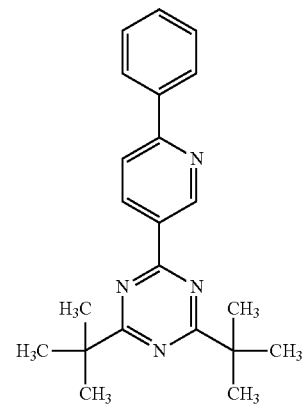

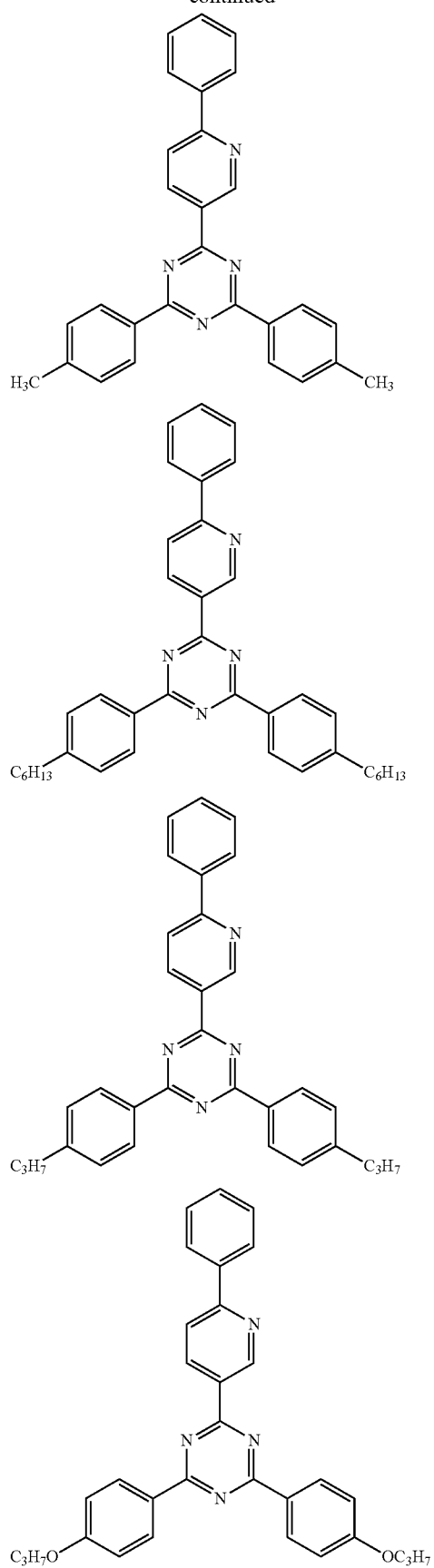
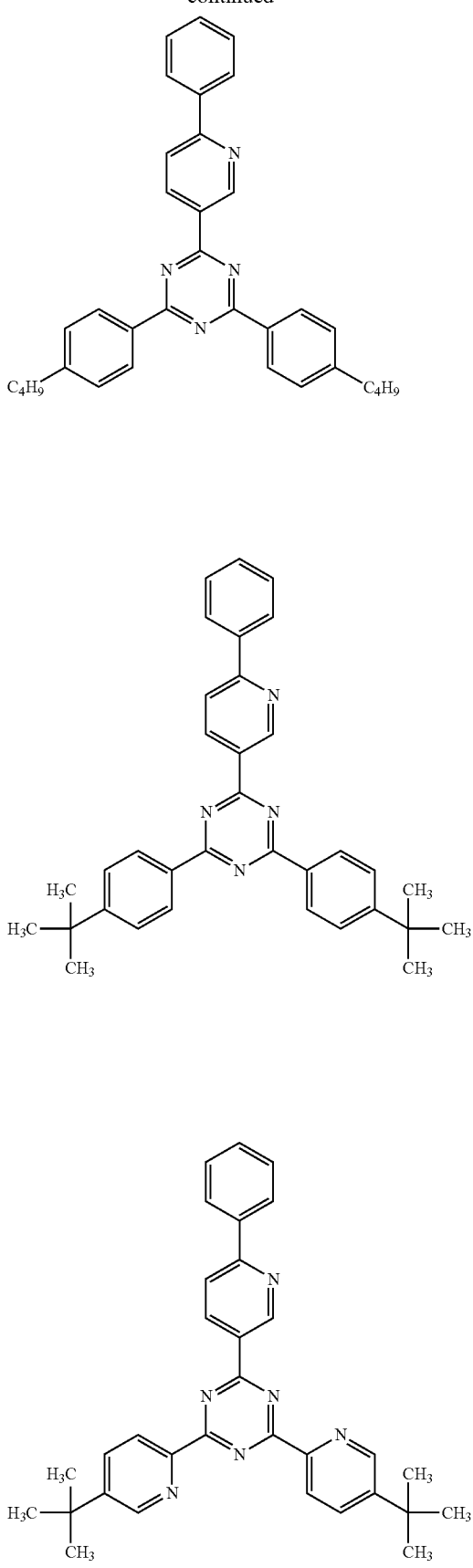

49
-continued
50
-continued
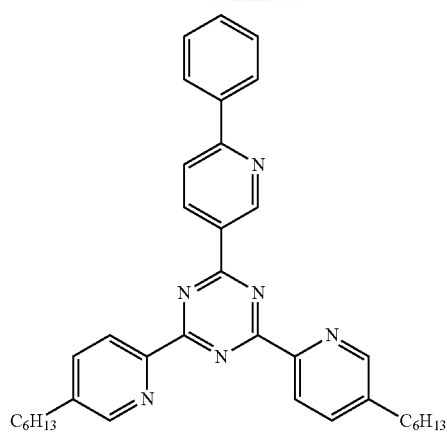
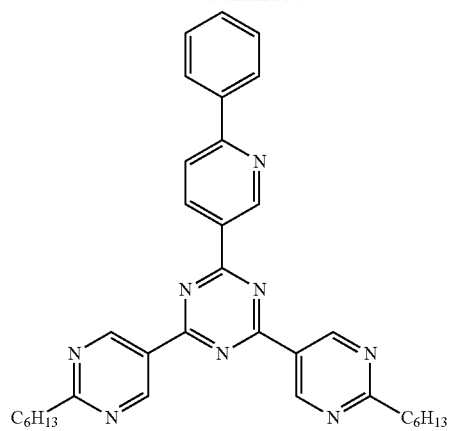
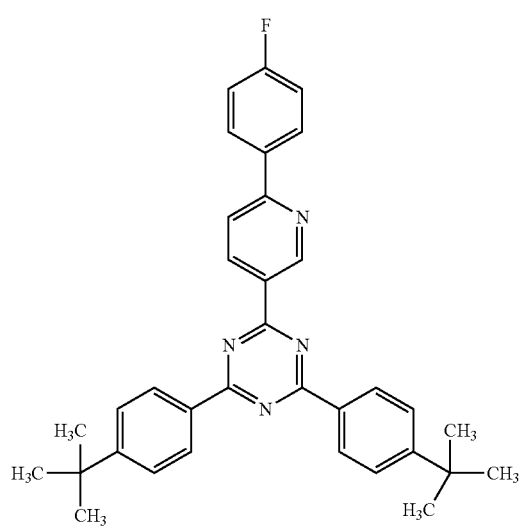
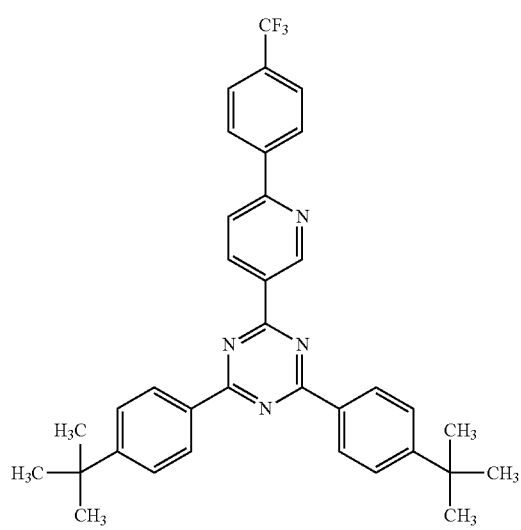

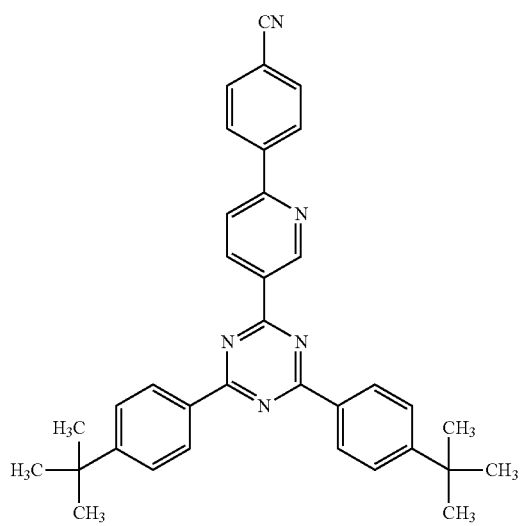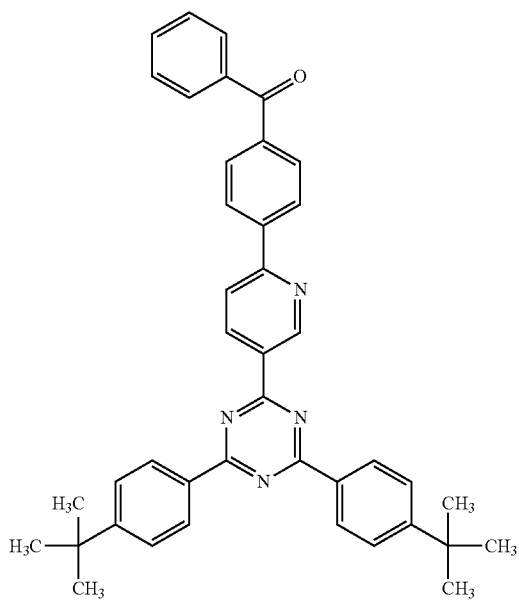

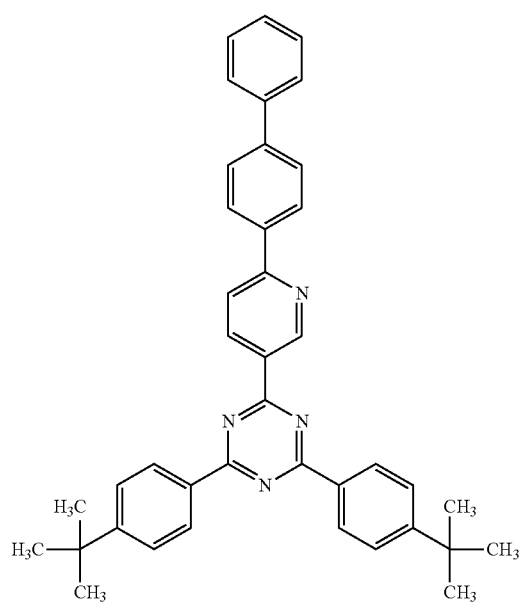
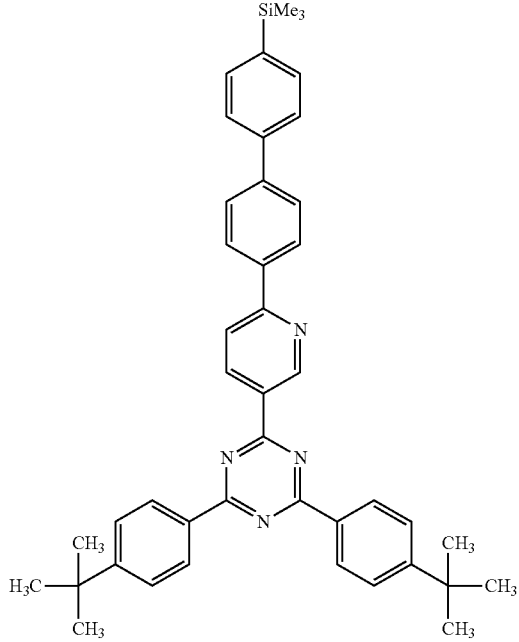
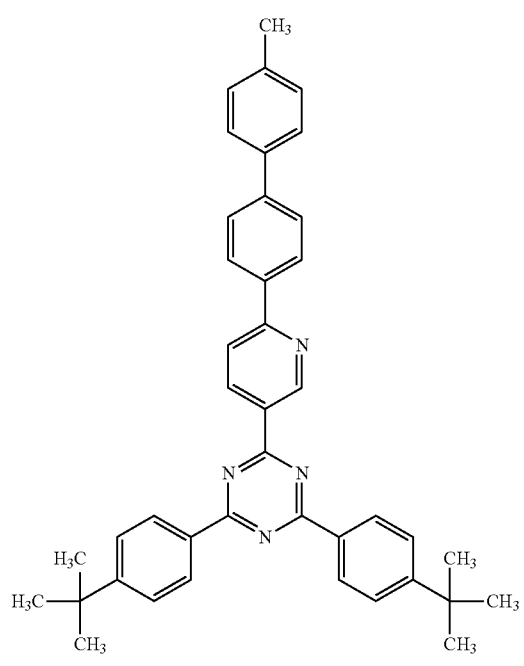
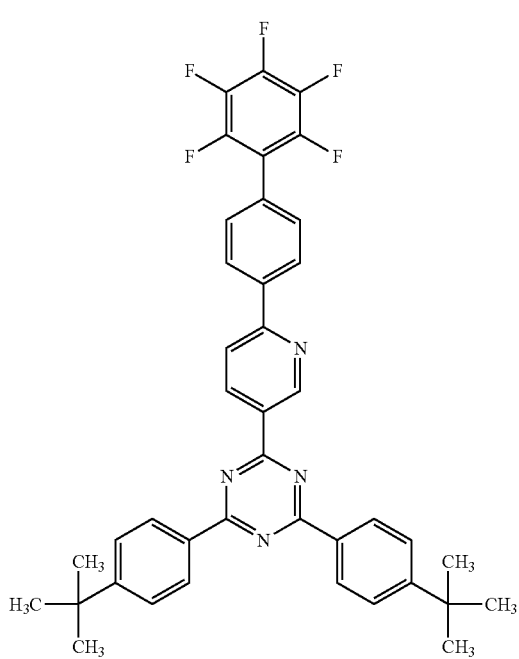

55
-continued
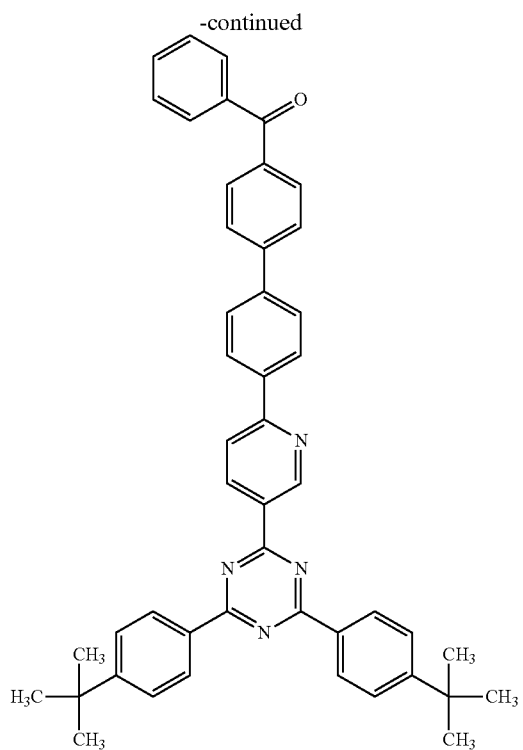
56
-continued
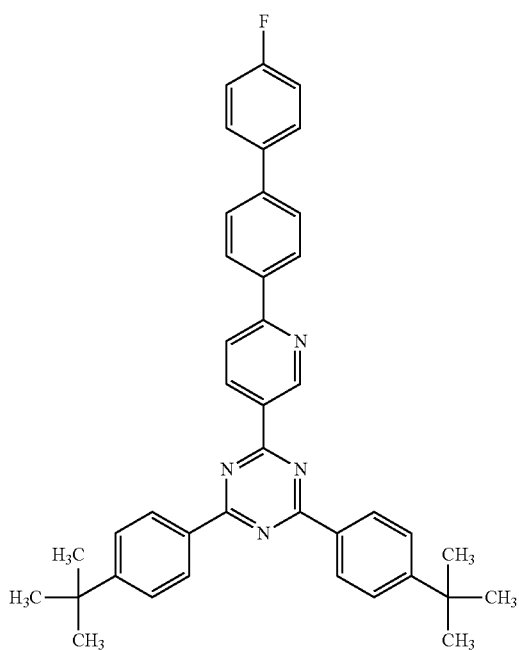
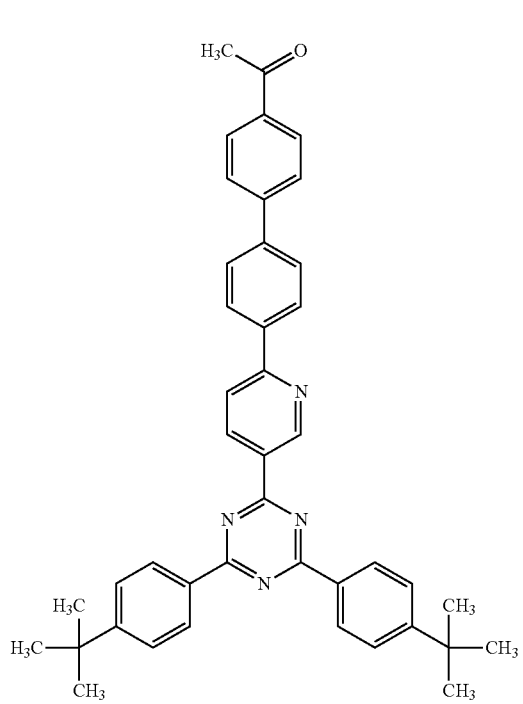
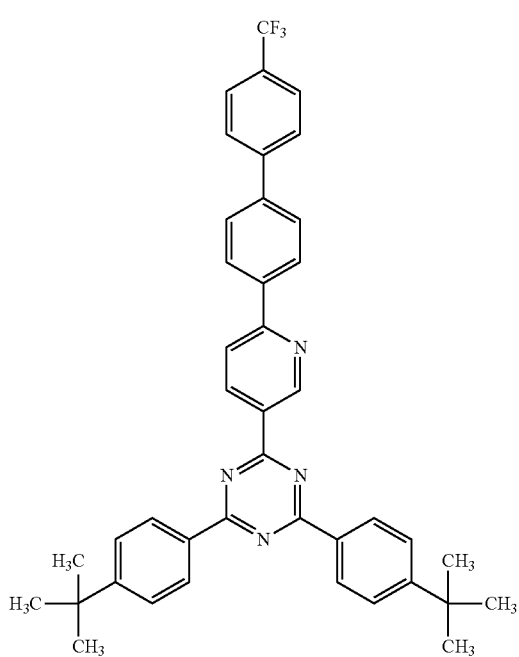

57
-continued
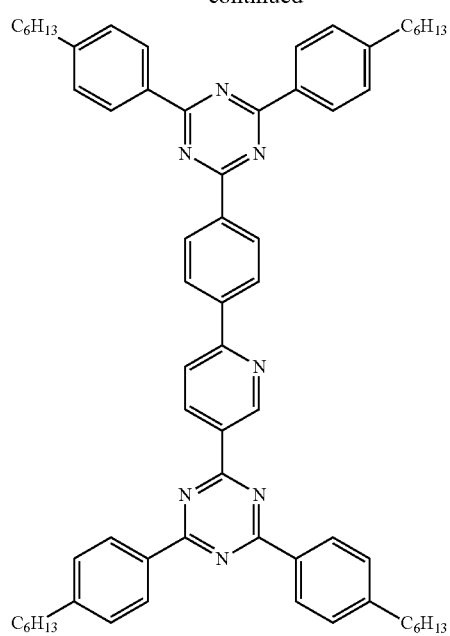
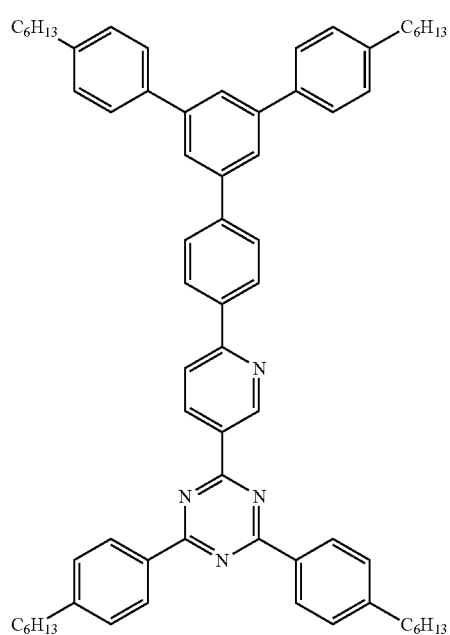
58
-continued
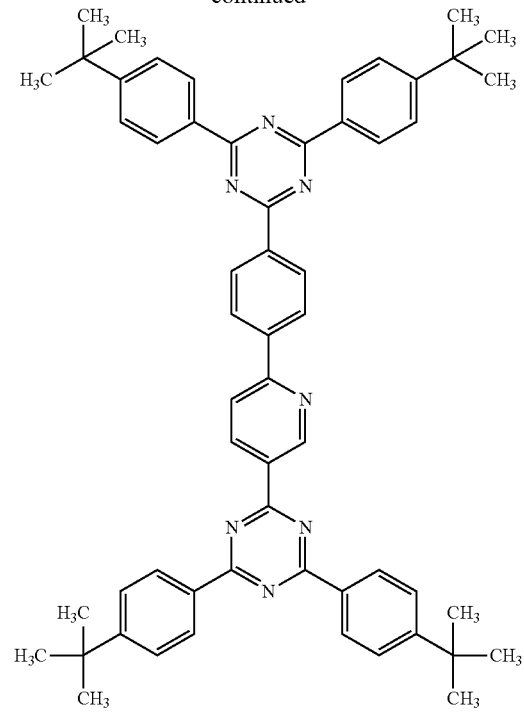
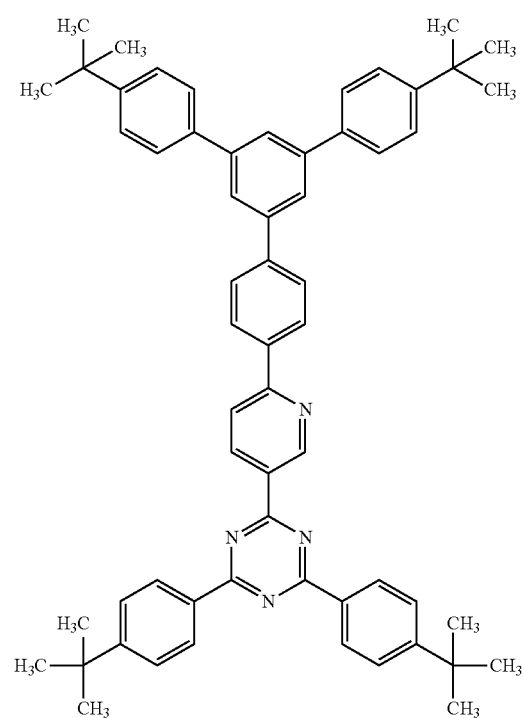 [SMILES: CC(C)(C)c1ccc(-c2cc(-c3ccc(C(C)(C)C)cc3)nc(-c3ccc(-c4ccc(-c5nc(-c6ccc(C(C)(C)C)cc6)cc(-c6ccc(C(C)(C)C)cc6)n5)cn4)cc3)n2)cc1]

59
-continued
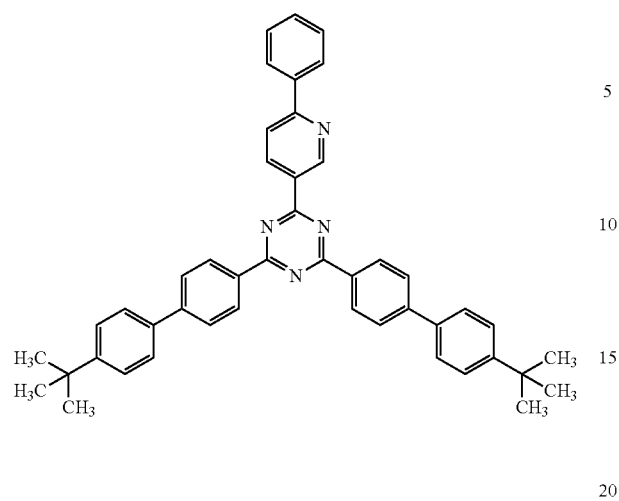
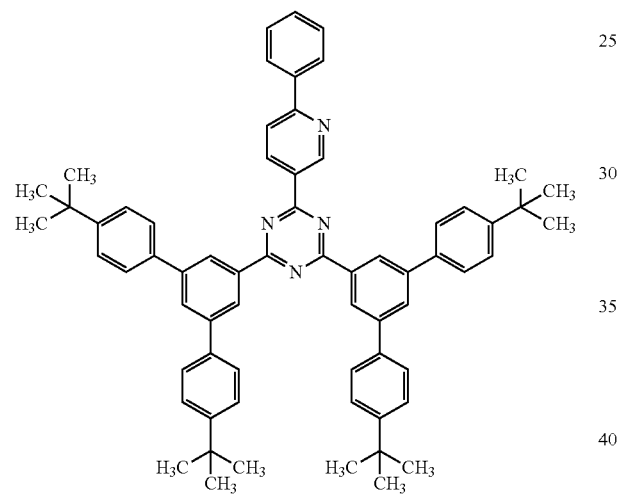
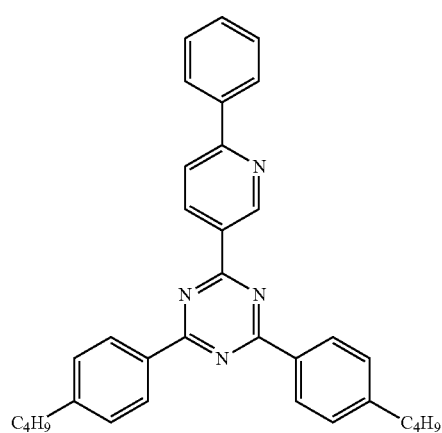
60
-continued
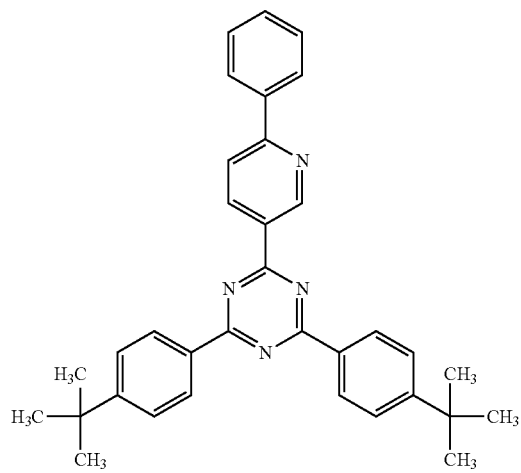
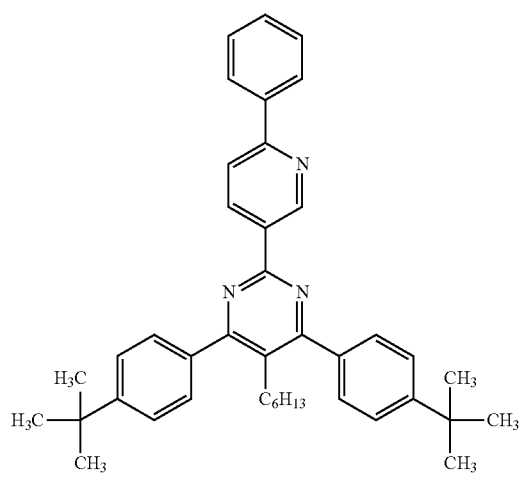
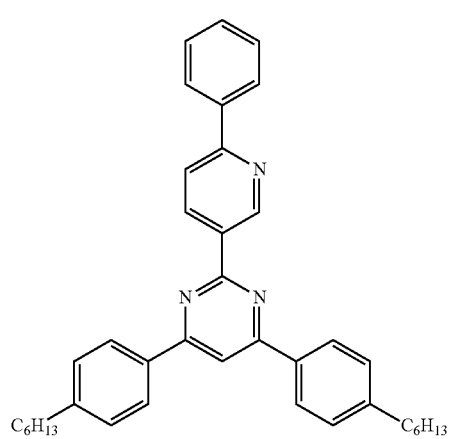

-continued

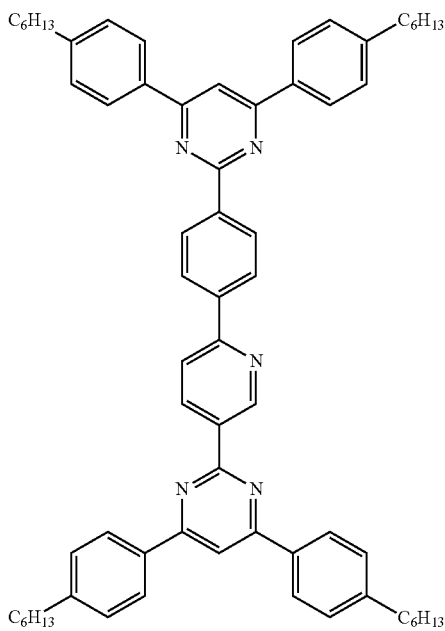

-continued

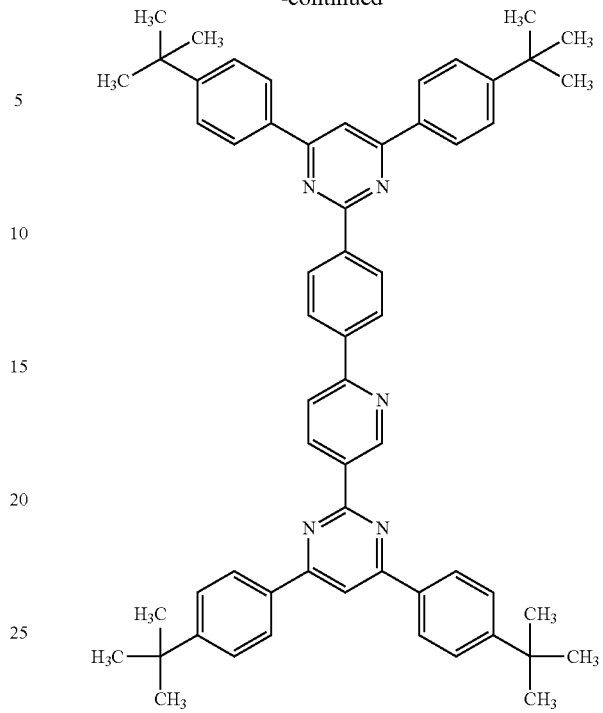

As the compound serving as the ligand, a compound represented by the formula (11a) or the following formula (11b) is preferable from the viewpoint of stability of the metal complex, easiness of synthesis, and luminous efficiency, and the compound represented by the formula (11a) is more preferable.

The aryl group and monovalent heterocyclic group represented by A are the same as those described and exemplified as R mentioned above in the formulas (11a) and (11b).

The metal complex can be synthesized according to the following scheme, for example:

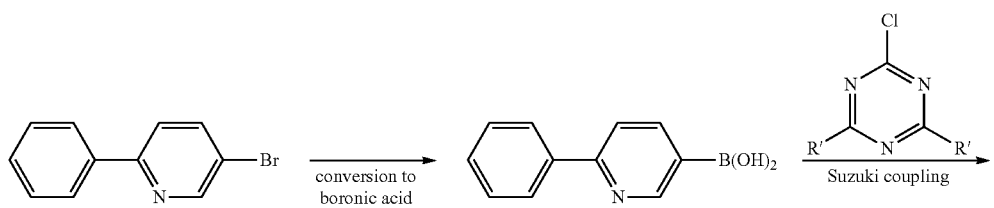

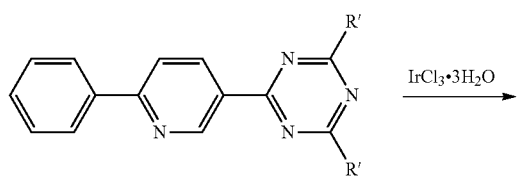

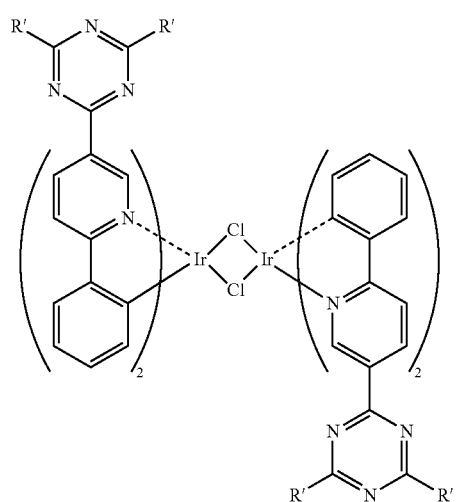 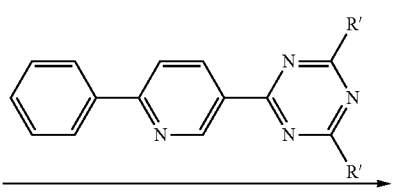 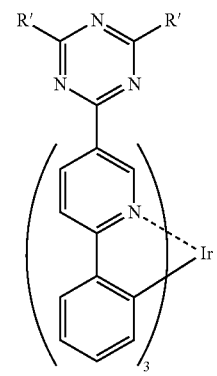

(wherein R' is as defined above.)

Identification and analysis of the obtained metal complex can be performed by elemental analysis, NMR analysis, and MS analysis.

It is also preferable that the metal complex of the present invention be produced by a method comprising performing a coupling reaction of the compound represented by the following formula (8) with a heterocyclic aromatic compound having a halogen atom or an alkylsulfonate group.

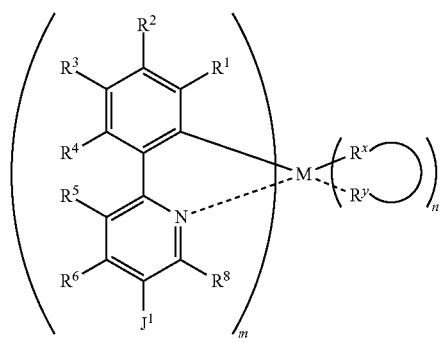

(8)

(wherein M, $R^1$, $R^2$, $R^3$, $R^4$, $R^5$, $R^6$, $R^8$, m, n, $R^x$, and $R^y$ are as defined above; $J^1$ is a group represented by the following formulas (9-1) to (9-6):

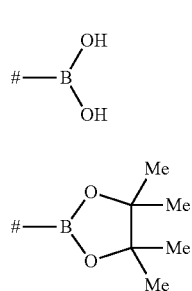

(9-1)

(9-2)

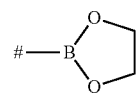
(9-3)

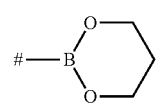
(9-4)

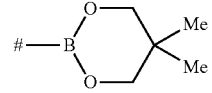
(9-5)

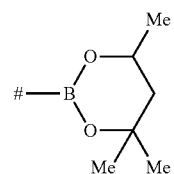
(9-6)

\# represents a bond.)

The compound represented by the formula (8) can be synthesized by forming a compound represented by the following formula (10) into a boric acid compound or a boric acid ester compound, for example:

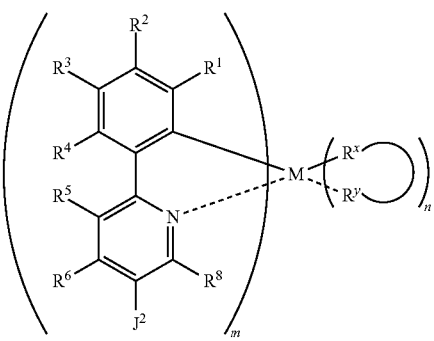

(10)

(wherein M, $R^1$, $R^2$, $R^3$, $R^4$, $R^5$, $R^6$, $R^8$, m, n, $R^x$, and $R^y$ are as defined above; $J^2$ represents a halogen atom.)

The metal complex of the present invention can be synthesized by Suzuki coupling of a compound represented by the formula (10) and a heterocyclic aromatic compound, Grignard coupling thereof, Stille coupling thereof, and the like.

—Divalent Group Represented by the Formulas (3-1) to (3-5)—

In the formulas (3-1) to (3-5), the group and atoms represented by $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ are the same as those described and exemplified as the groups and atoms represented by R. In the formulas (3-1) and (3-2), from the viewpoint of easiness to synthesize the polymer compound according to the present invention and high luminous efficiency, Y is preferably —C($R^9$)($R^{10}$)—, —O—C($R^{17}$)($R^{18}$)—, —O—, and —S—, and more preferably —C($R^9$)($R^{10}$)—.

Examples of the divalent group represented by the formula (3-1) include groups represented by the following formulas:

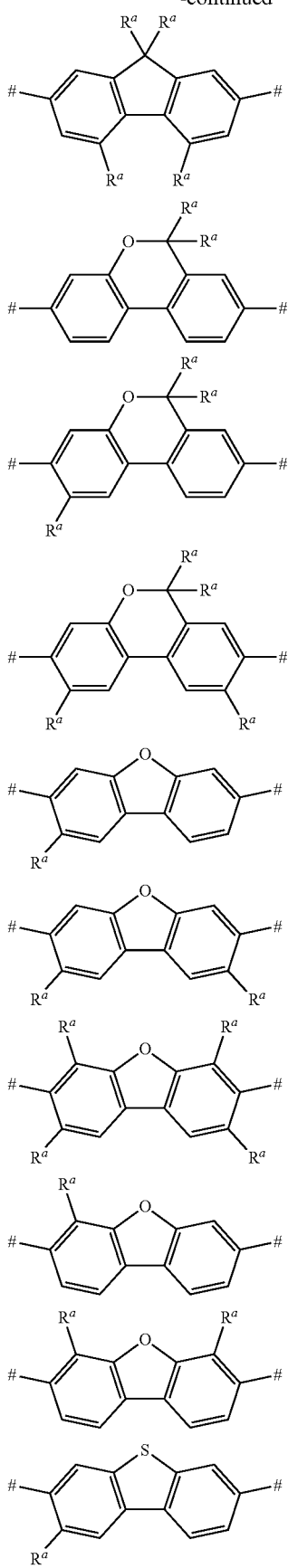

-continued

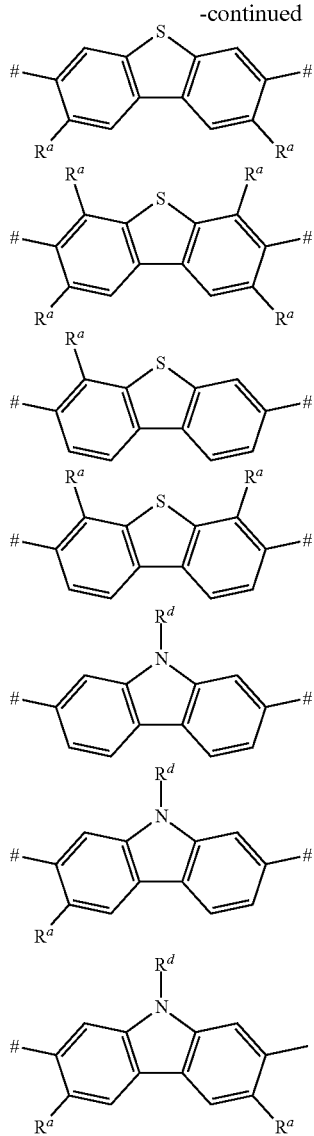

(wherein # represents a bond; $R^a$ represents an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; a plurality of $R^a$ may be the same or different; $R^d$ represents an alkyl group, an aryl group, an arylalkyl group, an arylalkenyl group, an arylalkynyl group, or a monovalent heterocyclic group.)

The alkyl group, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the silyloxy group, the substituted silyloxy group, the monovalent heterocyclic group, and the halogen atom represented by $R^a$ are the same as those described and exemplified as the groups and atoms represented by R.

The alkyl group, the aryl group, the arylalkyl group, the arylalkenyl group, the arylalkynyl group, or the monovalent heterocyclic group represented by $R^d$ are the same as those described and exemplified as the groups represented by R.

Examples of the divalent group represented by the formula (3-2) include groups represented by the following formulas:

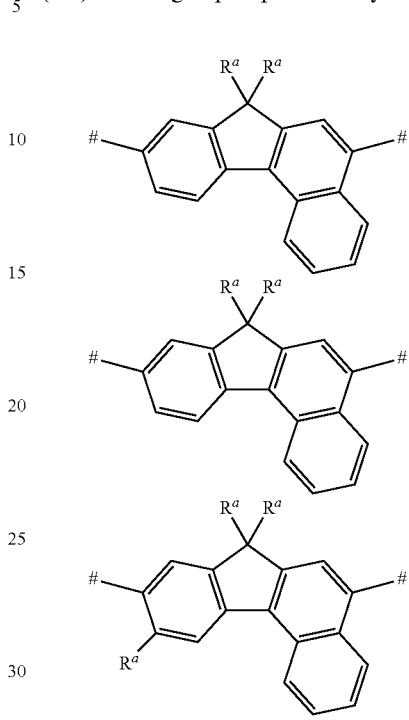

(wherein # and $R^a$ are as defined above.)

Examples of the divalent group represented by the formula (3-3) include groups represented by the following formulas:

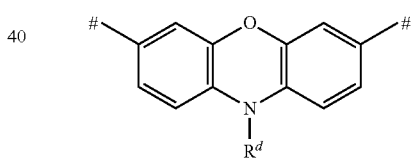

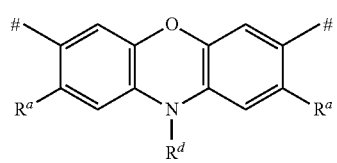

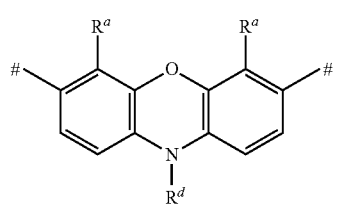

(wherein #, $R^a$, and $R^d$ are as defined above.)

Examples of the divalent group represented by the formula (3-4) include groups represented by the following formulas:

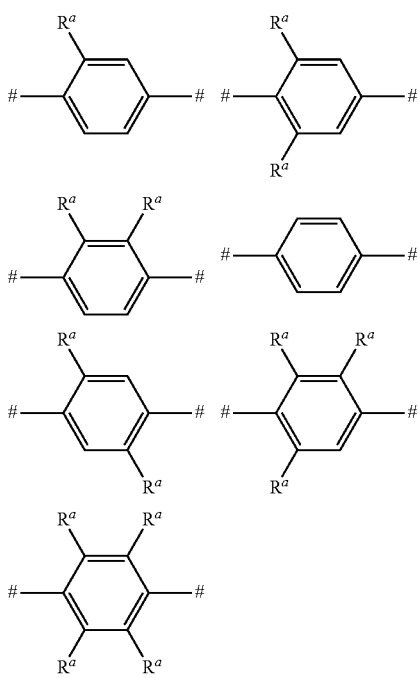

(wherein # and $R^a$ are as defined above.)

Examples of the divalent group represented by the formula (3-5) include groups represented by the following formulas:

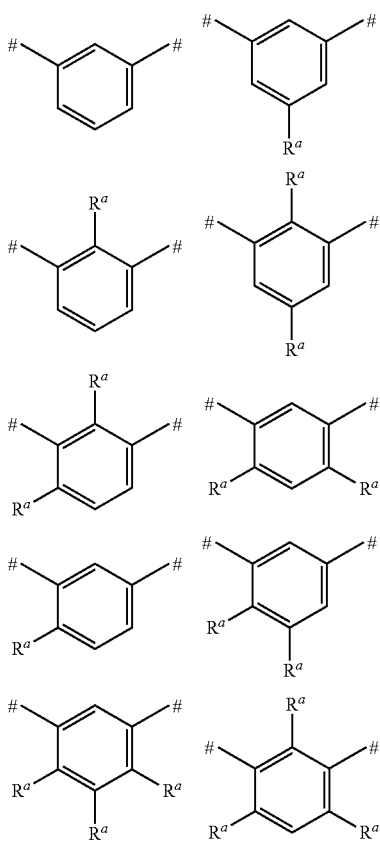

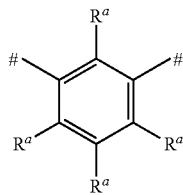

(wherein # and $R^a$ are as defined above.)

Of the divalent groups represented by the formulas (3-1) to (3-5), the divalent groups represented by the formula (3-1) are preferable from the viewpoint of lifetime and characteristics of the device.

—Other Groups—

In addition to the residue of the metal complex represented by the formula (1) and the divalent groups represented by the formulas (3-1) to (3-5), the polymer compound according to the present invention may further contain a group represented by the following formula (4):

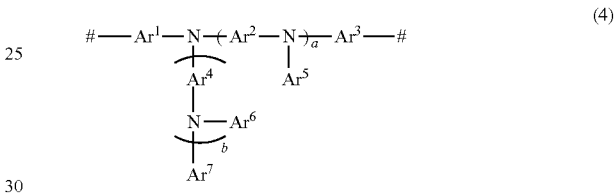

(4)

(wherein $Ar^1$, $Ar^2$, $Ar^3$, and $Ar^4$ each independently represent an arylene group or a divalent heterocyclic group; $Ar^5$, $Ar^6$, and $Ar^7$ each independently represent an aryl group or a monovalent heterocyclic group; $Ar^1$, $Ar^2$, $Ar^3$, $Ar^4$, $Ar^5$, $Ar^6$, and $Ar^7$ may have a substituent; a and b each independently represent 0 or 1, and $0 \leq a+b \leq 1$; # represents a bond.)

In the formula (4), the arylene group represented by $Ar^1$, $Ar^2$, $Ar^3$, and $Ar^4$ is an atomic group in which two hydrogen atoms are removed from an aromatic hydrocarbon. The arylene group also includes those having a condensed ring, and those in which two or more independent benzene rings or two or more condensed rings are bonded directly or through a vinylene group or the like. The arylene group may have a substituent. The number of carbon atoms of a portion other than the substituent in the arylene group is usually 6 to 60, and preferably 6 to 20. The total number of carbon atoms of the arylene group containing the substituent is usually 6 to 100.

In the formula (4), the divalent heterocyclic group represented by $Ar^1$, $Ar^2$, $Ar^3$, and $Ar^4$ is the same as those described and exemplified in the section of the divalent heterocyclic group represented by Ar' mentioned below.

In the formula (4), the aryl group and the monovalent heterocyclic group represented by $Ar^5$, $Ar^6$, and $Ar^7$ are the same as those described and exemplified as the aryl group and the monovalent heterocyclic group represented by R.

In the formula (4), examples of the substituent that the arylene group, the divalent heterocyclic group, the aryl group, and the monovalent heterocyclic group may have include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, a cyano group, and a nitro group. These substituents are the same as those described and exemplified as the substituents that the ligand which forms the metal complex may have.
Examples of the groups represented by the formula (4) include groups represented by the following formulas:
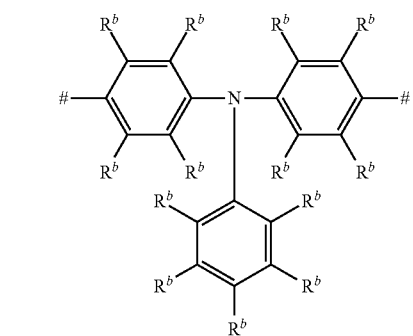
119
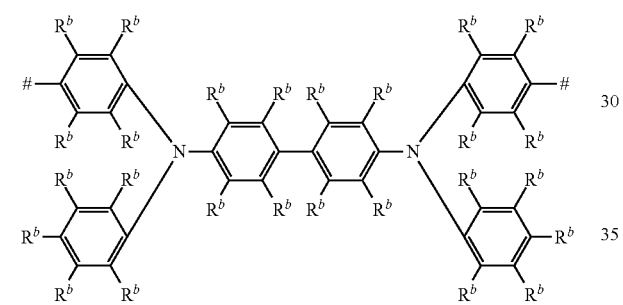
120
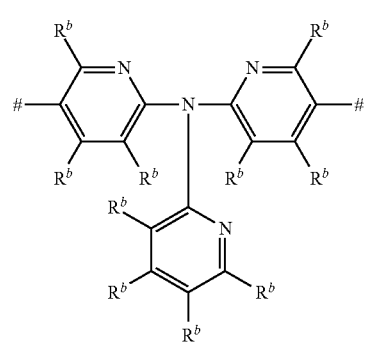
121
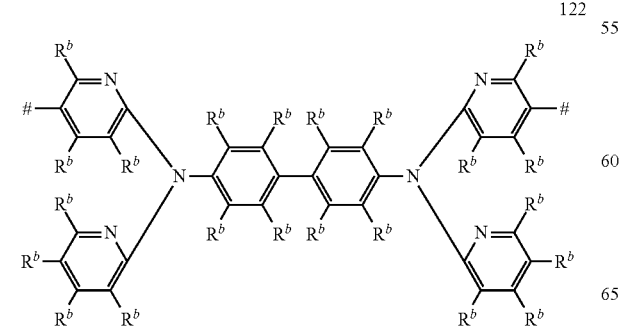
122
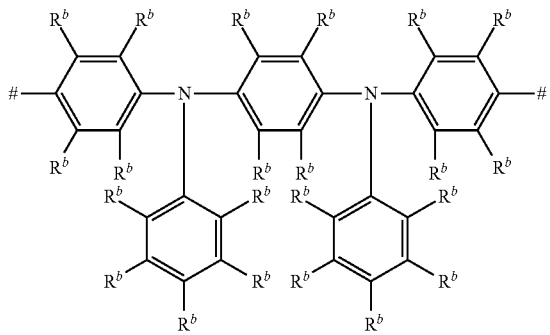
123
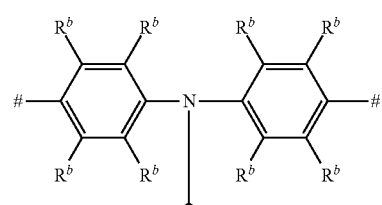
124
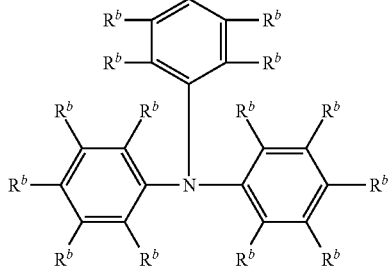
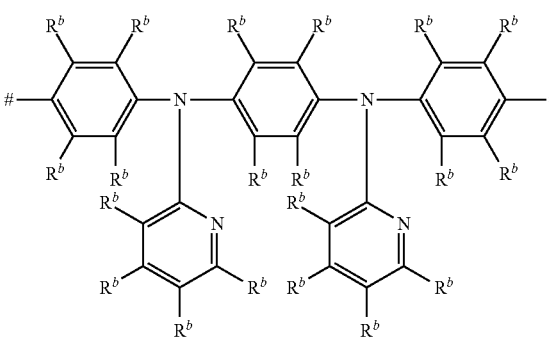
125
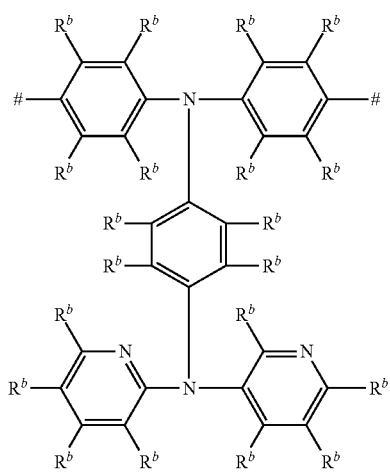
126

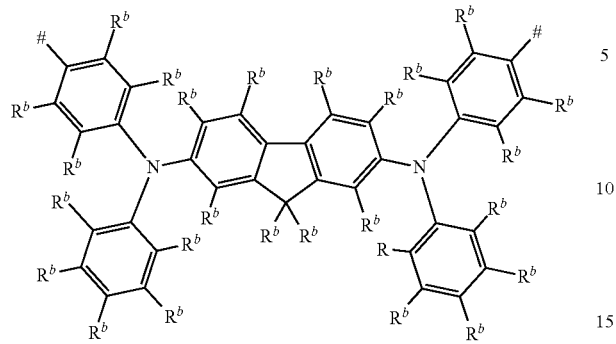

(wherein $R^b$ represents a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group; a hydrogen atom contained in these groups may be substituted by a fluorine atom; a plurality of $R^b$ may be the same or different; # represents a bond.)

—Position of the Residue of the Metal Complex—

Examples of the polymer compound according to the present invention include 1. a polymer compound having a residue of a metal complex in the main chain of the molecular chain;
2. a polymer compound having a residue of a metal complex at a terminal of the molecular chain; and
3. a polymer compound having a residue of a metal complex in the side chain of the molecular chain.

The polymer compound having a residue of a metal complex in the main chain of the molecular chain is represented by one of the following formulas, for example:

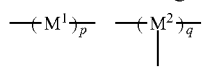

(wherein $M^1$ and $M^2$ represent a residue of a metal complex; p and q represent a degree of polymerization; only in the formula, the solid line represents the molecular chain.)

Examples of $M^1$ include (divalent) residues of a metal complex represented by the following formulas:

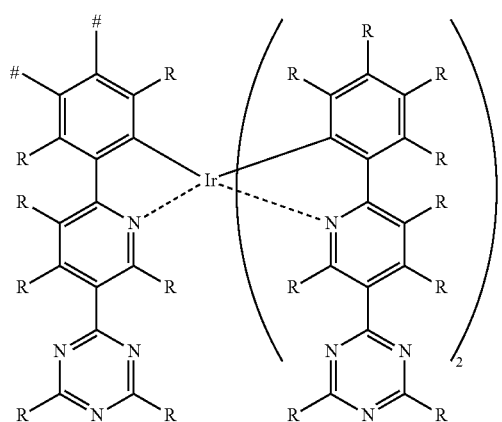

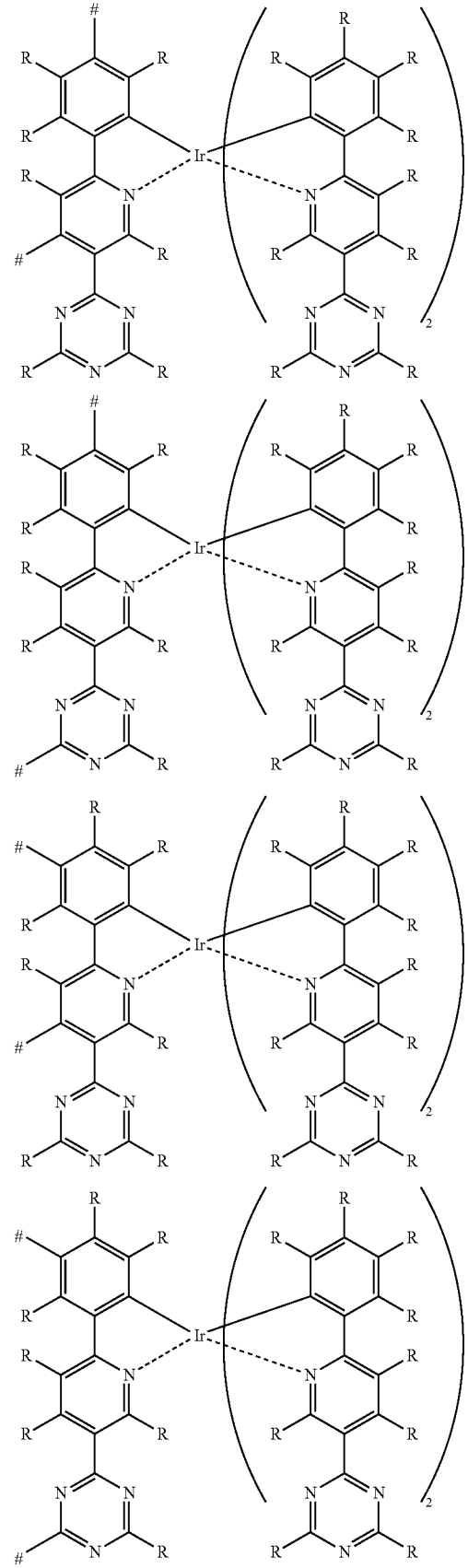

-continued

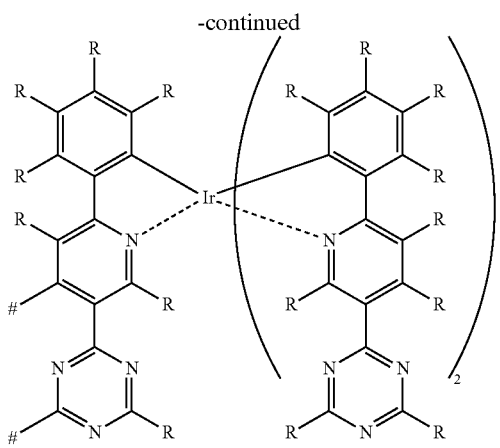

(wherein # and R are as defined above.)

Examples of M² include (trivalent) residues of a metal complex represented by the following formulas:

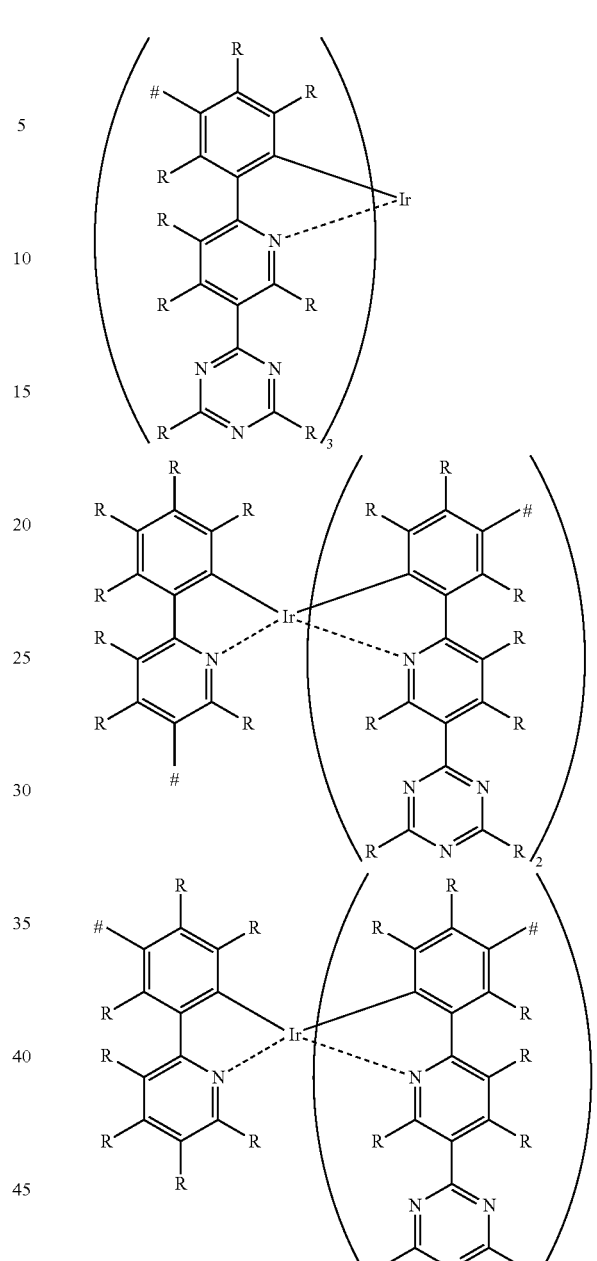

(wherein # and R are as defined above.)

The polymer compound having a residue of a metal complex at a terminal of the molecular chain is represented by the following formulas, for example:

-LM³

M³L-LM³

(wherein M³ represents a residue of a metal complex; only in the formula, the solid line represents the molecular chain; L represents a single bond, —O—, —S—, —C(=O)—, —C(=O)O—, —S(=O)—, —S(=O)₂—, —Si(R⁶⁸)(R⁶⁹)—, N(R⁷⁰)—, —B(R⁷¹)—, —P(R⁷²)—, —P(=O)(R⁷³)—, an alkylene group that may be substituted, an alkenylene group that may be substituted, an alkynylene group that may be substituted, an arylene group that may be substituted, or a divalent heterocyclic group that may be substituted; R⁶⁸, R⁶⁹, R⁷⁰, R⁷¹, R⁷², and R⁷³ are as defined above.)

Examples of M³ include (monovalent) residues of a metal complex represented by the following formulas:
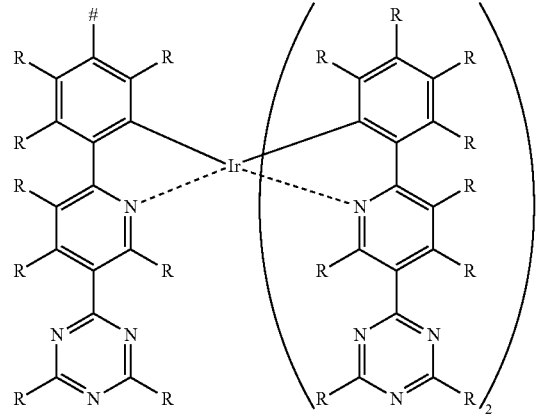
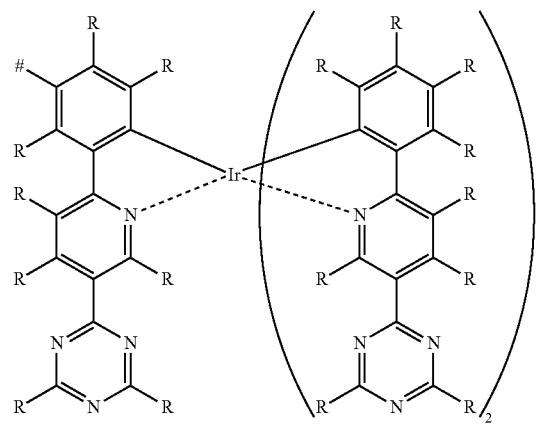
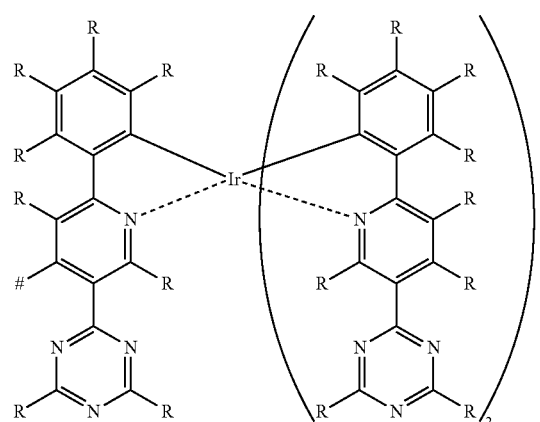
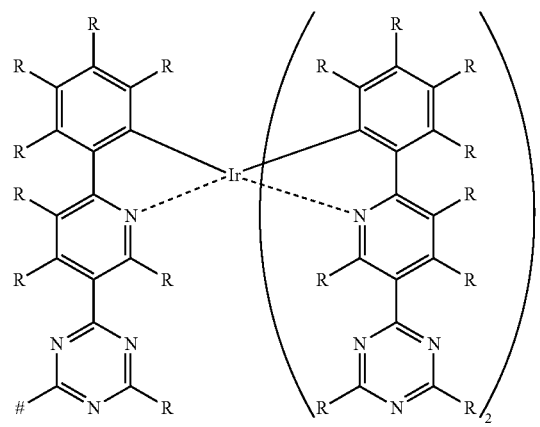
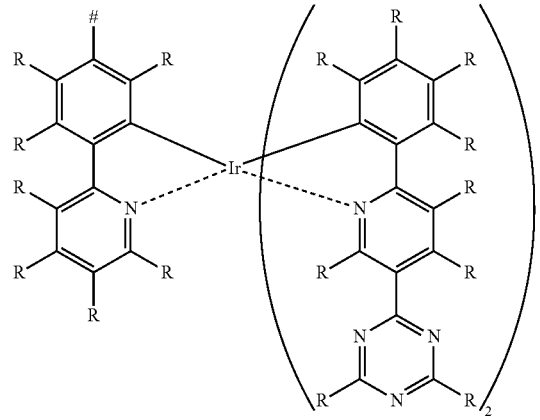
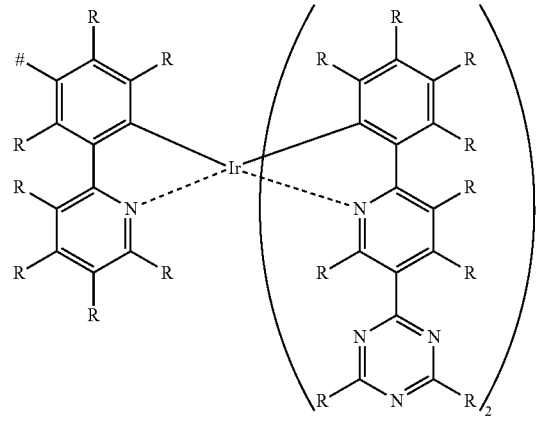
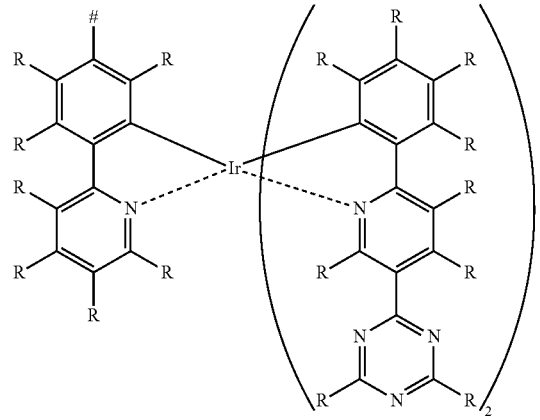

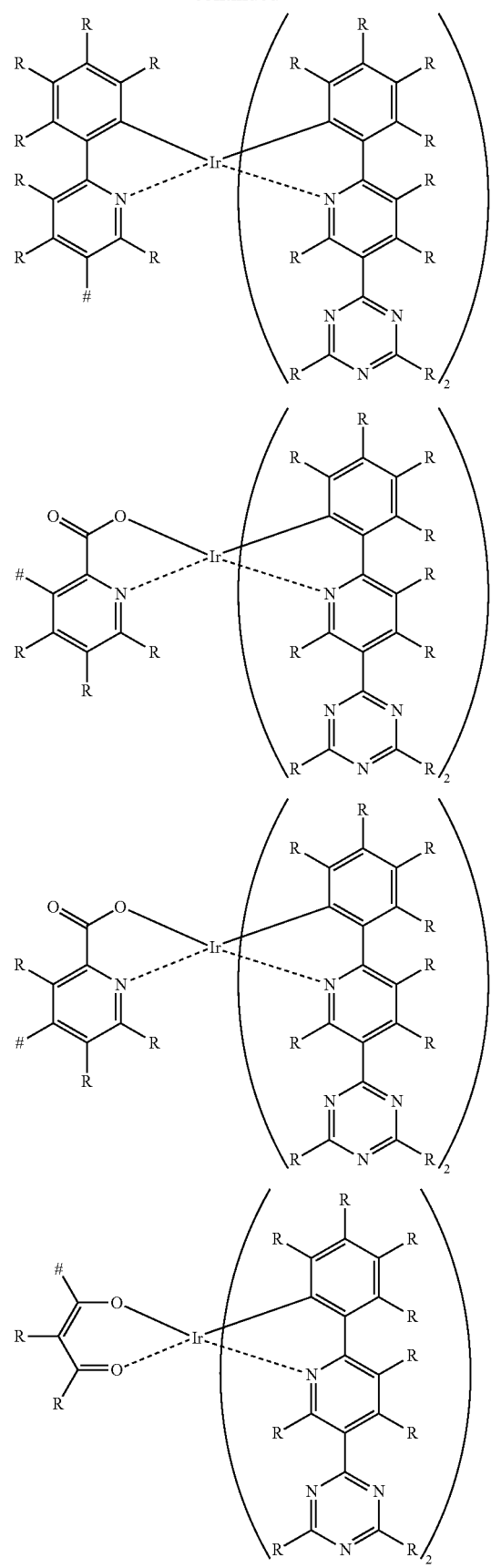
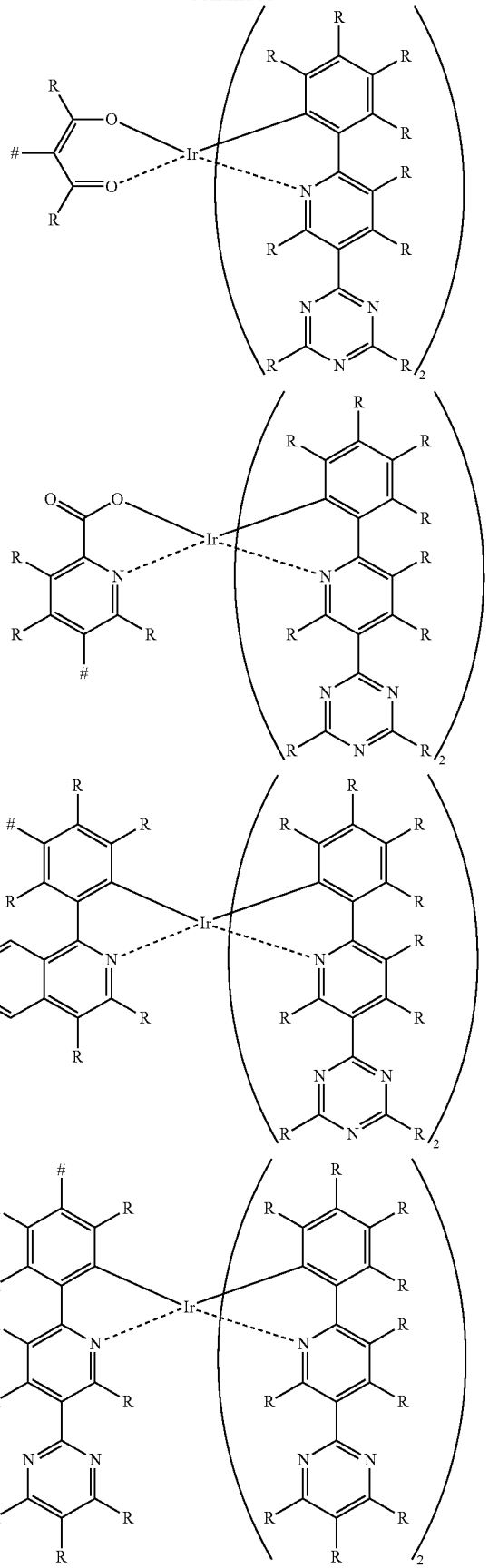

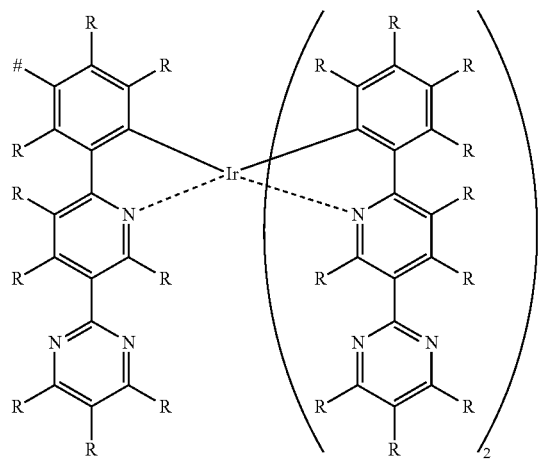

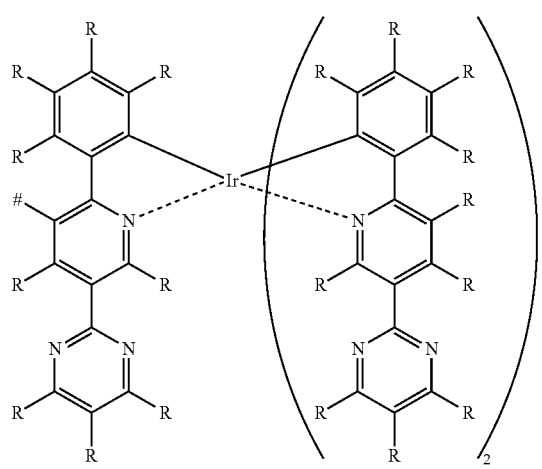

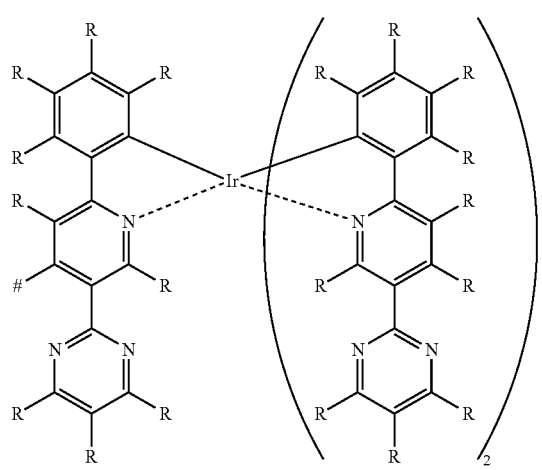

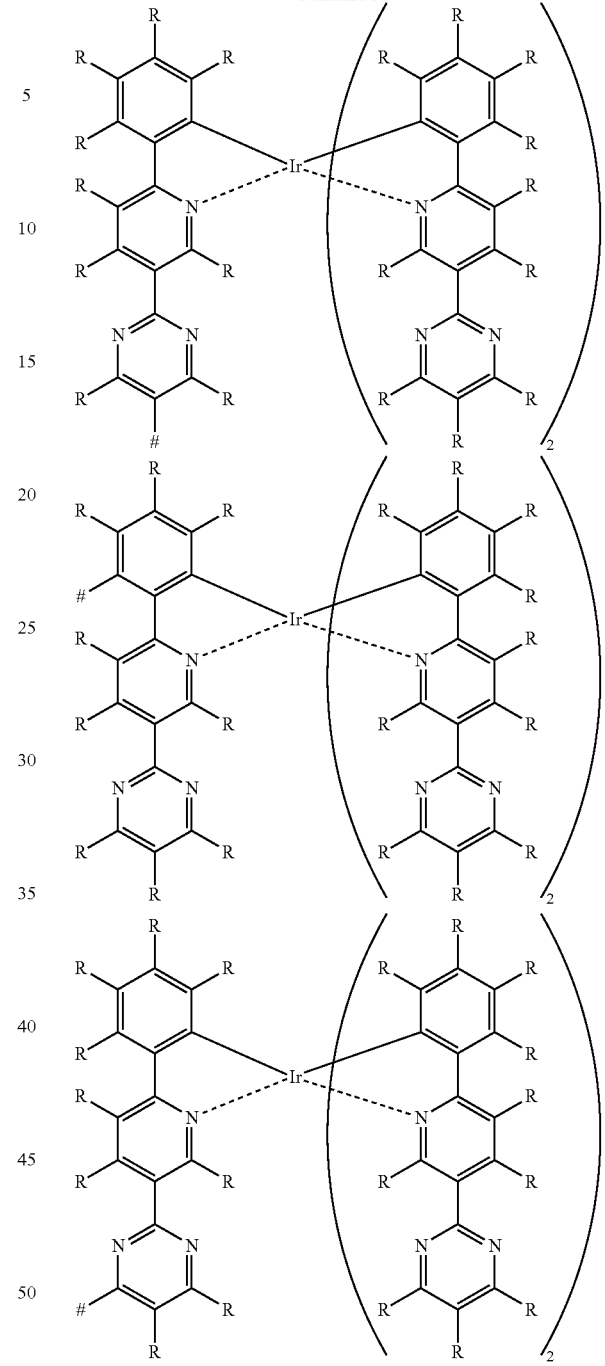

(wherein # and R are as defined above.)

Examples of the polymer compound having a residue of a metal complex in the side chain of the molecular chain include a polymer compound in which a residue of the metal complex is a monovalent group.

The molecular chain has a repeating unit represented by the formula: —(Ar')—, for example. In the formula, Ar' represents a divalent aromatic group having a group represented by 1 to 4 -L-$M^3$, or a divalent heterocyclic group having an atom selected from the group consisting of an oxygen atom, a silicon atom, a phosphorus atom, a boron atom, and a sulfur atom and a group represented by 1 to 4 -L-$M^3$. L and $M^3$ are as defined above. In the case where the alkylene group, alkenylene group, and alkynylene group represented by L include a —CH$_2$-group, one or more —CH$_2$— groups included in the alkylene group, one or more —CH$_2$— groups included in the alkenylene group, and one or more —CH$_2$— group included in the alkynylene group each may be substituted by a group selected from the group consisting of —O—, —S—, —C(=O)—, —C(=O)O—, —S(=O)—, —S(=O)$_2$—, —Si(R$^{74}$)(R$^{75}$)—, N(R$^{76}$)—, —B(R$^{77}$)—, —P(R$^{78}$)—, and —P(=O)(R$^{79}$)—. R$^{74}$, R$^{75}$, R$^{76}$, R$^{77}$, R$^{78}$, and R$^{79}$ each independently represent a hydrogen atom, an alkyl group, an aryl group, a monovalent heterocyclic group, or a cyano group. Other than the group represented by -L-M$^3$, Ar' may have a substituent selected from the group consisting of an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, and a cyano group. In the case where Ar' has a plurality of substituents, the substituents may be the same or different.

In the formula, the alkyl group represented by R$^{68}$, R$^{69}$, R$^{70}$, R$^{71}$, R$^{72}$, R$^{73}$, R$^{74}$, R$^{75}$, R$^{76}$, R$^{77}$, R$^{78}$, and R$^{79}$, the aryl group, the monovalent heterocyclic group, the cyano group, the alkyl group that is a substituent which Ar' may have, the alkoxy group, the alkylthio group, the aryl group, the aryloxy group, the arylthio group, the arylalkyl group, the arylalkoxy group, the arylalkylthio group, the arylalkenyl group, the arylalkynyl group, the amino group, the substituted amino group, the silyl group, the substituted silyl group, the halogen atom, the acyl group, the acyloxy group, the imine residue, the amide group, the acid imide group, the monovalent heterocyclic group, the carboxyl group, the substituted carboxyl group, and the cyano group are the same as those described and exemplified as the groups and atoms represented by R.

Examples of Ar' include groups represented by the following formulas:

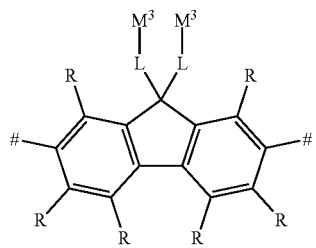

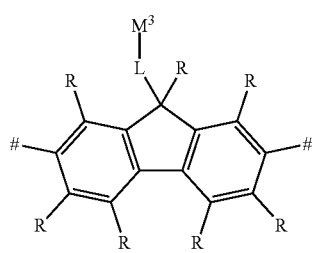

-continued

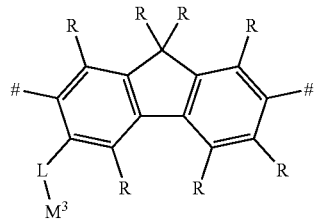

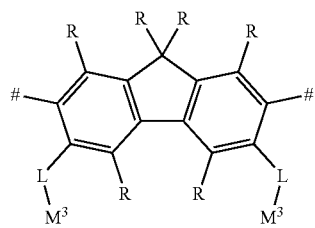

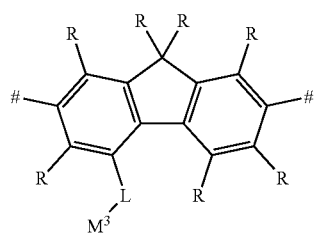

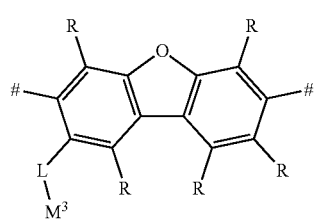

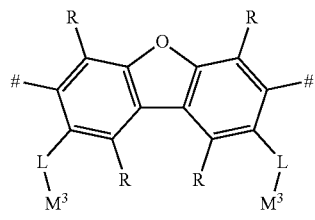

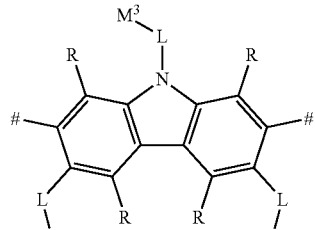

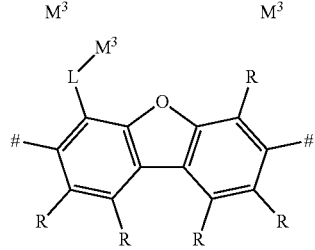

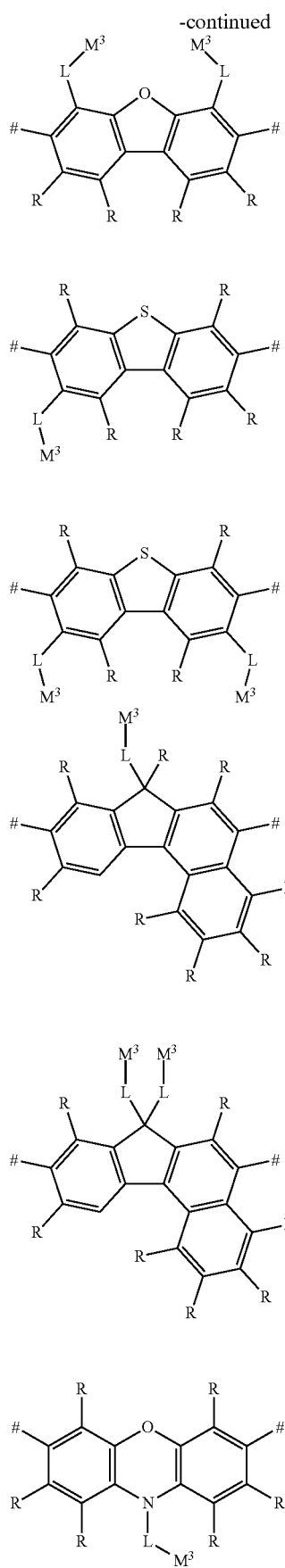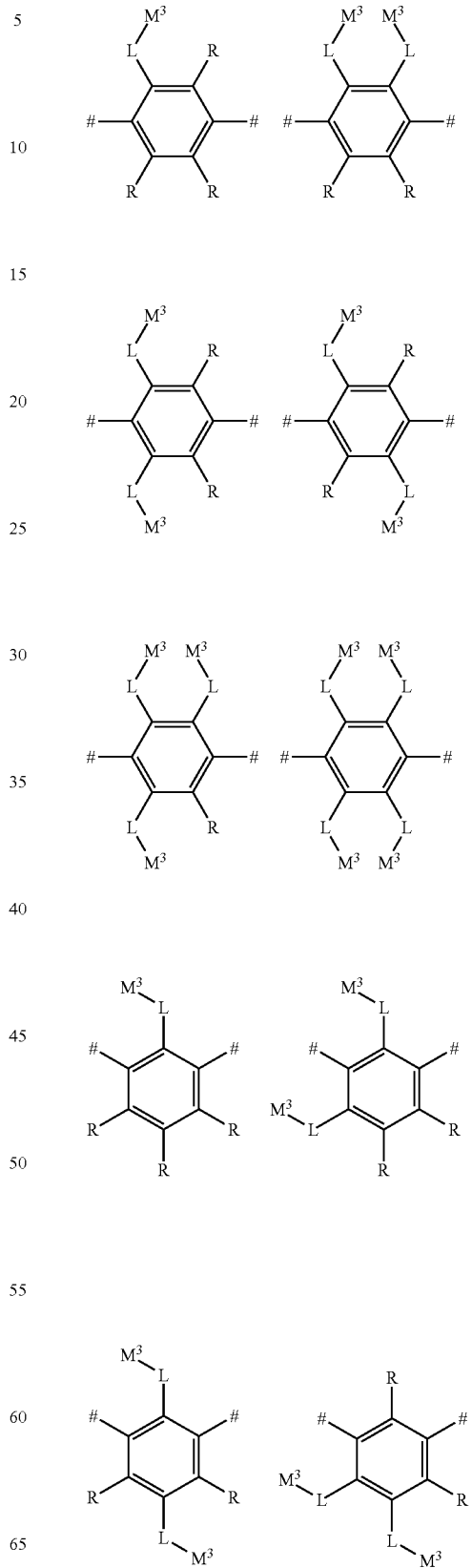

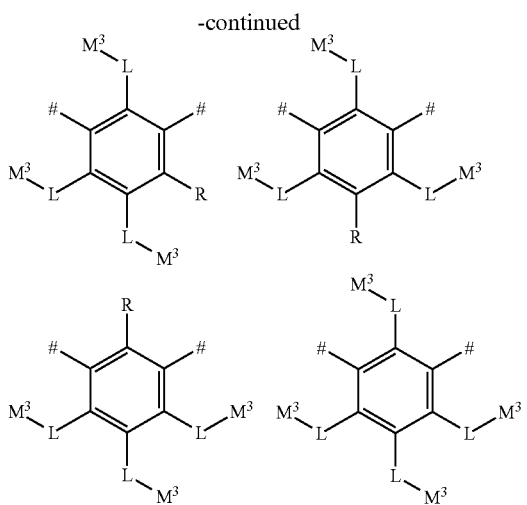

(wherein #, L, R, and M³ are as defined above.)

The number of carbon atoms of the alkylene group represented by L is usually 1 to 30, and preferably 1 to 15. Examples of the alkylene group include a methylene group, an ethylene group, a propylene group, a trimethylene group, a tetramethylen group, a pentamethylene group, a hexamethylene group, an octamethylene group, a 1,3-cyclopentylene group, and a 1,4-cyclohexylene group.

The number of carbon atoms of the alkenylene group represented by L is usually 2 to 30, and preferably 2 to 15. Examples of the alkenylene group include a vinylene group and a propylene group. Examples of the alkenylene group also include alkadienylene groups such as a 1,3-butadienylene group.

The number of carbon atoms of the alkynylene group represented by L is usually 2 to 30, and preferably 2 to 15. Examples of the alkynylene group include an ethynylene group. Examples of the alkynylene group also include groups having two triple bonds such as a 1,3-butanediynylene group.

The arylene group represented by L represents a group in which two hydrogen atoms are removed from an aromatic hydrocarbon compound. Carbon atoms that form the aromatic ring are usually 6 to 30, and preferably 6 to 15. Example of the arylene group include a phenylene group, a biphenylene group, a terphenylene group, a naphthalenediyl group, an anthracenediyl group, a phenanthrenediyl group, a pentalenediyl group, an indenediyl group, a heptalenediyl group, an indacenediyl group, a triphenylenediyl group, a binaphthyldiyl group, a phenylnaphthylenediyl group, a stilbenediyl group, and a fluorenediyl group.

The divalent heterocyclic group represented by L means an atomic group in which two hydrogen atoms are removed from a heterocyclic compound. The number of carbon atoms of the divalent heterocyclic group is usually 2 to 30, and preferably 2 to 15. The carbon atoms of a substituent are not included in the carbon atoms of the divalent heterocyclic group. The divalent heterocyclic group is preferably a divalent aromatic heterocyclic group. Examples of the divalent heterocyclic group include a pyridinediyl group, a diazaphenylene group, a quinolinediyl group, a quinoxalinediyl group, an acridinediyl group, a bipyridyldiyl group, and a phenanthrolinediyl group.

As L, a single bond, —O—, a methylene group, an ethylene group, a hexamethylene group, an octamethylene group, a vinylene group, a phenylene group, a biphenylene group, and a pyridinediyl group are preferable from the viewpoint of easiness to synthesize the polymer compound and luminous properties. The phenylene group and the pyridinediyl group are more preferable.

The polymer compound according to the present invention is preferably a polymer compound that does not impair greatly charge transportability and charge injection properties, and more preferably a conjugated polymers having excellent carrier (electrons or electron holes) transportability.

In the case where the polymer compound according to the present invention has the repeating unit including the residue of the metal complex represented by the formula (1) and the repeating unit including the divalent group represented by the formulas (3-1) to (3-5), the polymer compound according to the present invention may include other repeating units in the range that neither luminous properties nor charge transport properties are impaired. In this case, the total of the repeating unit including the residue of the metal complex represented by the formula (1) and the repeating unit including the divalent group represented by the formula (3-1) to (3-5) is preferably not less than 10 mol % of all the repeating units, and more preferably not less than 50 mol %, and particularly preferably not less than 80 mol %.

In the case where the polymer compound according to the present invention is used as a red light-emitting material, the peak wavelength in the EL light emission spectrum of the polymer compound of the present invention is preferably 550 to 800 nm, and more preferably 570 to 700 nm.

<Composition>

A composition according to the present invention contains the polymer compound, and preferably further contains a charge transport material and/or a light-emitting material.

The charge transporting material is classified into hole transport materials and electron transport materials. Organic compounds (low molecular organic compounds and/or polymer organic compounds) can be used for the material.

Examples of the hole transport material include materials known as a hole transport material for organic EL devices, e.g., aromatic amine, carbazole derivatives, and polyparaphenylene derivatives. Examples of the electron transport material include materials known as electron transport materials in the organic EL devices, e.g., oxadiazole derivative, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, and a metal complex of 8-hydroxyquinoline and derivatives thereof. The low molecular organic compound for the charge transporting material means a host compound and a charge injection transport compound that are used for low molecular organic EL devices. Specifically, examples thereof include compounds described in "Organic EL Display" (S. Tokito, C. Adachi and H. Murata, Ohmsha, Ltd.), p. 107; Monthly Display (vol. 9, No. 9, 2003, pp. 26-30); JP 2004-244400 A, JP 2004-277377 A, and the like. Depending on a kind of these charge transport materials, generally in order to obtain favorable light emission from the metal complex, the lowest triplet excitation energy of these charge transport materials is preferably larger than the lowest triplet excitation energy of the metal complex.

Examples of the low molecular organic compound for the charge transport material include compounds represented by the following formulas:

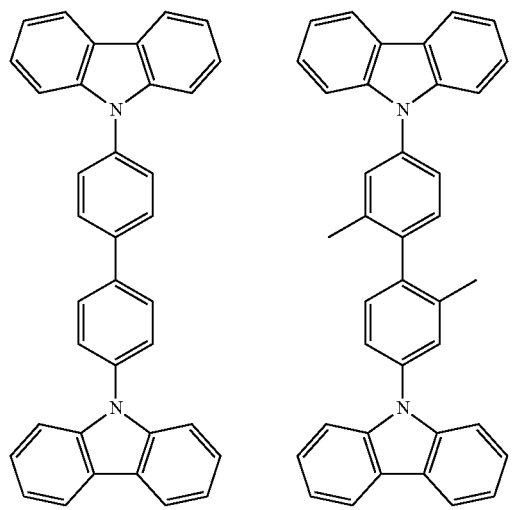
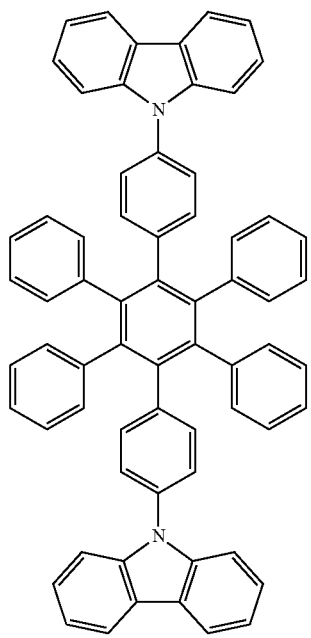
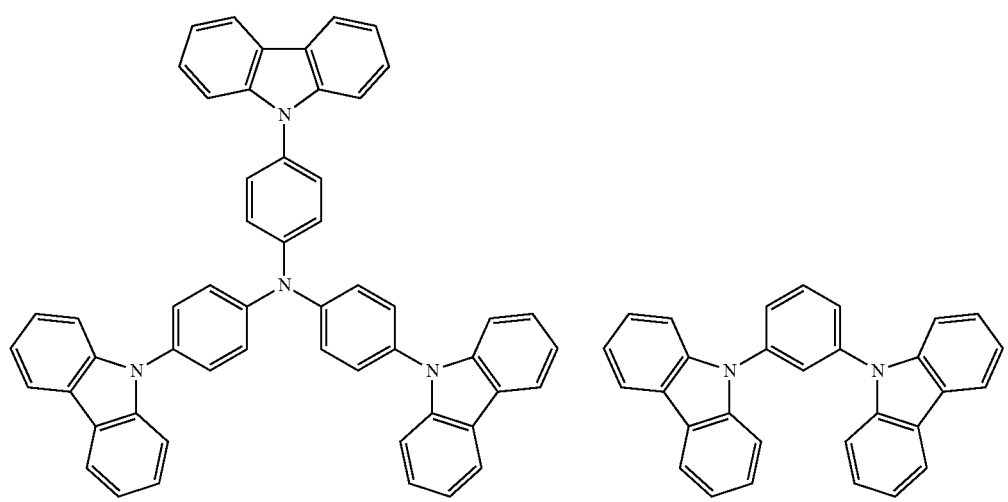
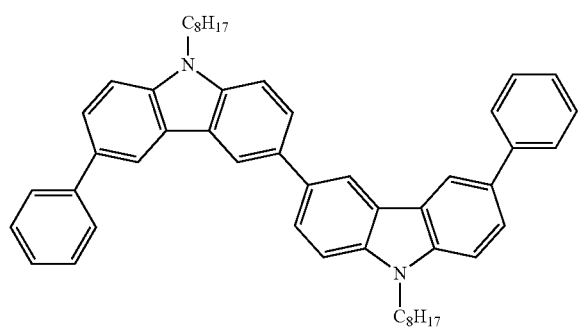

-continued
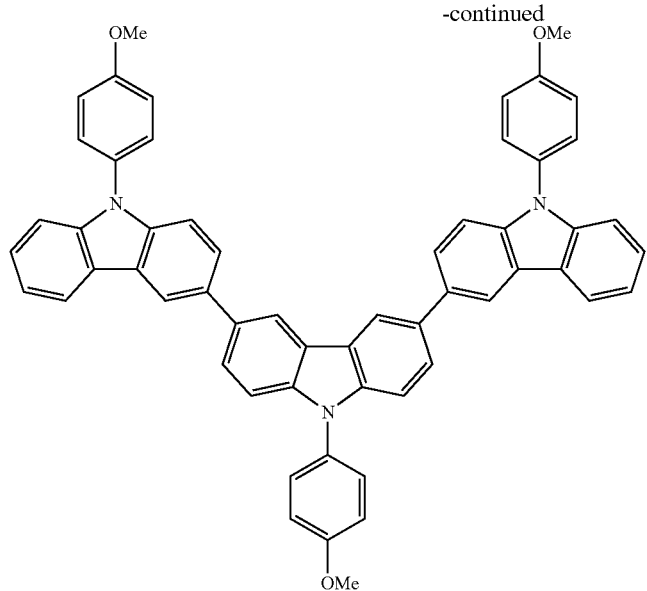
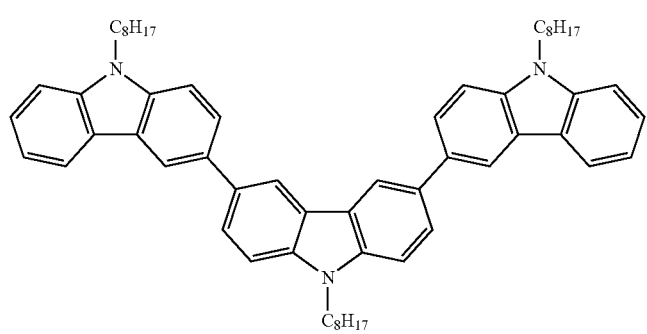
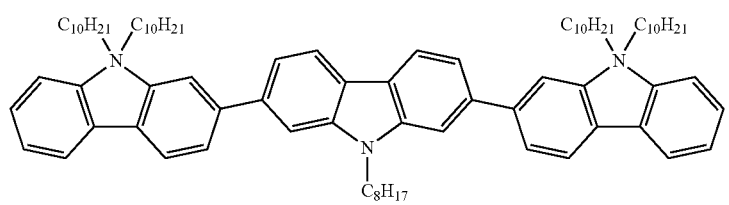
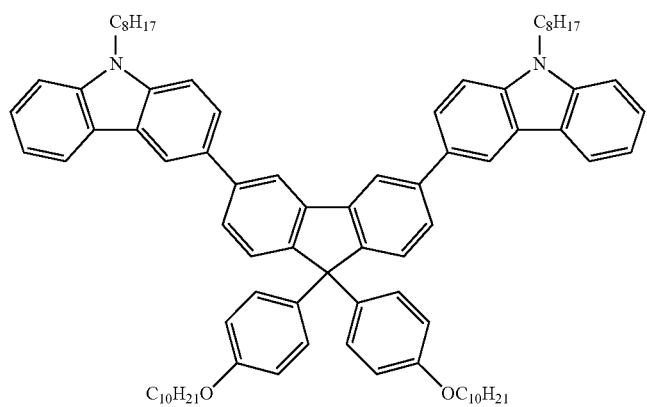

-continued
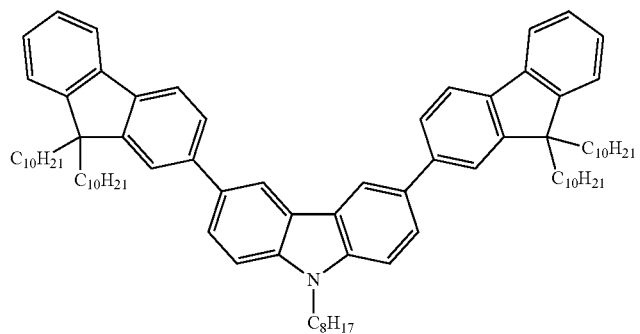
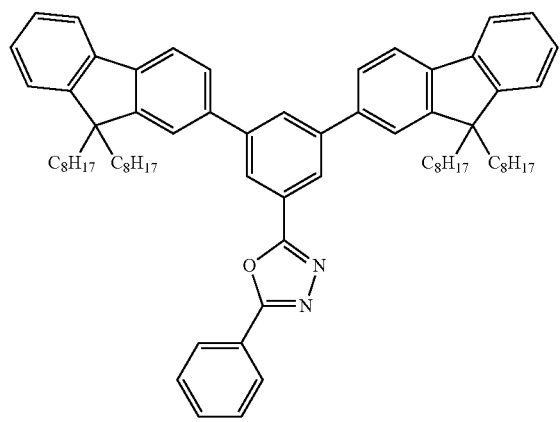
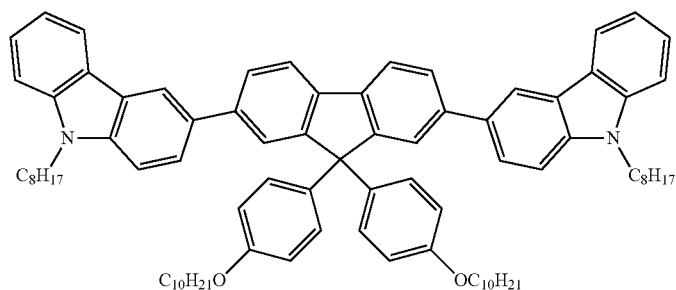
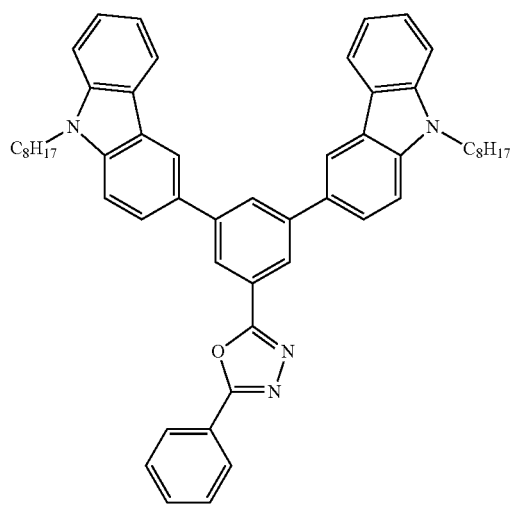
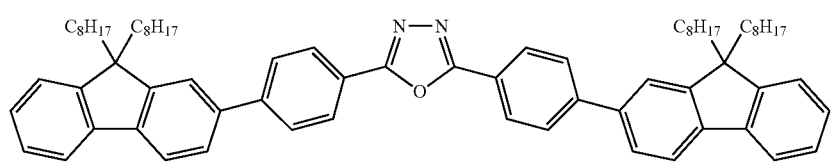

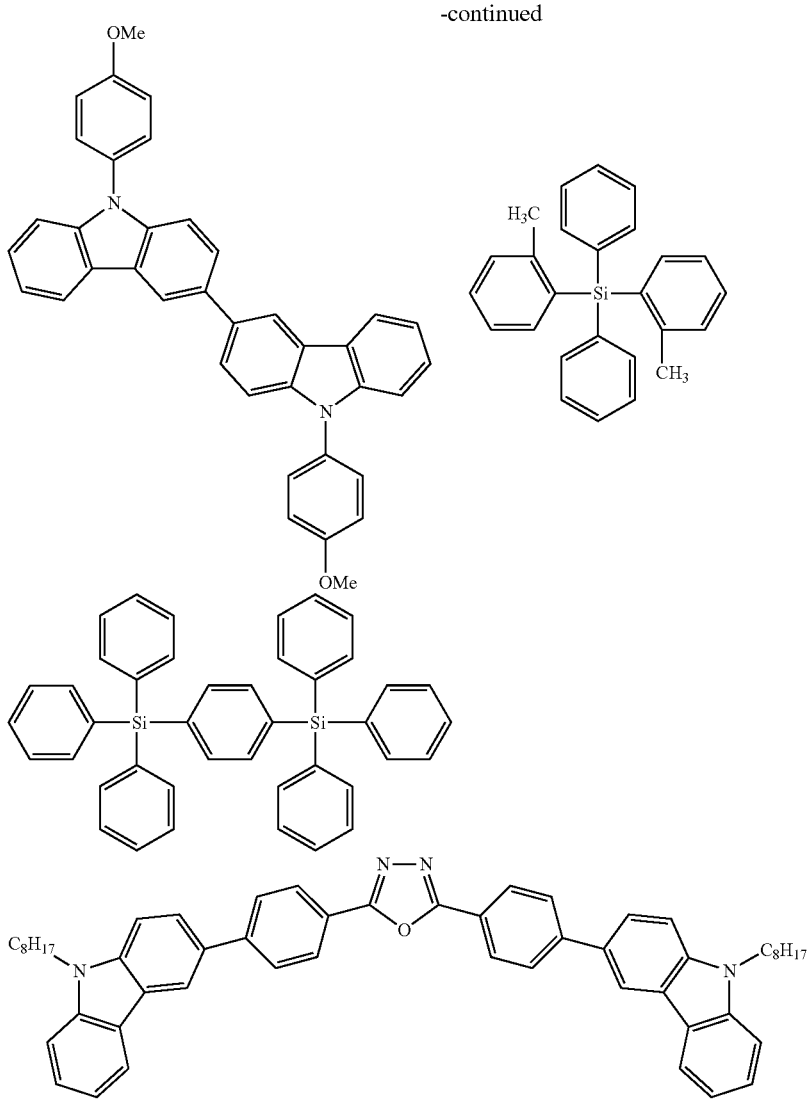

Examples of the polymer organic compound for the charge transport material include non-conjugated polymers and conjugated polymers. Examples of the non-conjugated polymers include polyvinyl carbazole. Examples of the conjugated polymers include polymers which contains an aromatic ring in the main chain. A phenylene group that may have a substituent, fluorene that may have a substituent, dibenzothiophene that may have a substituent, dibenzofuran that may have a substituent, those containing dibenzosilole that may have a substituent or the like in the main chain as a repeating unit, and copolymers with those units, are preferable. Examples of the polymer organic compound also include polymer compounds having a benzene ring that may have a substituent as a partial structure, and polymers described in JP 2003-231741 A, JP 2004-059899 A, JP 2004-002654 A, JP 2004-292546 A, U.S. Pat. No. 5,708,130, WO99/54385, WO00/46321, WO02/077060, "Organic EL Display" (S. Tokito, C. Adachi and H. Murata, Ohmsha, Ltd.), p. 111; Monthly Display (vol. 9, No. 9, 2002), pp. 47-51, and the like.

In addition to these, examples of the polymer organic compound for the charge transport material include polymers including a repeating unit represented by the formula (3a) or (3b), and include polymers including the following groups (namely, in the following exemplification, those without parentheses) and polymers including the following groups as a repeating unit, for example:

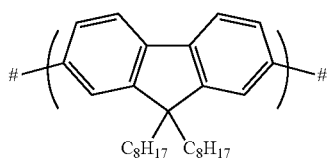

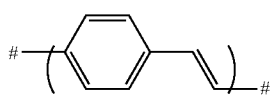

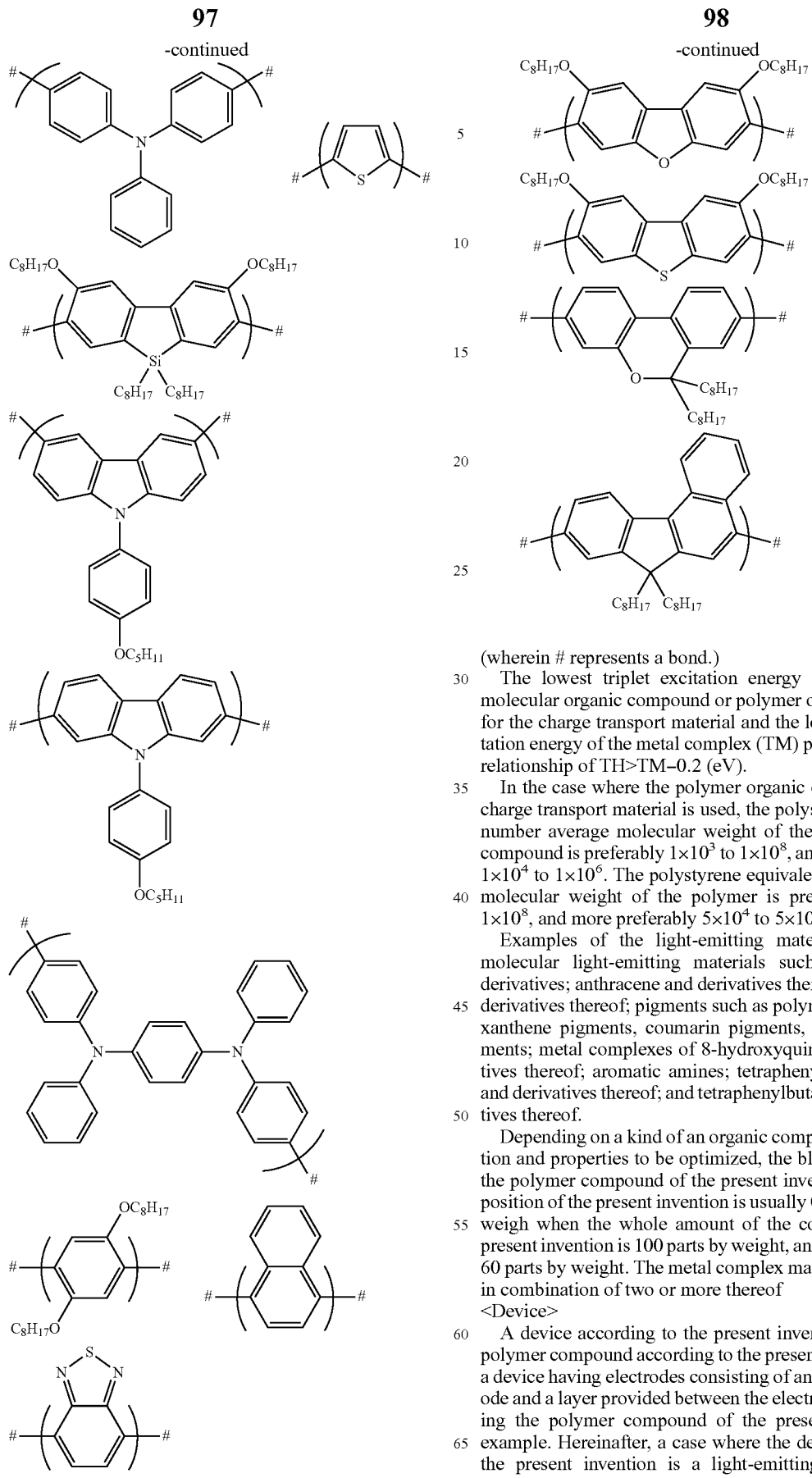

(wherein # represents a bond.)

The lowest triplet excitation energy (TH) of the low molecular organic compound or polymer organic compound for the charge transport material and the lowest triplet excitation energy of the metal complex (TM) preferably satisfy a relationship of TH>TM−0.2 (eV).

In the case where the polymer organic compound for the charge transport material is used, the polystyrene equivalent number average molecular weight of the polymer organic compound is preferably $1\times10^3$ to $1\times10^8$, and more preferably $1\times10^4$ to $1\times10^6$. The polystyrene equivalent weight average molecular weight of the polymer is preferably $1\times10^3$ to $1\times10^8$, and more preferably $5\times10^4$ to $5\times10^6$.

Examples of the light-emitting material include low molecular light-emitting materials such as naphthalene derivatives; anthracene and derivatives thereof; perylene and derivatives thereof; pigments such as polymethine pigments, xanthene pigments, coumarin pigments, and cyanine pigments; metal complexes of 8-hydroxyquinoline and derivatives thereof; aromatic amines; tetraphenylcyclopentadiene and derivatives thereof; and tetraphenylbutadiene and derivatives thereof.

Depending on a kind of an organic compound in combination and properties to be optimized, the blending amount of the polymer compound of the present invention in the composition of the present invention is usually 0.01 to 80 parts by weigh when the whole amount of the composition of the present invention is 100 parts by weight, and preferably 0.1 to 60 parts by weight. The metal complex may be used alone or in combination of two or more thereof <Device>

A device according to the present invention contains the polymer compound according to the present invention, and is a device having electrodes consisting of an anode and a cathode and a layer provided between the electrodes and containing the polymer compound of the present invention, for example. Hereinafter, a case where the device according to the present invention is a light-emitting device will be described as a typical example.

A light-emitting device according to the present invention includes a pair of electrodes consisting of an anode and a cathode; and a thin film formed of at least one layer (monolayer type) or several layers (multilayer type) of a light-emitting layer and sandwiched between the electrodes. At least one layer of the thin film layer contains the polymer compound of the present invention. The total content of the polymer compound of the present invention in the thin film is usually 0.1 to 100% by weight based on the entire weight of the light-emitting layer, preferably 0.1 to 80% by weight, and more preferably 0.5 to 60% by weight. In the light-emitting device according to the present invention, the light-emitting layer preferably contains the polymer compound of the present invention as a light-emitting material.

In the case where the light-emitting device according to the present invention is the monolayer type, the thin film is the light-emitting layer, and this light-emitting layer contains the polymer compound of the present invention. In the case where the light-emitting device according to the present invention is the multilayer type, the light-emitting device has the following configurations, for example:

(a) anode/hole injection layer (hole transport layer)/light-emitting layer/cathode,
(b) anode/light-emitting layer/electron injection layer (electron transport layer)/cathode, and
(c) anode/hole injection layer (hole transport layer)/light-emitting layer/electron injection layer (electron transport layer)/cathode.

The anode of the light-emitting device according to the present invention supplies holes to a hole injection layer, a hole transport layer, a light-emitting layer, and the like. It is effective that the anode has work function of not less than 4.5 eV. Metals, alloys, metal oxides, conductive compounds, a mixture thereof, and the like can be used for a material for the anode. Examples of the material for the anode include conductive metal oxides such as tin oxide, zinc oxide, indium oxide, and indium tin oxide (ITO); metals such as gold, silver, chromium, and nickel; a mixture or a laminate of these conductive metal oxides and a metal; inorganic conductive substances such as copper iodide, and copper sulfide; polyanilines; polythiophenes (PEDOT and the like); organic conductive materials such as polypyrrole; and a laminate of these and ITO.

The cathode of the light-emitting device according to the present invention supplies electrons to the electron injection layer, the electron transport layer, the light-emitting layer, and the like. As a material for the cathode, metals, alloys, metal halides, metal oxides, conductive compounds, or a mixture thereof can be used. Examples thereof include alkali metals (e.g., lithium, sodium, potassium) and fluorides and oxides thereof, alkaline earth metals (e.g., magnesium, calcium, barium, cesium) and fluorides and oxides thereof, gold, silver, lead, aluminum, alloys, mixed metals (e.g., sodium-potassium alloy, sodium-potassium mixed metal, lithium-aluminium alloy, lithium-aluminum mixed metal, magnesium-silver alloy, magnesium-silver mixed metal), and rare earth metals (e.g., indium, ytterbium).

The hole injection layer and the hole transport layer of the light-emitting device according to the present invention may have one of function to inject the holes from the anode, function to transport the holes, and function to block the electrons injected from the cathode. Known materials can be properly selected and used for materials for these layers. Examples thereof include polymers containing: carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styryl anthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, organic silane derivatives, polymer compounds of the present invention. Other examples thereof include conductive polymer oligomers such as aniline copolymers, thiophene oligomers, and polythiophene. These materials may be used alone or in combination of two or more thereof. The hole injection layer and the hole transport layer may have a single layer structure formed of one or more of the materials, or may have a multilayer structure formed of several layers of the same composition or different compositions.

The electron injection layer and the electron transport layer of the light-emitting device according to the present invention may have one of function to inject the electrons from cathode, function to transport the electrons, and function to block the holes injected from the anode. Examples of materials used for the electron injection layer and the electron transport layer include triazole derivatives, oxazole derivatives, oxadiazole derivatives, imidazole derivatives, fluorenone derivatives, anthraquinodimethane derivatives, antrone derivatives, diphenylquinone derivatives, thiopyrandioxide derivatives, carbodiimide derivatives, fluorenylidene methane derivatives, distyryl derivatives, aromatic ring tetracarboxylic acid anhydrides such as naphthalene and perylene, various metal complexes represented by metal complexes of phthalocyanine derivatives and 8-quinolinol derivatives and metal complexes having metal phthalocyanine, benzoxazol, and benzothiazole as a ligand, organic silane derivatives, and the polymer compound of the present invention. The electron injection layer and the electron transport layer may have a single layer structure formed of one or more of the materials, or may have a multilayer structure formed of several layers of the same composition or different compositions.

In the light-emitting device according to the present invention, inorganic compounds made of an insulator or a semiconductor can also be used as the materials for the electron injection layer and the electron transport layer. When the electron injection layer and the electron transport layer are made of an insulator or a semiconductor, leak of current can be prevented effectively so that electron injection properties can be improved. As such an insulator, at least one metallic compound selected from the group consisting of alkali metal chalcogenides, alkaline earth metal chalcogenides, halides of alkali metals, and halides of alkaline earth metals can be used. Examples of preferable alkali metal chalcogenides include CaO, BaO, SrO, BeO, BaS, and CaSe. Examples of the semiconductor that forms the electron injection layer or the electron transport layer include oxides, nitrides, or oxynitrides containing at least one element selected from the group consisting of Ba, Ca, Sr, Yb, Al, Ga, In, Li, Na, Cd, Mg, Si, Ta, Sb, and Zn. These oxides, nitrides, and oxynitrides may be used alone or in combination of two or more thereof.

In the present invention, a reducing dopant may be added to an interface region between the cathode and the thin film that contacts the cathode. As the reducing dopant, a compound made of at least one selected from the group consisting of alkali metals, oxides of alkaline earth metals, alkaline earth metals, rare earth metals, oxides of alkali metals, halides of alkali metals, oxides of alkaline earth metals, halides of alkaline earth metals, oxides of rare earth metals, halides of rare earth metals, alkali metal complexes, alkaline earth metal complexes, and rare earth metal complexes is preferable.

The light-emitting layer of the light-emitting device according to the present invention can inject the holes from the anode or the hole injection layer when a voltage is applied, and has function to inject the electrons from the cathode or the electron injection layer, function to move the injected charges (electrons and holes) by a force of an electric field, and function to provide a place for recombination of the electrons and the holes and to lead this to light emission. The light-emitting layer of the light-emitting device according to the present invention preferably contains the polymer compound of the present invention, and may contain a host material having the polymer compound as a guest material. Examples of the host material include those having a fluorene skeleton, those having a carbazole skeleton, those having a diarylamine skeleton, those having a pyridine skeleton, those having a pyrazine skeleton, those having a triazine skeleton, and those having an arylsilane skeleton. T1 (energy level in the lowest triplet excitation state) of the host material is preferably larger than that of the guest material. More preferably, the difference is larger than 0.2 eV. The host material may be a low molecular compound, or may be a polymer compound. A light-emitting layer having the host material doped with the light-emitting material can be formed by mixing the host material and a light-emitting material such as the metal complex and applying the mixture, or by performing coevaporation of the host material and the light-emitting material.

In the light-emitting device according to the present invention, examples of a method for forming each layer include vacuum evaporation methods (e.g., resistance heating vacuum deposition, an electron beam method), spattering methods, LB methods, molecule laminating methods, coating methods (e.g., a casting method, a spin coat method, a bar coat method, a blade coat method, a roll coat method, gravure printing, screen printing, an ink jet method). Of these, film formation by coating is preferable because the production process can be simplified. In the coating method, a film can be formed by dissolving the polymer compound of the present invention in a solvent to prepare a coating liquid, coating the coating liquid on a desired layer (or electrode), and drying the coating liquid. The coating liquid may contain a resin as a host material and/or a binder. The resin can be dissolved in the solvent, or can be dispersed in the solvent. As the resin, non-conjugated polymers (for example, polyvinyl carbazole) and conjugated polymers (for example, polyolefin system polymers) can be used. More specifically, the resin can be selected according to a purpose from polyvinyl chloride, polycarbonate, polystyrenes, polymethylmethacrylates, polybutylmethacrylates, polyesters, polysulfones, polyphenylene oxides, polybutadienes, poly(N-vinylcarbazole), hydrocarbon resins, ketone resins, phenoxy resins, polyamides, ethyl celluloses, vinyl acetates, ABS resins, polyurethanes, melamine resins, unsaturated polyester resins, alkyd resins, epoxy resins, and silicon resins, for example. The solution may contain an antioxidant, a viscosity controlling agent, and the like as an optional component.

—Photoelectric Device—

The polymer compound according to the present invention can be used for production of photoelectric devices.

Examples of the photoelectric devices include photoelectric conversion devices. Examples thereof include a device in which a layer containing the polymer compound of the present invention is provided between two electrodes at least one of which is transparent or semitransparent, and a device having a comb shaped electrode formed on a layer formed on a substrate and containing the polymer compound of the present invention. In order to improve properties, fullerene, carbon nanotube, or the like may be mixed.

Examples of a method for producing a photoelectric transducer include a method described in Japanese Patent No. 3146296, and include a method for forming a layer (thin film) containing the polymer compound of the present invention on a substrate having a first electrode, and forming a second electrode thereon, and a method for forming a layer (thin film) containing the polymer compound of the present invention on a set of comb shaped electrodes formed on a substrate, for example. One of the first and second electrodes is transparent or semitransparent.

As a method for forming a layer (thin film) containing the polymer compound of the present invention or a method for mixing fullerene and carbon nanotube, the methods exemplified in the case of the light-emitting device can be suitably used.

<Liquid Composition>

A liquid composition according to the present invention contains the polymer compound according to the present invention, and solvent or dispersion medium. As a solvent and a dispersion medium used for the liquid composition according to the present invention, a stable solvent or dispersion obtained by uniformly dissolving or dispersing components of a thin film can be properly selected from known solvents and be used. Examples of such a solvent include chlorine based solvents (e.g., chloroform, methylene chloride, 1,2-dichloroethane, 1,1,2-trichloroethane, chlorobenzene, o-dichlorobenzene), ether based solvents (e.g., tetrahydrofuran, dioxane), aromatic hydrocarbon based solvents (e.g., benzene, toluene, xylene), aliphatic hydrocarbon based solvents (e.g., cyclohexane, methylcyclohexane, n-pentane, n-hexane, n-heptane, n-octane, n-nonane, n-decane), ketone based solvents (e.g., acetone, methyl ethyl ketone, cyclohexanone), ester based solvents (e.g., ethyl acetate, butyl acetate, ethyl cellosolve acetate), polyhydric alcohols and derivatives thereof (e.g., ethylene glycol, ethylene glycol monobutyl ether, ethylene glycol monoethyl ether, ethylene glycol monomethyl ether, dimethoxyethane, propylene glycol, diethoxy methane, triethylene glycol monoethyl ether, glycerol, 1,2-hexandiol), alcoholic solvents (e.g., methanol, ethanol, propanol, isopropanol, cyclohexanol), and sulfoxide based solvents (e.g., dimethyl sulfoxide), amide based solvents (e.g., N-methyl-2-pyrrolidone, N,N-dimethylformamide). These solvents may be used alone or in combination of two or more thereof.

In the case where the liquid composition is used for the ink jet method, the liquid composition may contain a known additive in order to obtain favorable dischargeability of the liquid composition and repeatability thereof. Examples of this known additive include solvents having a high boiling point in order to suppress vaporization from a nozzle (e.g., anisole, bicyclohexylbenzene). Preferably, a liquid composition containing this known additive has a viscosity at 25° C. of 1 to 100 mPa·s.

A preferable film thickness of each layer in the light-emitting device according to the present invention changes according to a kind and lamination structure of the materials. Usually, an excessively thin film thickness easily causes defects such as pinhole, and conversely, at an excessively thick film thickness, a high applied voltage is needed and luminous efficiency deteriorates. Accordingly, several nanometers to 1 μm are usually preferable.

Examples of application of the light-emitting device according to the present invention include a planar light source, a light source for lighting (or light source), a light source for signs, a light source for back lights, display apparatuses, and printer heads. As the display apparatus, a known drive technique, a known drive circuits and the like are used, and a configuration of a segmental type, a dot-matrix type, and the like can be selected.

<Production Method>

The polymer compound according to the present invention can be synthesized by a production method comprising a method for reacting the metal complex represented by the formula (5) with the compound represented by the formula (6-1), (6-2), (6-3), (6-4), or (6-5), for example.

In the formula (5), examples of a polymerization reactive group represented by $W^1$ and $W^2$ include a halogen atom, an alkylsulfonyloxy group, an arylsulfonyloxy group, an arylalkylsulfonyloxy group, a boric acid ester residue, a sulfonium methyl group, a phosphonium methyl group, a phosphonate methyl group, a monohalogenated methyl group, —MgX (X represents a halogen atom), a stannyl group, —B(OH)$_2$, a formyl group, and a cyano group. —B(OH)$_2$, the boric acid ester residue, —MgX, the stannyl group, and the halogen atom are preferable.

Examples of the halogen atom that is the polymerization reactive group include a fluorine atom, a chlorine atom, a bromine atom, and an iodine atom. The chlorine atom, the bromine atom, and the iodine atom are preferable, and the bromine atom is more preferable.

Examples of the alkylsulfonyloxy group that is the polymerization reactive group include a methylsulfonyloxy group, an ethylsulfonyloxy group, and a trifluoromethylsulfonyloxy group.

Examples of the arylsulfonyloxy group that is the polymerization reactive group include a phenylsulfonyloxy group and a p-tolylsulfonyloxy group.

Examples of the arylalkylsulfonyloxy group that is the polymerization reactive group include a benzylsulfonyloxy group.

Examples of the boric acid ester residue that is the polymerization reactive group include a dialkyl ester residue, a diaryl ester residue, and a diarylalkyl ester residue, and a group represented by the following formula is preferable:

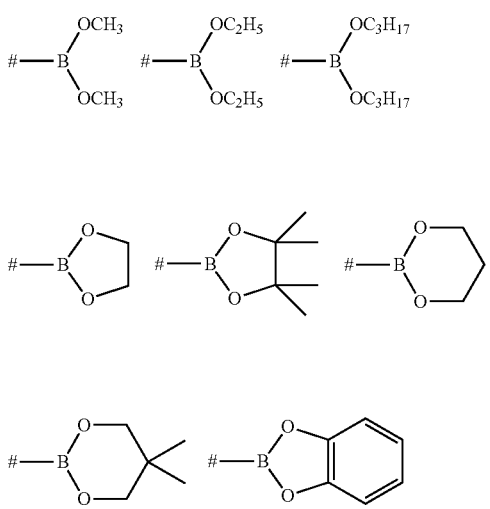

(wherein # represents a bond.)

Examples of the sulfonium methyl group include groups represented by the following formulas:

$$—CH_2S^+Me_2X^-, —CH_2S^+Ph_2X^-$$

(wherein X represents a halogen atom, and Ph represents a phenyl group.)

Examples of the phosphonium methyl group include a group represented by the following formula:

$$—CH_2P^+Ph_3X^-$$

(wherein X represents a halogen atom.)

Examples of the phosphonate methyl group include a group represented by the following formula:

$$—CH_2PO(OR^c)_2$$

(wherein X represents a halogen atom; $R^c$ represents an alkyl group, an aryl group, or an arylalkyl group.)

Examples of the monohalogenated methyl group include a monofluoromethyl group, a monochloromethyl group, a monobromomethyl group, and a monoiodomethyl group.

Examples of —MgX include —MgCl, —MgBr, and —MgI.

The stannyl group may have a substituent, and examples thereof include an unsubstituted stannyl group (—SnH$_3$), a trichlorostannyl group, a trimethylstannyl group, a triethylstannyl group, a tri-n-butylstannyl group, a triphenylstannyl group, and a tribenzylstannyl group.

As the polymerization reactive group, the halogen atom, the alkylsulfonyloxy group, the arylsulfonyloxy group, and the arylalkylsulfonyloxy group are preferable in the case where a zerovalent nickel complex is used in a Yamamoto coupling reaction, for example, and the alkylsulfonyloxy group, the halogen atom, the boric acid ester residue, and —B(OH)$_2$ are preferable in the case where a nickel catalyst or a palladium catalyst is used in a Suzuki coupling reaction, for example.

The polymer compound according to the present invention can be produced at a temperature of not less than the melting point of an organic solvent and not more than the boiling point thereof by dissolving a compound having a plurality of substituents related with polymerization and serving as a monomer in the organic solvent when necessary, and using an alkali and an appropriate catalyst, for example. As a method for producing a polymer according to the present invention, known methods described below can be used: "Organic Reactions," vol. 14, pp. 270 to 490, John Wiley & Sons, Inc., 1965; "Organic Syntheses," Collective Volume VI, pp. 407-411, John Wiley & Sons, Inc., 1988; Chem. Rev., vol. 95, p. 2457 (1995); J. Organomet. Chem., vol. 576, p. 147 (1999); Makromol. Chem., Macromol. Symp., vol. 12, p. 229 (1987), and the like.

In the production method according to the present invention, a known condensation reaction can be used according to the polymerization reactive group of the compound represented by the formula (5) and the compound represented by the formulas (6-1) to (6-5). A polymer compound (copolymer) can be produced by polymerization in the copresence of a compound having not less than two polymerization reactive groups. A polymer compound having a branching structure can be produced by copolymerizing a compound having not less than three polymerization reactive groups.

In the production method according to the present invention, in the case where the condensation reaction is a reaction to produce double bonds, examples of the reaction include methods described in JP 5-202355 A, namely, polymerization by a Wittig reaction of a compound having a formyl group with a compound having a phosphonium methyl group, or a compound having a formyl group with phosphonium methyl group; polymerization by a Heck reaction of a compound having a vinyl group with a compound having a halogen atom; polycondensation by a method for dehydrohalogenation of a compound having not less than two monohalogenated methyl groups; polycondensation by a method for sulfonium salt decomposition of a compound having not less than two sulfonium methyl groups; and polymerization by a Knoevenagel reaction of a compound having a formyl group with a compound having a cyano group; and methods such as polymerization by a McMurry reaction of a compound having not less than two formyl groups.

In the production method according to the present invention, in the case where the condensation reaction is a reaction to produce triple bonds, examples of the reaction include a Heck reaction and a Sonogashira reaction.

In the case where neither double bonds nor triple bonds are produced, examples of the production method include a method for polymerization from a corresponding monomer using a Suzuki coupling reaction, a method for polymerization using a Grignard reaction, a method for polymerization using a Ni(0) complex, a method for polymerization using an oxidizer such as $FeCl_3$, a method for electrochemical oxidation polymerization, and a method using decomposition of an intermediate polymer having an appropriate leaving group.

Of these, polymerization using the Wittig reaction, polymerization using the Heck reaction, polymerization using the Knoevenagel reaction, the method for polymerization using the Suzuki coupling reaction, the method for polymerization using the Grignard reaction, and the method for polymerization using a nickel zero value complex are preferable from the viewpoint of easiness of controlling a molecular weight and easiness of controlling a composition ratio in copolymerization.

In the production method according to the present invention, preferably, the polymerization reactive groups $W^1$ and $W^2$ are —$B(OH)_2$, the boric acid ester residue, or the halogen atom, the ratio of the total (J) of the number of mols of the halogen atoms and the total (K) of the number of mols of —$B(OH)_2$ and the boric acid ester residue that all the raw material compounds have is substantially 1 (K/J is usually 0.7 to 1.2), and condensation polymerization is performed using a nickel catalyst or a palladium catalyst.

In these production methods, examples of the raw material compound include a combination of a dihalogenated compound and a diboric acid compound or a diboric acid ester compound; a halogen-boric acid compound; and a halogen-boric acid ester compound.

Moreover, the polymer compound having a residue of the metal complex (namely, the residue of the metal complex represented by $M^3$) at a terminal of the molecular chain according to the present invention can be synthesized by a reaction of the polymerization reactive group located at a terminal at a condensation polymerization reaction and containing the compound represented by the formulas (6-1) to (6-5) with the compound represented by $m^1=1$ in the formula (5).

In the production method according to the present invention, in order to suppress a side reaction, the reaction is preferably advanced under an inert atmosphere by using an organic solvent subjected to sufficient deoxidation treatment before use. Dehydrating treatment may be performed when necessary, except the cases of a reaction in a two phase system with water such as the Suzuki coupling reaction.

Examples of the organic solvent that may be used for the production method according to the present invention include saturated hydrocarbons such as pentane, hexane, heptane, octane, and cyclohexane; unsaturated hydrocarbons such as benzene, toluene, ethylbenzene, and xylene; halogenated saturated hydrocarbons such as carbon tetrachloride, chloroform, dichloromethane, chlorobutane, bromobutane, chloropentane, bromopentane, chlorohexane, bromohexane, chlorocyclohexane, and bromocyclohexane; halogenated unsaturated hydrocarbons such as chlorobenzene, dichlorobenzene, and trichlorobenzene; alcohols such as methanol, ethanol, propanol, isopropanol, butanol, and t-butyl alcohol; carboxylic acids such as formic acid, acetic acid, and propionic acid; ethers such as dimethylether, diethylether, methyl-t-butylether, tetrahydrofuran, tetrahydropyran, and dioxane; amines such as trimethylamine, triethylamine, N,N,N',N'-tetramethylethylenediamine, and pyridine; amides such as N,N-dimethylformamide, N,N-dimethylacetamide, N,N-diethylacetamide, and N-methylmorpholineoxide. These organic solvents may be used alone or in combination of two or more thereof.

In the production method according to the present invention, an alkali and an appropriate catalyst may be added properly in order to accelerate the reaction. Preferably, the alkali and the catalyst are sufficiently dissolved in a solvent used for the reaction. Examples of a method for mixing an alkali or a catalyst include a method for adding a solution of an alkali or a catalyst slowly while stirring a reaction solution under an inert atmosphere of argon, nitrogen, or the like; or a method for adding a reaction solution slowly into a solution of an alkali or a catalyst.

The compound represented by the formula (5) can be produced from the compound represented by the formula (1a), for example. First, the compound represented by the formula (1a) is dissolved in a solvent, and N-bromosuccinimide is added thereto to react the compound represented by the formula (1a) with N-bromosuccinimide. Then, the compound represented by the following formula (5a) is produced. In this reaction, a halogenated hydrocarbon solvent such as methylene chloride can be used.

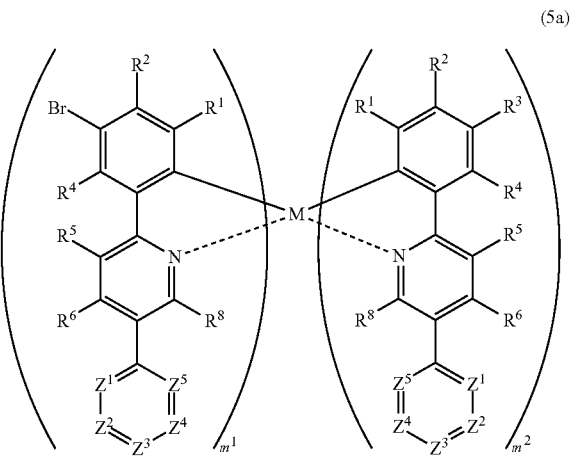

(5a)

(wherein $m^1, m^2, M, R^1, R^2, R^3, R^4, R^5, R^6, R^8, Z^1, Z^2, Z^3, Z^4$, and $Z^5$ are as defined above.)

The compound represented by the formula (5a) can be further reacted, and converted into a compound having the polymerization reactive group. Specifically, by reacting the compound represented by the formula (5a) with bis(pinacolato)diboron under a palladium catalyst, the compound represented by the formula (5a) can be converted into the compound having a boric acid ester residue as the polymerization reactive group, which is represented by the following formula (5b):

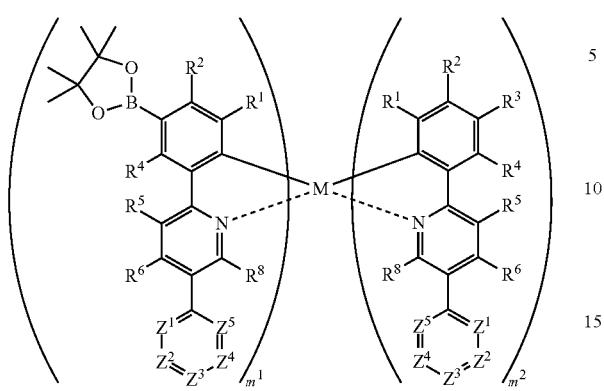

(wherein $m^1, m^2, M, R^1, R^2, R^3, R^4, R^5, R^6, R^8, Z^1, Z^2, Z^3, Z^4$, and $Z^5$ are as defined above.)

The polymer compound according to the present invention can also be synthesized by a production method comprising a method for reacting the compound represented by the formula (12) with the compound represented by the formula (6-1), (6-2), (6-3), (6-4), or (6-5).

In the formula (12), examples of the polymerization reactive group represented by $W^3$ include a halogen atom, an alkylsulfonyloxy group, an arylsulfonyloxy group, an arylalkylsulfonyloxy group, a boric acid ester residue, —MgX (X represents a halogen atom), a stannyl group, and —B(OH)$_2$. —B(OH)$_2$, the boric acid ester residue, —MgX, the stannyl group, and the halogen atom are preferable.

In the formula (12), the polymerization reactive group represented by $W^3$, i.e., the halogen atom, the alkylsulfonyloxy group, the arylsulfonyloxy group, the arylalkylsulfonyloxy group, the boric acid ester residue, —MgX, and the stannyl group are the same as those described and exemplified as the polymerization reactive group represented by $W^1$ and $W^2$ mentioned above.

Examples of the compound represented by the formula (12) include compounds shown below:

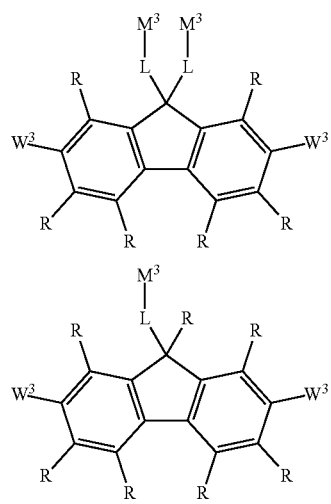

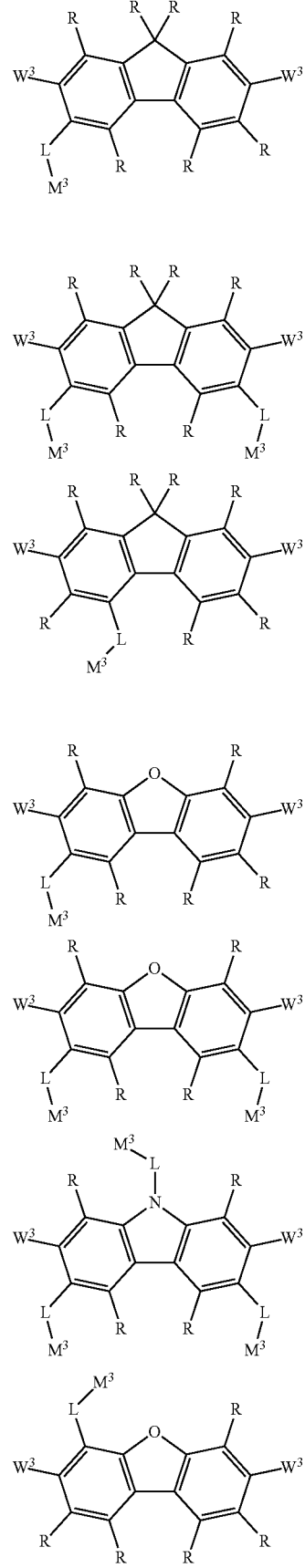

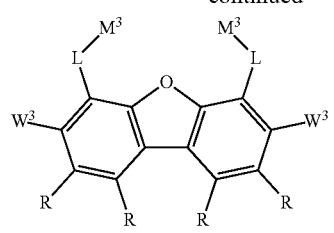
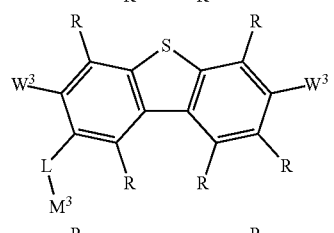
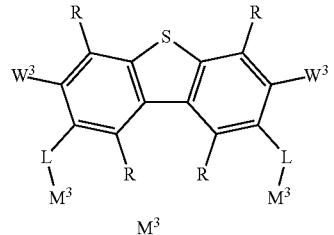
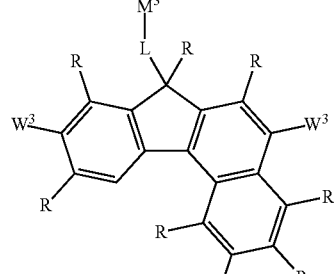
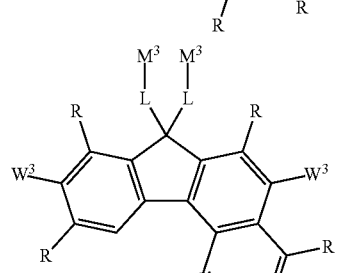
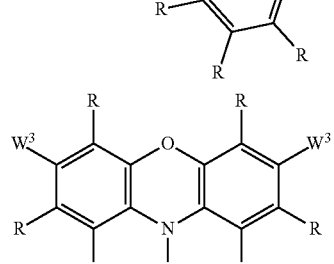
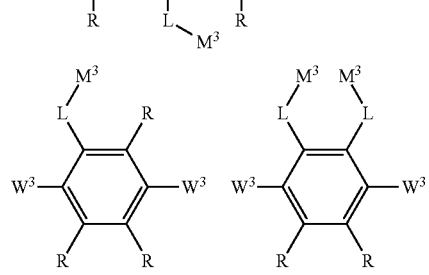
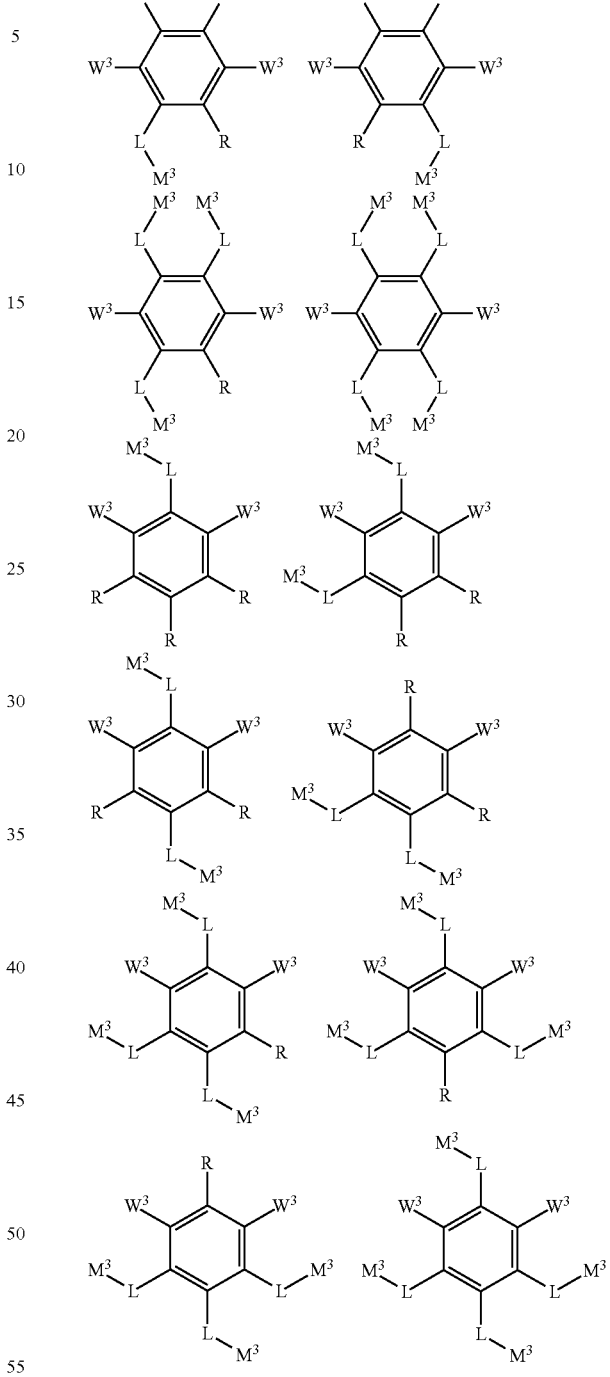

(wherein $W^3$, L, R, and $M^3$ are as defined above.)

EXAMPLES

Hereinafter, Examples will be shown in order to describe the present invention in more details, but the present invention will not be limited to these.

The polystyrene equivalent number average molecular weight and weight average molecular weight of the polymer compound were determined with size exclusion chromatography (SEC) (made by Shimadzu Corporation: LC-10Avp). A method shown in analysis condition 1 or analysis condition 2 below was used as an analysis condition for the SEC.

[Analysis Condition 1]

The polymer compound to be measured was dissolved in tetrahydrofuran so that the concentration thereof might be approximately 0.05% by weight, and 50 µL of the solution was injected to the SEC. Tetrahydrofuran was used as a mobile phase of the SEC to be flown at a flow rate of 0.6 mL/min. As a column, two of TSKgel SuperHM-H (made by Tosoh Corporation) and one TSKgel SuperH2000 (made by Tosoh Corporation) were connected in series, and used. A differential refractive index detector (made by Shimadzu Corporation: RID-10A) was used for a detector.

[Analysis condition 2]

The polymer compound to be measured was dissolved in tetrahydrofuran so that the concentration thereof might be approximately 0.05% by weight, and 10 µL of the solution was injected to the SEC. Tetrahydrofuran was used as a mobile phase of the SEC to be flown at a flow rate of 2.0 mL/min. As a column, a PLgel MIXED-B (made by Polymer Laboratories, Ltd.) was used. A UV-VIS detector (made by Shimadzu Corporation: SPD-10Avp) was used for a detector.

Measurement of LC-MS was performed by the following method. A sample to be measured was dissolved in chloroform or tetrahydrofuran so that the concentration thereof might be approximately 2 mg/mL, and approximately 1 µL of the solution was injected to a LC-MS (made by Agilent Technologies Inc., trade name: 1100LCMSD). As a mobile phase of the LC-MS, ion-exchanged water to which approximately 0.1% by weight of acetic acid was added and acetonitrile to which approximately 0.1% by weight of acetic acid was added were used while changing the proportion thereof. The mobile phase was flown at a flow rate of 0.2 mL/min. An L-column 2 ODS (3 µm) (made by Chemicals Evaluation and Research Institute, Japan, inner diameter: 2.1 mm, length: 100 mm, particle size of 3 µm) was used for a column.

Measurement of NMR was performed by the following method. 5 to 10 mg of a sample to be measured was dissolved in approximately 0.5 mL of deuterated chloroform, deuterated dimethyl sulfoxide, or deuterated tetrahydrofuran, and measured using an NMR (made by Varian Inc., trade name: MERCURY 300).

Synthesis Example 1

Synthesis of Metal Complex (MC-5)

[Synthesizing Method 1]
Synthesis of 5-bromo-2-phenylpyridine 2,5-dibromopyridine (7.11 g, 30 mmol), toluene (130 mL), phenylboric acid (4.57 g, 37.5 mmol), and tetrakis(triphenylphosphine)palladium(0) (1.73 g, 1.5 mmol) were weighed and placed into a reactor. A reactant was dissolved under a nitrogen stream while stirring at 50° C. To this, a 2 M sodium carbonate aqueous solution (30 mL) was added, and stirring was performed at 80° C. for 6 hours. An organic layer of the obtained reaction solution was collected, and washed with a sodium carbonate aqueous solution and a saturated brine. The organic layer was dried with sodium sulfate, filtered, and then distilled off. This residue was purified using silica gel column chromatography (hexane/toluene) to distill off the solvent, and 5-bromo-2-phenylpyridine (6.21 g, 26.5 mmol) was obtained.

Synthesis of Metal Complex (Complexes 1 and 2)

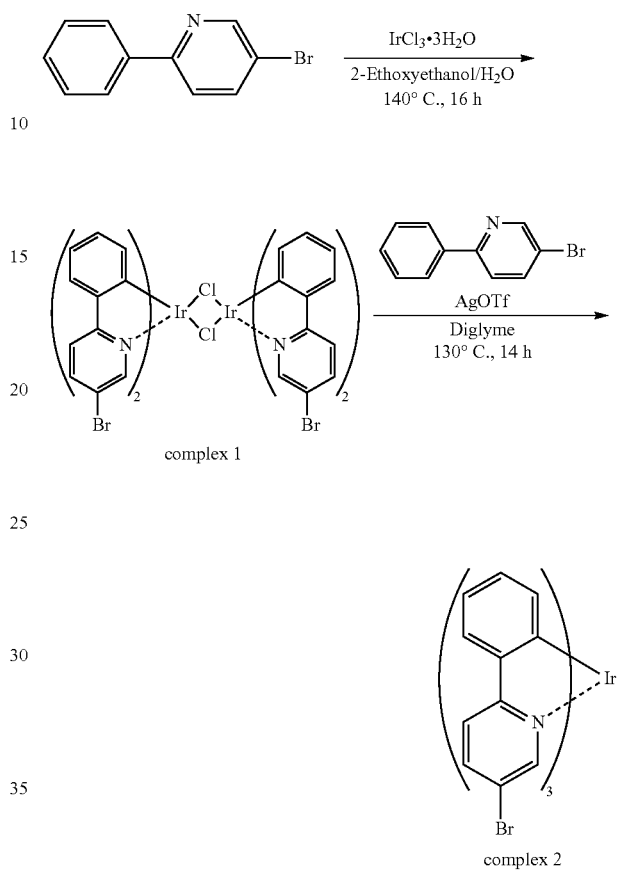

complex 1 complex 2

5-bromo-2-phenylpyridine (7.39 g, 30 mmol), iridium chloride trihydrate (4.76 g, 13.5 mmol), 2-ethoxyethanol (58 mL), and water (19 mL) were weighed and placed into a reactor, and heated at 140° C. under a nitrogen stream for 16 hours. After air cooling, the obtained reaction mixture was filtered, and washed with water, methanol, and hexane in this order. Thereby, a metal complex (complex 1, 9.10 g, 6.58 mmol) represented by the above-mentioned formula was obtained as a yellow solid.

A metal complex (complex 1, 6.94 g, 5.0 mmol), 5-bromo-2-phenylpyridine (7.32 g, 30.0 mmol), and diglyme (43 mL) were weighed and placed into a reactor. Silver trifluoromethanesulfonate (2.57 g, 10.0 mmol) was added, and the solution was stirred at 130° C. for 14 hours. The obtained reactant was filtered, and the solid was dissolved in methylene chloride (1.3 L). This solution was filtered, and the filtrate was condensed to approximately 150 mL By filtering and collecting the deposited solid and washing the deposited solid with hexane, a metal complex (complex 2, 6.35 g, 7.1 mmol) represented by the above-mentioned formula was obtained.

LC-MS (positive) m/z: 890 ([M+H]$^+$)

$^1$H NMR (300 MHz, DMSO-d$_6$)

δ 6.51 (d, J=7.8 Hz, 3H), δ 6.72 (m, 3H), δ 6.84 (m, 3H), δ 7.66 (d, J=2.0 Hz, 3H), δ 7.80 (d, J=7.8 Hz, 3H), δ 8.05 (dd, J=2.0, 8.8 Hz, 3H), δ 8.14 (d, J=8.8 Hz, 3H)

Synthesis of Metal Complex (Complex 3)

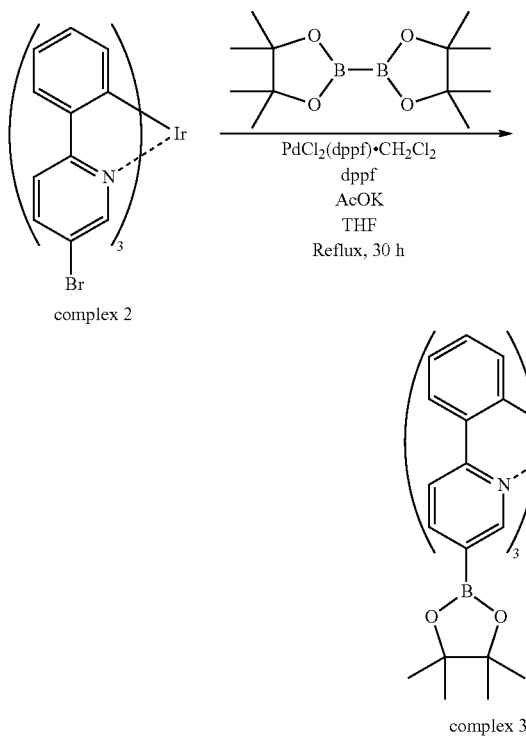

complex 2 complex 3

Under a nitrogen stream, a metal complex (complex 2, 3.27 g, 3.7 mmol), potassium acetate (3.27 g, 33.3 mmol), bis(pinacolato)diboron (3.38 g, 13.3 mmol), 1,1'-bis(diphenylphosphino)ferrocene (245 mg, 0.44 mmol), a [1,1'-bis(diphenylphosphino)ferrocene]dichloropalladium(II) dichloromethane adduct (361 mg, 0.44 mmol), and tetrahydrofuran (400 mL) were weighed, placed into a reactor, and refluxed for 30 hours. The obtained reaction solution was condensed, and dissolved by adding methylene chloride (150 mL) to the reaction solution. Subsequently, the solution was filtered. This filtrate was purified with silica gel chromatography (methylene chloride) to distill off the solvent, and a residue was washed with diethylether. Thereby, the metal complex (complex 3, 2.55 g, 2.47 mmol) represented by the above-mentioned formula was obtained.

LC-MS (positive) m/z: 1072 ([M+K]$^+$)

$^1$H NMR (300 MHz, CDCl$_3$)

δ 1.21 (s, 36H), δ 6.87 (m, 9H), δ 7.69 (d, J=7.7 Hz, 3H), δ 7.82 (s, 3H), δ 7.86 (m, 6H)

Synthesis of 4,6-bis(4-tert-butylphenyl)-2-chloro-1,3,5-triazine

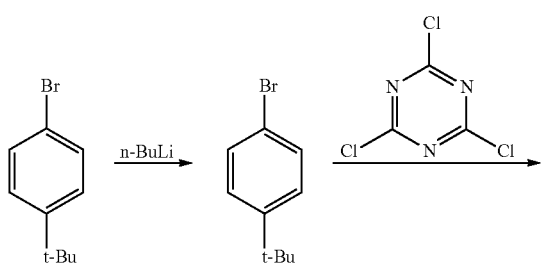

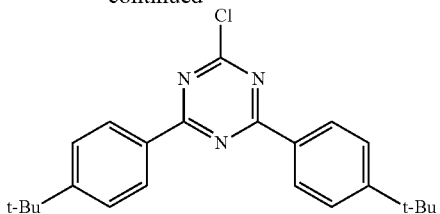

Under an argon stream, 1-bromo-4-tert-butylbenzene (125 g, 587 mmol) and tetrahydrofuran (470 mL) were charged in a reactor, and cooled to −70° C. An n-butyl lithium/hexane solution (1.6 M, 367 mL, 587 mmol) was dropped to this solution over 90 minutes at −70° C. After dropping was completed, the solution was stirred at −70° C. for 2 hours to obtain a 4-tert-butylphenyllithium/THF solution. Under an argon stream, cyanuric chloride (50.8 g, 276 mmol) and tetrahydrofuran (463 mL) were charged in another reactor, and cooled to −70° C. The 4-tert-butylphenyllithium/THF solution prepared previously was slowly dropped to this solution while the solution was cooled so that the reaction temperature might be not more than −60° C. After dropping was completed, the reaction solution was stirred at −40° C. for 4 hours, and stirred at room temperature for 4 hours. Water (50 mL) was added to this reaction mixture to complete the reaction, and tetrahydrofuran was distilled off. Water (1 L) and chloroform (2 L) were added to this residue, and an organic layer was extracted. The organic layer was further washed with water (1 L), and subsequently the solvent was distilled off. This residue was dissolved in acetonitrile (600 mL), and an insoluble solid was removed by filtration at the time of heating. The obtained filtrate was condensed to approximately 100 mL, and cooled to −70° C. to filter and collect the solid deposited. The collected solid was dissolved in a mixed solvent of chloroform (200 mL)/hexane (600 mL), and purified with silica gel column chromatography (developing solvent: chloroform/hexane). The solvent was distilled off, and this residue was recrystallized from acetonitrile. Thereby, 4,6-bis(4'-tert-butylphenyl)-2-chloro-1,3,5-triazine (41.3 g, 109 mmol) was obtained.

LC-MS (APPI, positive) m/z: 380 ([M+H]$^+$)

$^1$H NMR (300 MHz, CDCl$_3$)

δ1.39 (s, 18H), δ 7.56 (d, J=8.4 Hz, 4H), δ 8.54 (d, J=8.4 Hz, 4H)

Synthesis of Metal Complex (MC-5)

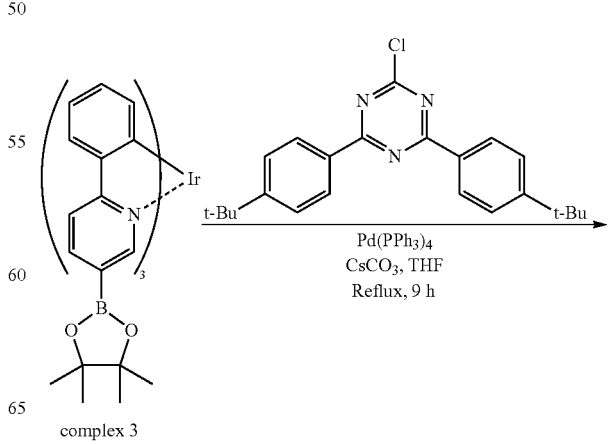

complex 3

-continued

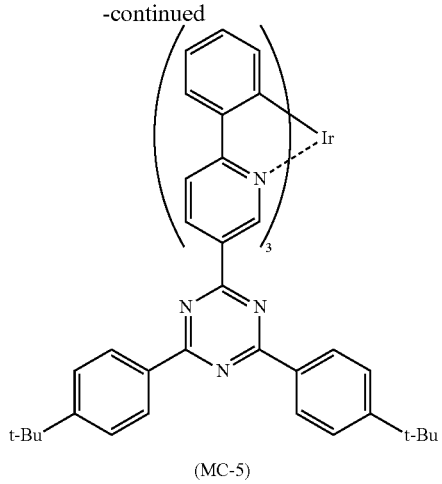

(MC-5)

Under a nitrogen stream, a metal complex (complex 3, 546 mg, 0.53 mmol), 4,6-bis(4-tert-butylphenyl)-2-chloro-1,3,5-triazine (702 mg, 1.85 mmol), cesium carbonate (1.73 g, 5.31 mmol), tetrakis(triphenylphosphine)palladium(0), (196 mg, 0.17 mmol), and tetrahydrofuran (53 mL) were weighed, placed into a reactor, and refluxed for 9 hours. The obtained reaction solution was condensed, and dissolved by adding toluene to this solution. This solution was filtered, and the filtrate was purified twice with silica gel chromatography (first developing solvent: toluene, second developing solvent: hexane/toluene=1/1). The solvent was distilled off, and the residue was washed with methanol. Thereby, the metal complex (MC-5, 257 mg, 0.15 mmol) represented by the above-mentioned formula was obtained.

LC-MS (APCI, positive) m/z: 1686 ([M+H]$^+$)

$^1$H NMR (300 MHz, CDCl$_3$)

δ 1.20 (s, 54H), δ 6.96 (m, 9H), δ 7.39 (d, J=8.4 Hz, 12H), δ 7.83 (d, J=7.5 Hz, 3H), δ 8.18 (d, J=8.4 Hz, 3H), δ 8.36 (d, J=8.4 Hz, 12H), δ 9.14 (d, J=8.4 Hz, 3H), δ 9.33 (s, 3H)

[Synthesizing Method 2]

The metal complex (MC-5) could be synthesized also by the following method.

Synthesis of Compound (L-2)

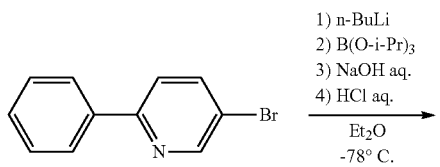

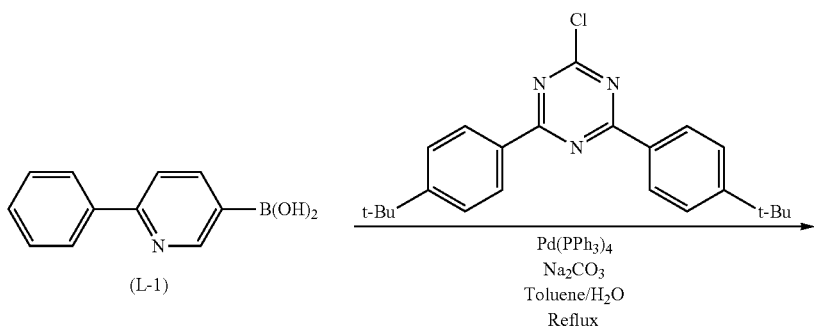

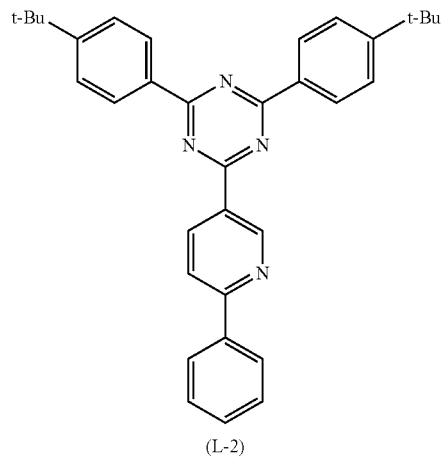

(L-2)

Under a nitrogen stream, 5-bromo-2-phenylpyridine (3.99 g, purity of 88%, 15 mmol) and 40 mL of dehydrated diethylether were weighed, placed into a reactor, and cooled to −78° C. An n-butyllithium/hexane solution (1.56 M, 11.5 mL, 18 mmol) was dropped to this solution over 15 minutes. After dropping was completed, the obtained reaction solution was stirred at −78° C. for 1 hour. Next, 3.39 g (18 mmol) of triisopropoxyborane was added, and the reaction solution was stirred at −78° C. for 1 hour and stirred at room temperature for 5 hours. The obtained reaction solution was cooled to 0° C., and hydrolyzed by slowly dropping 200 mL of a 5% by weight sodium hydroxide aqueous solution. An aqueous layer was recovered from the obtained reaction solution by liquid separation operation, and this aqueous layer was neutralized with 3N hydrochloric acid until the pH reached 7. Ethyl acetate (500 mL) was added to the obtained cloudy solution, and an organic layer was extracted. The solvent of this organic layer was distilled out, and the residue was washed with ether, thereby to obtain a compound (L-1, 2.53 g, 13 mmol).

4,6-bis(4'-tert-butylphenyl)-2-chloro-1,3,5-triazine (4.61 g, purity of 87%, 11 mmol), a compound (L-1, 2.43 g, 12 mmol), toluene (44 mL), and tetrakis(triphenylphosphine)palladium(0) (490 mg, 0.4 mmol) were weighed, and placed into a reactor. Under a nitrogen stream, a solid content was dissolved while the mixture was stirred at 50° C. A 2 M sodium carbonate aqueous solution (11 mL) was added to the thus-obtained solution, and the solution was refluxed for 9 hours. An organic layer of the obtained reaction solution was recovered, and washed with 50 mL of a sodium hydrogencarbonate aqueous solution (twice) and with 50 mL of a saturated brine (once). The organic layer was dried with sodium sulfate, and filtered. Subsequently, the solvent was distilled off. This residue was purified with silica gel column chromatography (hexane/toluene), and the solvent was distilled off. The residue was crystallized using a chloroform/ethanol solvent. The crystal was collected by filtration, and dried, thereby to obtain a compound (L-2, 3.09 g, 6.2 mmol).

LC-MS (APPI, positive) m/z: 499 ([M+H]$^+$)

$^1$H NMR (300 MHz, CDCl$_3$)

δ 1.42 (s, 18H), δ 7.52 (m, 3H), δ 7.62 (d, J=6.8 Hz, 4H), δ 7.95 (d, J=8.4 Hz, 1H), δ 8.16 (d, J=7.3 Hz, 2H), δ 8.69 (d, J=6.8 Hz, 4H), δ 9.04 (d, J=8.4 Hz, 1H), δ 10.02 (s, 1H).

Synthesis of Metal Complex (MC-5)

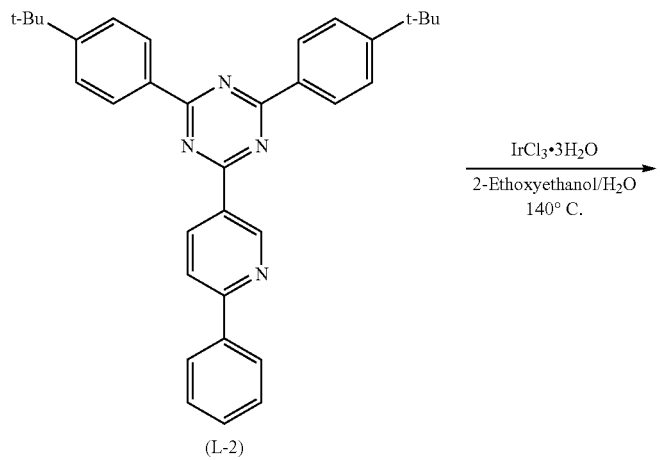

(L-2)

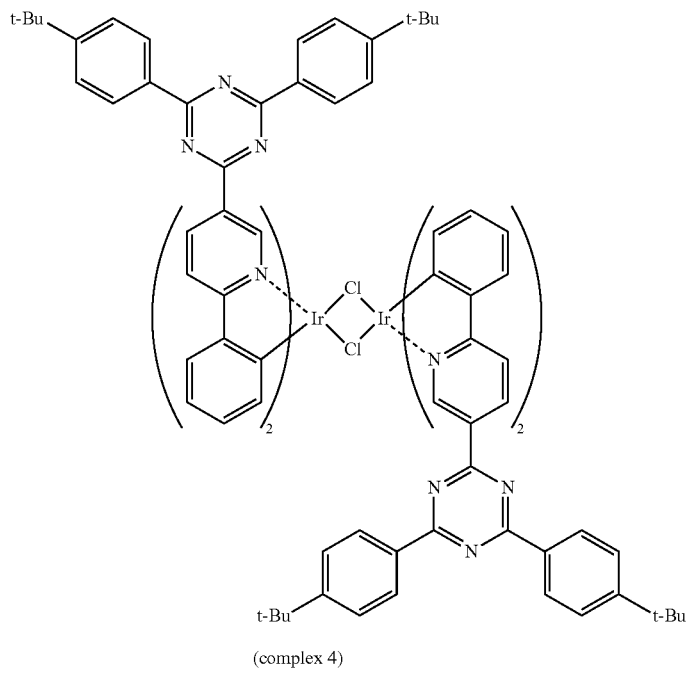

(complex 4)

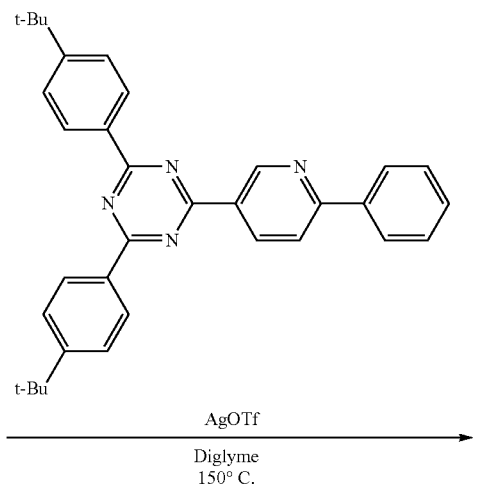

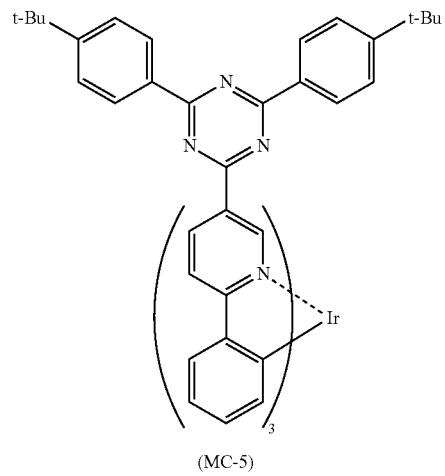

(MC-5)

A compound (L-2, 1.39 g, 2.8 mmol), iridium chloride trihydrate (425 mg, 1.2 mmol), 2-ethoxyethanol (7 mL), and water (2 mL) were weighed, and placed into a reactor. Under a nitrogen stream, the solution was heated at 140° C. for 9 hours. After air cooling, the obtained mixture was filtered, and the residue was washed in order of methanol (50 mL) and hexane (20 mL). Thereby, the metal complex (complex 4, 1.58 g) represented by the above-mentioned formula was obtained as a red solid.

A metal complex (complex 4, 1.48 g, 0.6 mmol), a compound (L-2, 1.46 g, 2.9 mmol), and diglyme (5 mL) were weighed, and placed into a reactor. Silver trifluoromethanesulfonate (313 mg, 1.2 mmol) was added, and the solution was stirred at 150° C. for 18 hours. The obtained reactant was filtered, and the solid was washed with methanol (100 mL). This solid was dissolved in toluene (40 mL), and the solution was purified with silica gel column chromatography (hexane/toluene) to distill off the solvent. The residue was washed with methanol, and crystallized in a toluene/acetonitrile solution. The obtained crystals were collected by filtration, and dried under reduced pressure. Thereby, the metal complex (MC-5, 1.00 g, 0.6 mmol) represented by the above-mentioned formula was obtained.

Example 1

Synthesis and Evaluation of Polymer Compound 1

Synthesis of Metal Complex (MC-6 and MC-7)

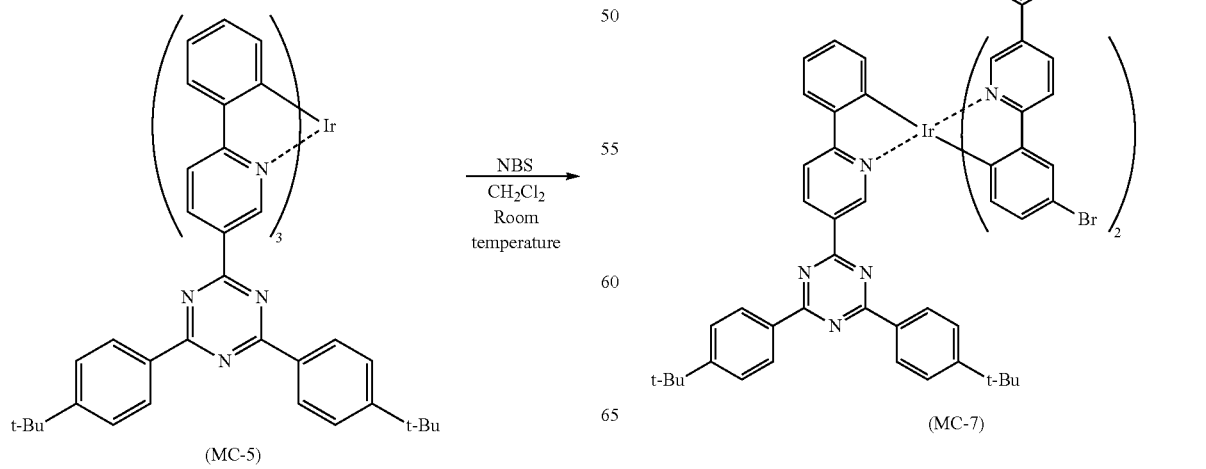

Under an argon stream, a metal complex (MC-5, 2.03 g, 1.20 mmol) obtained in synthesis example 1 and methylene chloride (200 mL) were weighed, and placed into a reactor. The metal complex was dissolved. N-bromosuccinimide (221 mg, 1.24 mmol) was added to this solution, and the solution was stirred at room temperature for 4 hours. The solvent was distilled off, and toluene (50 mL) was added to the residue to dissolve the residue. This toluene solution was purified with silica gel chromatography (developing solvent: toluene). The eluted solution was recovered, and the solvent was distilled off. Subsequently, a hexane/toluene (2/1) mixed solution (400 mL) was added to the residue to dissolve the residue. This solution was again purified with silica gel chromatography (developing solvent: hexane/toluene=2/1). The second eluted component was recovered, and the solvent was distilled off. Subsequently, the residue was washed with methanol. Thereby, the metal complex (MC-6, 1.55 g, 0.88 mmol) represented by the above-mentioned formula was obtained. Moreover, the first eluted component was recovered, and the solvent was distilled off. Subsequently, the residue was washed with methanol. Thereby, the metal complex (MC-7, 315 mg, 0.17 mmol) represented by the above-mentioned formula was obtained.

Metal Complex (MC-6)

LC-MS (APCI, positive) m/z: 1765 ([M+H]$^+$)

$^1$H NMR (300 MHz, CDCl$_3$)

δ 1.20 (s, 54H), δ 6.85-7.00 (m, 10H), δ 7.39 (d, J=7.8 Hz, 12H), δ 7.83 (d, J=7.3 Hz, 2H), δ 7.91 (s, 1H), δ 8.14 (d, J=8.8 Hz, 1H), δ 8.19 (d, J=8.6 Hz, 2H), δ 8.36 (d, J=7.8 Hz, 12H), δ 9.16 (m, 3H), δ 9.28 (s, 1H), δ 9.33 (s, 2H).

Metal Complex (MC-7)

LC-MS (APCI, positive) m/z: 1844 ([M+H]$^+$)

$^1$H NMR (300 MHz, CDCl$_3$)

δ 1.20 (s, 54H), δ 6.85 (dd, J=8.6, 9.0 Hz, 2H), δ 8.97 (m, 5H), δ 7.39 (d, J=8.1 Hz, 12H), δ 7.82 (d, J=7.5 Hz, 1H), δ 7.91 (s, 2H), δ 8.17 (m, 3H), δ 8.35 (d, J=8.1 Hz, 12H), δ 9.17 (m, 3 H), δ 9.28 (s, 2H), δ 9.32 (s, 1H).

Synthesis of Polymer Compound 1

Under an inert atmosphere, 2,7-bis(1,3,2-dioxaborolane-2-yl)-9,9-dioctylfluorene (0.53 g), 2,7-dibromo-9,9-dioctylfluorene (0.19 g), 2,7-dibromo-9,9-dihexylfluorene (0.20 g), bis(4-bromophenyl)-(4-sec-butylphenyl)-amine (0.092 g), a metal complex (MC-6) (0.18 g), Aliquat 336 (0.13 g, made by Sigma-Aldrich Corporation), bis(triphenylphosphine)palladium dichloride (0.7 mg), and toluene (26 ml) were mixed, and heated at 105° C. A 2 M Na$_2$CO$_3$ aqueous solution (10 ml) was dropped to this reaction solution, and the reaction solution was refluxed for 4 hours. After the reaction, phenylboric acid (0.12 g) was added to the solution, and the solution was heated at 105° C. again for 5 hours. After cooling, washing was performed with a 3% by weight acetic acid solution (20 ml) 3 times, and with water (20 ml) 3 times, and the solution was purified through an alumina column and a silica gel column. The obtained toluene solution was dropped to methanol (200 ml), followed by stirring for 1 hour. Then, the obtained solid was filtered and dried. Then, 250 mg of Polymer Compound 1 having the repeating units represented by the following formulas in the following mole ratio were obtained. The polystyrene equivalent weight average molecular weight (Mw) of Polymer Compound 1 measured on analysis condition 1 was 5.4×10$^4$, and the polystyrene equivalent number average molecular weight (Mn) was 3.1×10$^4$.

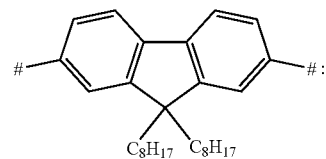

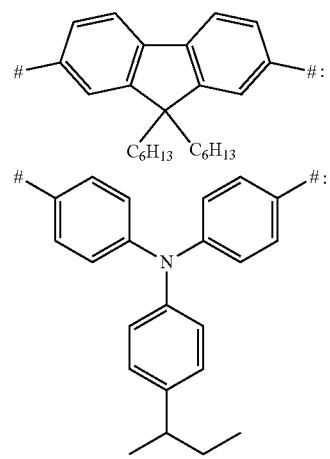

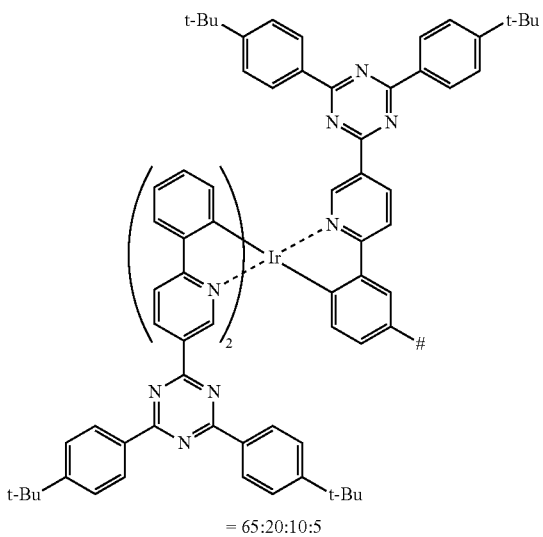

= 65:20:10:5

Properties of EL Light Emission of Polymer Compound 1

A 1.0% by weight xylene solution of Polymer Compound 1, and a 0.5% by weight xylene solution of Polymer I having the repeating units represented by the following formulas in the following mole ratio (polystyrene equivalent weight average molecular weight: 2.7×10$^5$, polystyrene equivalent number average molecular weight: 7.9×10$^4$) were prepared.

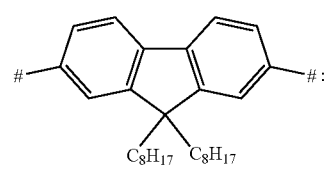

-continued

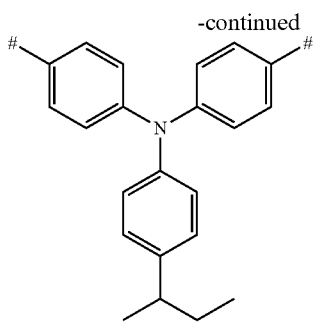

= 1:1

(wherein # represents a bond.)

Using a solution of poly(ethylenedioxythiophene)/polystyrene sulfonate (Bayer AG, trade name: Baytron P), a film of the solution was formed at a thickness of 65 nm by spin coating on a glass substrate to which an ITO film was attached at a thickness of 150 nm by a sputtering technique. The film was dried for 10 minutes at 200° C. on a hot plate. Next, using the xylene solution of Polymer I prepared above, a film was formed at a rotational speed of 2000 rpm by spin coating, and dried for 60 minutes at 180° C. under a nitrogen gas atmosphere. The temperature of this substrate was returned to room temperature. Then, using the xylene solution of Polymer Compound 1 prepared above, a film was formed at a rotational speed of 2000 rpm by spin coating. The average film thickness of the obtained film was approximately 80 nm. This film was dried for 10 minutes at 130° C. under a nitrogen gas atmosphere. Subsequently, as a cathode, approximately 5 nm of barium was vapor-deposited, and then, approximately 80 nm of aluminum was vapor-deposited to produce an EL device. After a degree of vacuum reached not more than $1 \times 10^{-4}$ Pa, vapor deposition of the metals was started. By applying voltage to the obtained EL device, red EL light emission having a peak at 605 nm was obtained. The device showed luminescence of 1000 cd/m$^2$ at approximately 10.5 V. The maximum luminous efficiency was 1.29 cd/A.

Example 2

Synthesis and Evaluation of Polymer Compound 2

Under an inert atmosphere, 2,7-bis(1,3,2-dioxaborolane-2-yl)-9,9-dioctylfluorene (0.53 g), 2,7-dibromo-9,9-dioctylfluorene (0.16 g), 2,7-dibromo-9,9-dihexylfluorene (0.20 g), bis(4-bromophenyl)-(4-secondarybutylphenyl)-amine (0.092 g), a metal complex (MC-7) (0.18 g), Aliquat 336 (0.13 g, made by Sigma-Aldrich Corporation), bis(triphenylphosphine)palladium dichloride (0.7 mg), and toluene (26 ml) were mixed, and heated to 105° C. A 2 M Na$_2$CO$_3$ aqueous solution (10 ml) was dropped to this reaction solution, and the reaction solution was refluxed for 4 hours. After the reaction, phenylboric acid (0.12 g) was added, and the reaction solution was again heated at 105° C. for 5 hours. After cooling, washing was performed with a 3% by weight acetic acid solution (20 ml) 3 times, and with water (20 ml) 3 times, and the solution was purified through an alumina column and a silica gel column. The obtained toluene solution was dropped to methanol (200 ml), followed by stirring for 1 hour. Subsequently, the obtained solid was filtered and dried. Then, 320 mg of Polymer Compound 2 having the repeating units represented by the following formulas in the following mole ratio was obtained. The polystyrene equivalent weight average molecular weight (Mw) of Polymer Compound 2 measured on analysis condition 1 was 3.8×10$^4$, and the polystyrene equivalent number average molecular weight (Mn) was 2.1×10$^4$.

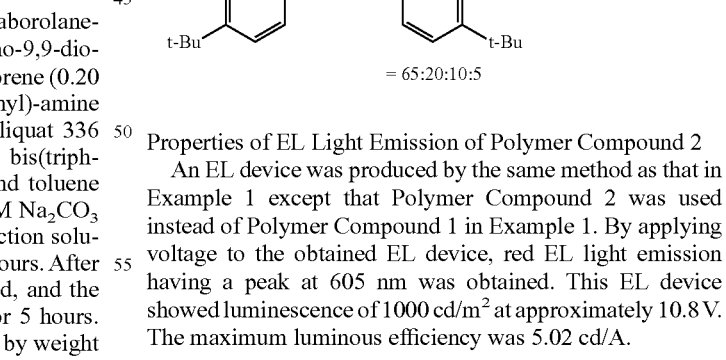

= 65:20:10:5

Properties of EL Light Emission of Polymer Compound 2

An EL device was produced by the same method as that in Example 1 except that Polymer Compound 2 was used instead of Polymer Compound 1 in Example 1. By applying voltage to the obtained EL device, red EL light emission having a peak at 605 nm was obtained. This EL device showed luminescence of 1000 cd/m$^2$ at approximately 10.8 V. The maximum luminous efficiency was 5.02 cd/A.

Example 3

Preparation and Evaluation of Composition A

Synthesis of Polymer Compound 3

Into a 200-mL separable flask to which a Dimroth condenser was connected, 1.93 g (3.6 mmol) of 9,9-dioctylfluorene-2,7-diboric acid ethylene glycol ester, 0.834 g (1.5 mmol) of 9,9-dioctyl-2,7-dibromofluorene, 0.829 g (1.7 mmol) of 9,9-dihexyl-2,7-dibromofluorene, 0.387 g (0.84 mmol) of N,N-bis(4-bromophenyl)-N-4-s-butylphenylamine, 0.52 g of methyltrioctylammonium chloride (trade name: Aliquat 336, made by Sigma-Aldrich Corporation), and 40 mL of toluene were placed. Under a nitrogen atmosphere, 2.8 mg of bistriphenylphosphinepalladium dichloride was added to the solution, and the solution was heated to 95° C. While 11 mL of a 17.5% by weight sodium carbonate aqueous solution was dropped to the obtained solution over 30 minutes, the solution was heated to 105° C., and subsequently, stirred at 105° C. for 3 hours. 21 mg (0.08 mmol) of 9,9-dioctylfluorene-2,7-diboric acid ethylene glycol ester was added, and the solution was stirred at 105° C. for 1 hour. Again, 21 mg (0.08 mmol) of 9,9-dioctylfluorene-2,7-diboric acid ethylene glycol ester was added, and the solution was stirred at 105° C. for 1 hour. Next, 40 mL of a toluene solution in which 46 mg of phenylboric acid was dissolved, and 2.8 mg of bistriphenylphosphinepalladium dichloride were added. Further, 11 mL of a 17.5% by weight sodium carbonate aqueous solution was dropped to the solution over 15 minutes, and the solution was stirred at 105° C. for 21 hours.

An aqueous layer was removed from the obtained solution. Then, 2.21 g of sodium N,N-diethyldithiocarbamate trihydrate and 43 mL of ion-exchanged water were added to the solution, and the solution was stirred at 85° C. for 2 hours. An organic layer was separated from the aqueous layer, and the organic layer was washed with 52 mL of ion-exchanged water (twice), 52 mL of a 3% by weight acetic acid aqueous solution (twice), and 52 mL of ion-exchanged water (twice) in this order.

The organic layer was dropped to 800 mL of methanol. After a precipitate was filtered, the precipitate was dried to obtain a solid. This solid was dissolved in 100 mL of toluene, and the solution was passed through a silica gel/alumina column through which toluene was passed in advance. Part of toluene in the filtrate was distilled off using a rotary evaporator. This solution was dropped to 400 mL of methanol, and a precipitate was filtered and dried. Then, 2.20 g of Polymer Compound 3 having the repeating units represented by the following formulas in the following mole ratio was obtained. The polystyrene equivalent number average molecular weight Mn of Polymer Compound 3 measured on analysis condition 1 was $2.0 \times 10^4$, and the polystyrene equivalent weight average molecular weight Mw was $3.9 \times 10^4$.

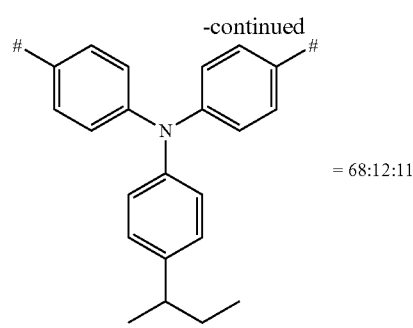

= 68:12:11

EL Light Emission Properties of Composition A

An EL device was produced by the same method as that in Example 1 except that a 1.0% by weight xylene solution of a mixture of Polymer Compound 1 (15 parts by weight) and Polymer Compound 3 (85 parts by weight), (the solution is referred to as "Composition A."), was used instead of the 1.0% by weight xylene solution of Polymer Compound 1 in Example 1. By applying voltage to the obtained device, red EL light emission having a peak at 600 nm was obtained. This device showed luminescence of 1000 cd/m² at approximately 6.9 V. The maximum luminous efficiency was 1.16 cd/A.

Example 4

Preparation and Evaluation of Composition B

EL Light Emission Properties of Composition B

An EL device was produced by the same method as that in Example 1 except that a 1.0% by weight xylene solution of a mixture of Polymer Compound 2 (15 parts by weight) and Polymer Compound 3 (85 parts by weight), (the solution is referred to as "Composition B."), was used instead of the 1.0% by weight xylene solution of Polymer Compound 1 in Example 1. By applying voltage to the obtained element, red EL light emission having a peak at 600 nm was obtained. This element showed luminescence of 1000 cd/m² at approximately 7.5 V. The maximum luminous efficiency was 1.25 cd/A.

Example 5

Synthesis of Metal Complex (MC-9)

Synthesis of Compound M-1

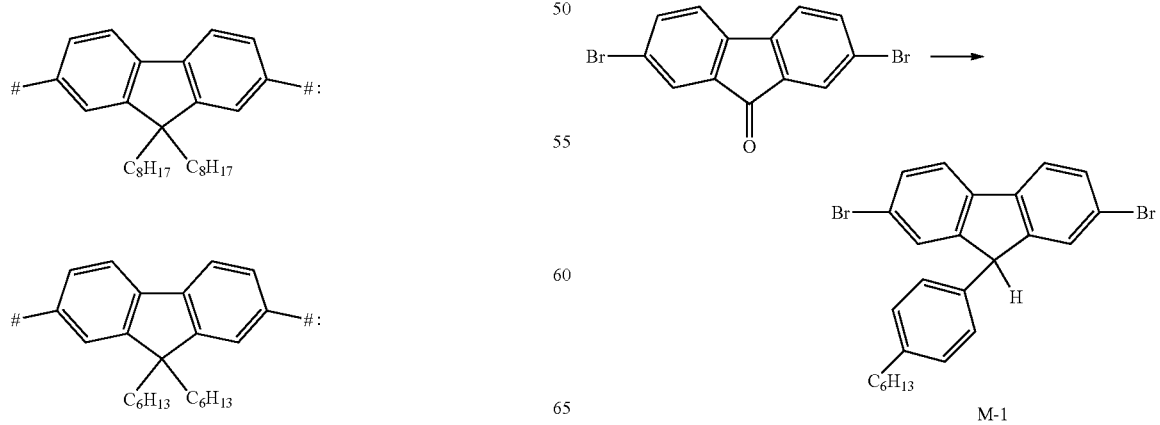

Under a nitrogen gas atmosphere, 2,7-dibromofluorenone (75 g, 0.22 mol), hexylbenzene (334 ml, 1.78 mol), and trifluoromethanesulfonic acid (42 ml) were stirred at room temperature, and sodium mercaptosulfonate (8.1 g, 44 mmol) was added to the solution, followed by stirring at 45° C. for 9 hours. The obtained solution was cooled to room temperature, and then, and poured into 1 L of hexane. Excessive hexylbenzene was distilled off by distillation under reduced pressure (105.5° C., 20 hPa), and the solution was diluted with hexane. Subsequently, the solution was poured into methanol, and 2,7-dibromofluorenone deposited was removed by filtration. The obtained filtrate was condensed, and diluted with toluene. Isopropyl alcohol was added to deposit a solid. The obtained solid was recrystallized with toluene/isopropyl alcohol thereby to obtain Compound M-1 (53 g, yield of 49%) of white crystals.

$^1$H-NMR (300 MHz, CDCl$_3$) δ 0.88 (t, 3H), 1.20-1.45 (m, 6H), 1.54-1.62 (m, 2H), 2.57 (t, 2H), 4.96 (s, 1H), 6.94 (d, 2H), 7.10 (d, 2H), 7.42 (s, 2H), 7.48 (dd, 2H), 7.60 (d, 2H).

Synthesis of Compound M-2

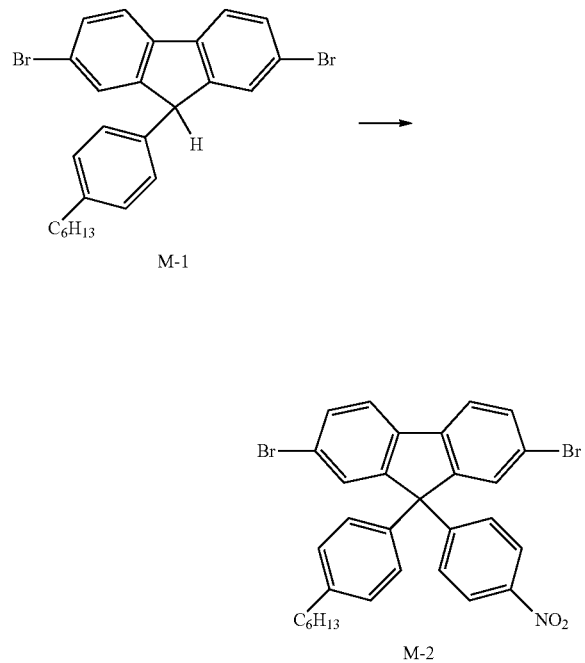

Under a nitrogen gas atmosphere, Compound M-1 (10 g, 20.6 mmol), 4-fluoronitrobenzene (3.5 g, 24.8 mmol), and potassium carbonate (4.3 g, 31.0 mmol) were stirred under heating reflux in dehydrated N,N-dimethylformamide (35 ml) for 6 hours. After the obtained solution was cooled to room temperature, 300 ml of water was slowly added to the obtained solution while the obtained solution was stirred. The solution was stirred at room temperature as it was overnight. The deposited solid was collected by filtration under reduced pressure, and further the solid on a filter was washed with water. The obtained solid was dried in a vacuum to obtain Compound M-2 (13.6 g).

$^1$H-NMR (300 MHz, THF-d8) δ 0.91 (t, 3H), 1.24-1.42 (m, 6H), 1.55-1.61 (m, 2H), 2.59 (t, 2H), 7.07-7.16 (m, 4H), 7.43 (d, 2H), 7.59 (dd, 2H), 7.64 (s, 2H), 7.82 (d, 2H), 8.11 (d, 2H).

Synthesis of Compound M-3

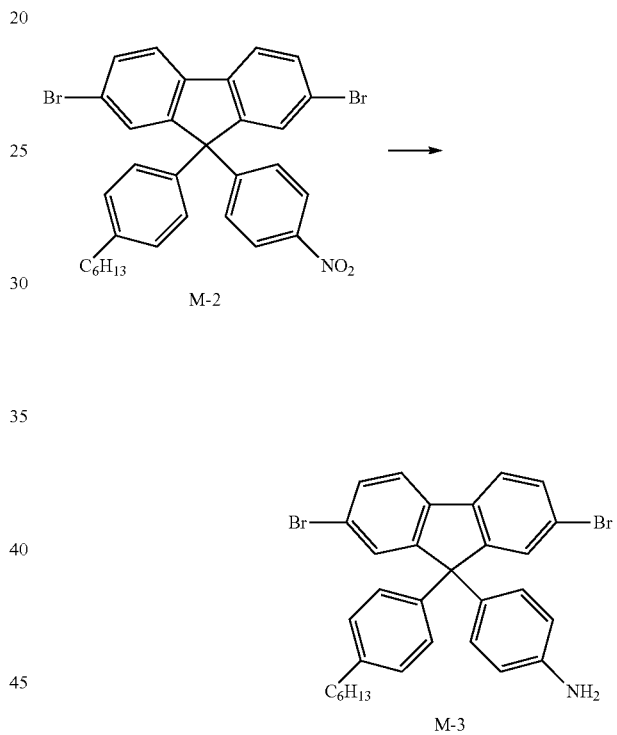

Under a nitrogen gas atmosphere, a mixture of Compound M-2 (12.9 g, 21 mmol), ethanol (153 ml), and tin(II) chloride dihydrate (18.6 g, 8 mmol) was stirred under heating reflux for 6 hours. The solution was cooled to room temperature, and then, was concentrated under reduced pressure until the weight of the solution reached approximately 60 g. The obtained solution was added to ice water (150 g) while stirring. After the ice dissolved, a 40% by weight sodium hydroxide aqueous solution was added to the obtained aqueous solution until the pH of the solution exceeded 10. Then, extraction with 200 ml of toluene was performed twice. The obtained organic layer was dried with anhydrous sodium sulfate, condensed under reduced pressure, and recrystallized (toluene-hexane) to obtain Compound M-3 (10 g, yield of 97%).

$^1$H-NMR (300 MHz, CDCl$_3$) δ 0.87 (t, 3H), 1.20-1.40 (m, 6H), 1.52-1.57 (m, 2H), 2.54 (t, 2H), 6.54 (d, 2H), 6.91 (d, 2H), 7.02-7.06 (m, 4H), 7.42-7.48 (m, 4H), 7.54 (d, 2H).

LC-MS (APPI, positive) m/z$^+$=574 [M+H]$^+$.

Synthesis of Compound M-4

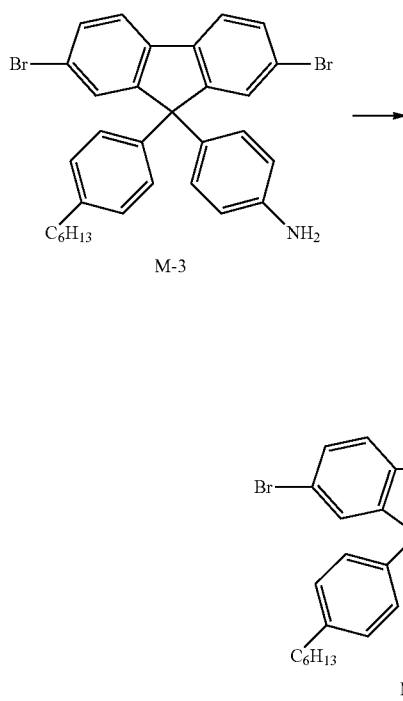

50 g (87 mmol) of Compound M-3 was prepared in a 3-L Erlenmeyer flask. While Compound M-3 was stirred, 21.7 ml of concentrated hydrochloric acid was slowly added. After 100 ml of water was added there, 2 L of acetonitrile was added to prepare the solution, and the solution was cooled to 0° C. using an ice bath. An aqueous solution obtained by dissolving 6.4 g (93 mmol) of sodium nitrite with 20 ml of water was slowly added to the obtained solution, and stirred at 0° C. for 30 minutes (this is referred to as "Solution a.").

18.4 g (133 mmol) of potassium carbonate and 12.8 g (174 mmol) of diethylamine were prepared in another 3-L Erlenmeyer flask. To the flask, 128 ml of water was added, and the solution was stirred at 0° C. (this is referred to as "Solution b.").

Solution a was slowly added to Solution b while stirring, and the mixed solution was further stirred at 0° C. for 30 minutes. Subsequently, the ice bath was removed, and stirring was performed at room temperature for 1 hour. The obtained reaction solution was extracted with 3 L of chloroform, and dried with anhydrous sodium sulfate. Then, the solution was concentrated until chloroform was distilled off. With silica gel column chromatography (1 L of silica gel, 6 cm in diameter of the column×60 cm in height of the column, eluant (hexane:chloroform=10:1 (volume ratio))), the obtained mixture was purified to obtain 51 g of a target Compound M-4 at a yield of 89%.

$^1$H-NMR (300 MHz, THF-$d_8$) δ 7.80 (d, J=8.13 Hz, 2H), 7.62 (d, J=1.74 Hz, 2H), 7.56 (dd, J=8.10 Hz and 1.74 Hz, 2H), 7.27-7.34 (m, 2H), 7.08-7.17 (m, 6H), 3.79 (q, J=7.14 Hz, 4H), 2.61 (m, 2H), 1.57-1.70 (m, 2H), 1.32-1.46 (m, 6H), 1.18-1.32 (m, 6H), 0.94 (t, J=6.57 Hz, 3H).

Synthesis of Compound M-5

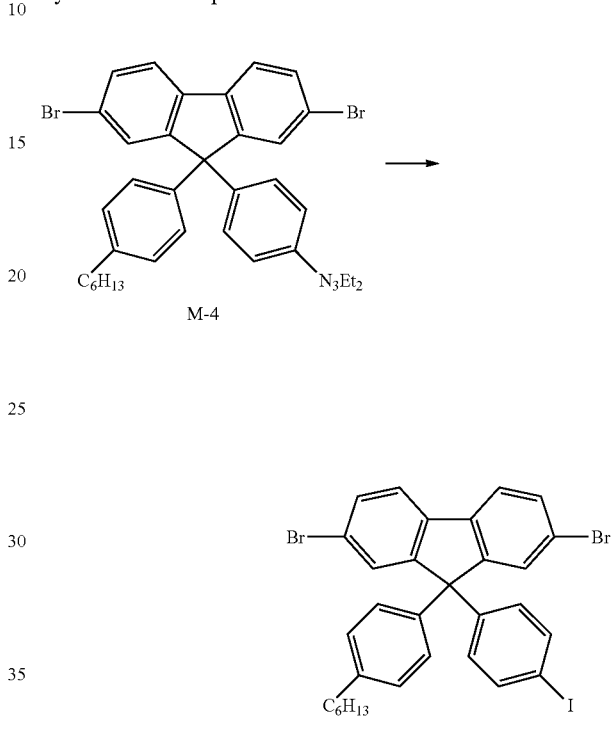

A stirring bar was mounted on a 1-L one-neck Kieldahl flask, and 51 g (77 mmol) of Compound M-4, 39.2 g (154 mmol) of iodine, and 500 ml (8 mol) of methyl iodide were added. Bubbling of an argon gas was performed while the solution was stirred for 15 minutes. The solution was stirred under nitrogen atmosphere for 6 hours while the solution was heated in an oil bath at 90° C. Subsequently, the solvent was distilled off. A solution was prepared by adding 500 ml of chloroform to the flask, filtered with a glass filter (diameter: 7.5 cm) covered with 250 ml of silica gel, and washed with 1 L of chloroform. The obtained chloroform solution was washed with a saturated sodium thiosulfate aqueous solution, dried with anhydrous sodium sulfate, and condensed. The obtained mixture was purified with silica gel column chromatography (1 L of silica gel, 6 cm in diameter of the column×60 cm in height of the column, eluant (hexane:chloroform=10:1 (volume ratio))). Further, reprecipitation from a hexane-ethanol mixed solvent was performed. Thereby, 34.6 g of a target Compound M-5 was obtained as a white solid at a yield of 67%.

$^1$H-NMR (300 MHz, CDCl$_3$) δ7.54-7.62 (m, 3H), 7.43-7.52 (m, 4H), 7.22-7.52 (m, 1H), 7.13 (d, J=7.41 Hz, 1H), 6.98-7.10 (m, 4H), 6.89 (d, J=7.53 Hz, 1H), 2.56 (t, J=8.01 Hz, 2H), 1.58 (br, 2H), 1.20-1.40 (br, 6H), 0.89 (t, J=5.64 Hz, 3H).

LC-MS (APPI, positive) m/z$^+$=684 [M$^-$]$^+$.

Synthesis of Metal Complex (MC-8)
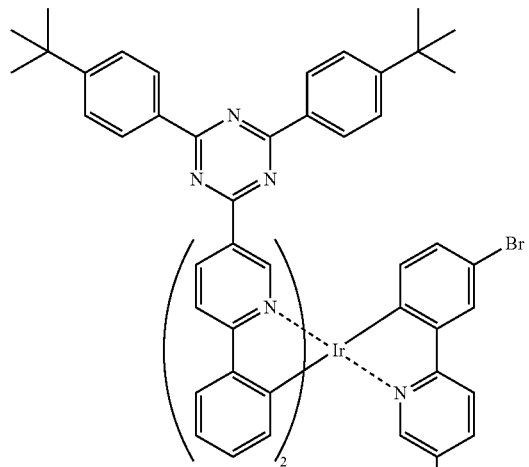
(MC-6)
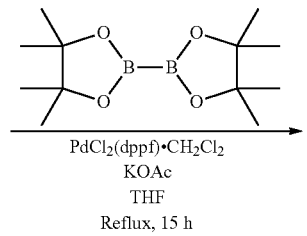
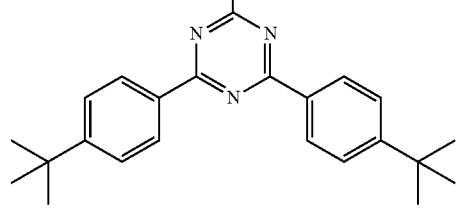
PdCl$_2$(dppf)·CH$_2$Cl$_2$
KOAc
THF
Reflux, 15 h
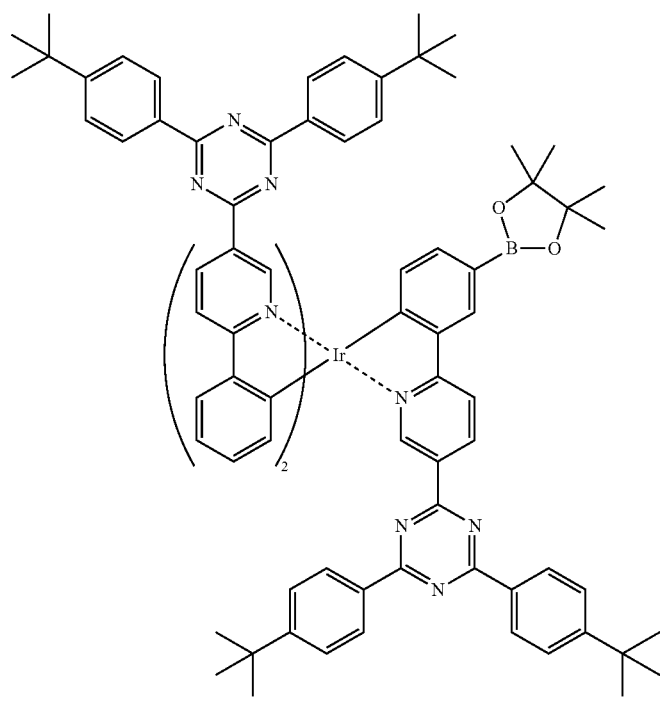
(MC-8)

Under an argon stream, a metal complex (MC-6, 4.60 g, 2.5 mmol), potassium acetate (0.75 g, 7.6 mmol), bis(pinacolato) diboron (0.96 g, 3.8 mmol), a [1,1'-bis(diphenylphosphino) ferrocene]dichloropalladium(II) dichloromethane adduct (0.13 g, 0.15 mmol), and tetrahydrofuran (167 mL) were weighed, placed into a reactor, and refluxed for 15 hours. The obtained reaction solution was condensed, and dissolved by adding a hexane/toluene (2/1 (volume ratio)) mixed solution (400 mL). The obtained solution was purified with silica gel chromatography (developing solvent: hexane/toluene=1/1 (volume ratio)). The solvent was distilled off, and the residue was washed with methanol. Thereby, the metal complex (MC-8, 3.67 g, 2.0 mmol) represented by the above-mentioned formula was obtained.

$^1$H NMR (300 MHz, r.t., CHCl$_3$)

δ 1.20 (s, 36 H), δ 1.22 (s, 18 H), δ 1.30 (s, 12 H), δ 6.87-7.01 (m, 6 H), δ 7.09 (d, J=7.8 Hz, 1H), δ 7.29 (d, J=7.8 Hz, 1 H), δ 7.40 (d, J=8.1 Hz, 12 H), δ 7.82 (d, J=7.2 Hz, 2 H), δ 8.18 (dd, J=3.3, 8.4 Hz, 2 H), δ 8.27 (s, 1 H), δ 8.36 (d, J=7.8 Hz, 12 H), δ 9.14 (d, J=8.4 Hz, 3 H), δ 9.30 (s, 2 H), δ 9.32 (s, 1 H).

LC-MS (APCI, positive) m/z: 1812 ([M+H]$^+$)

Synthesis of Metal Complex (MC-9)

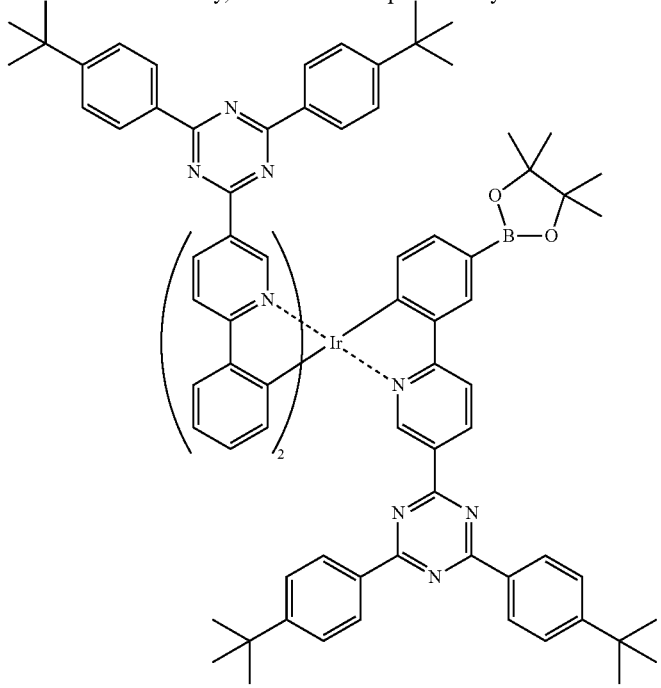

(MC-8)

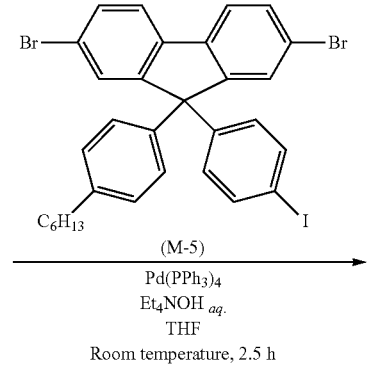

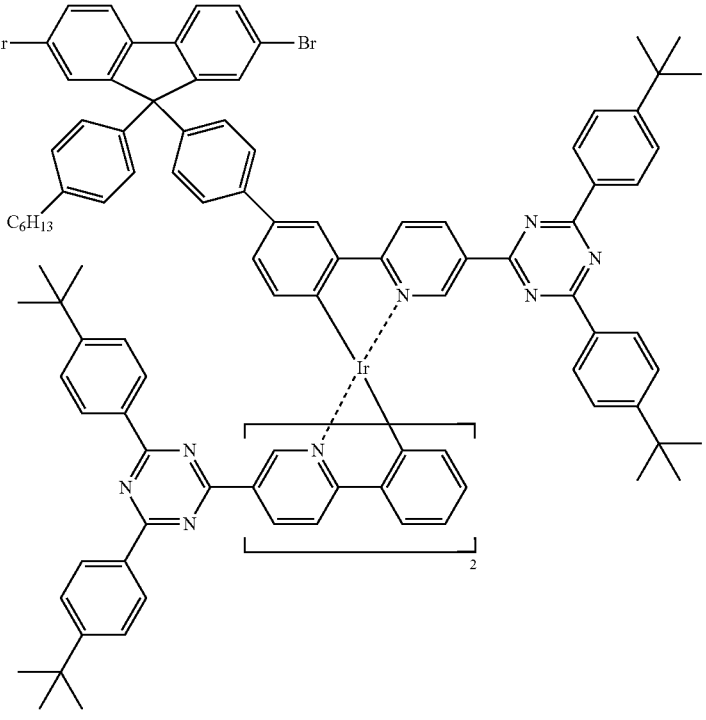

(MC-9)

Under an argon stream, a metal complex (MC-8, 2.71 g, 1.5 mmol), a compound (M-5, 1.05 g, 1.5 mmol), a 20% by weight aqueous solution of hydroxide tetraethylammonium (2.64 g, 3.6 mmol), tetrakis(triphenylphosphine)palladium (0) (61 mg, 0.05 mmol), and tetrahydrofuran (60 mL) were weighed, placed into a reactor, and stirred at room temperature for 2.5 hours. The obtained reaction solution was condensed, and dissolved by adding a hexane/toluene (1.5/1 (volume ratio)) mixed solution (150 mL). The obtained solution was dried with sodium sulfate, and the solution was filtered. The filtrate was purified with silica gel chromatography (developing solvent: hexane/toluene=1.5/1 (volume ratio)). The solvent was distilled off, and the residue was washed with methanol. Thereby, the metal complex (MC-9, 2.59 g, 1.2 mmol) represented by the above-mentioned formula was obtained.

$^1$H NMR (300 MHz, r.t., CHCl$_3$)

δ 0.88 (m, 3 H), δ 1.20 (s, 54 H), δ 1.26-1.29 (m, 6 H), δ 1.58 (br, 2 H), δ 2.55 (t, J=7.6 Hz, 2 H), δ 6.91-7.16 (m, 14 H), δ 7.39 (d, J=8.4 Hz, 12 H), δ 7.44-7.58 (m, 8 H), δ 7.83 (m, 2 H), δ 7.99 (s, 1 H), δ 8.19 (d, J=8.7 Hz, 2 H), δ 8.24 (d, J=8.4 Hz, 1 H), δ 8.36 (d, J=8.4 Hz, 12 H), δ 9.15 (d, J=8.6 Hz, 3 H), δ 9.34 (s, 3 H).

LC-MS (APCI, positive) m/z: 2245 ([M+H]$^+$)

Example 6

Synthesis and Evaluation of Polymer Compound 4

Synthesis of Polymer Compound 4

Into a 200-mL three-neck flask to which a Dimroth condenser was connected, 1.06 g (2.0 mmol) of 9,9-dioctylfluorene-2,7-diboric acid ethylene glycol ester, 0.99 g (1.8 mmol) of 9,9-dioctyl-2,7-dibromofluorene, 0.15 g (0.20 mmol) of N,N'-bis(4-bromophenyl)-N,N'-bis(2,6-dimethyl-4-tert-butylphenyl)-1,4-phenylenediamine, a metal complex (MC-6, 89 mg, 0.05 mmol), 0.26 g of methyltrioctylammonium chloride (trade name: Aliquat 336, made by Sigma-Aldrich Corporation), and 20 mL of toluene were placed. Under a nitrogen atmosphere, 1.4 mg of bis(triphenylphosphine)palladium (II) dichloride was added to the solution, and the solution was heated to 85° C. While 5.4 mL of a 17.5% by weight sodium carbonate aqueous solution was dropped to the obtained solution, the solution was heated to 105° C.; subsequently, the solution was stirred at 105° C. for 6 hours. Next, 0.24 g of phenylboric acid, 1.7 mg of bis(triphenylphosphine)palladium(II) dichloride, and 20 mL of toluene were added, and the solution was stirred at 105° C. for 14 hours.

1.22 g of sodium N,N-diethyldithiocarbamate trihydrate and 12 mL of ion-exchanged water were added to the obtained solution, and the solution was stirred at 85° C. for 3 hours. 62 mL of toluene was added to the solution, and an organic layer was separated from an aqueous layer. Subsequently, the organic layer was washed with 26 mL of ion-exchanged water (twice), 26 mL of a 3% by weight acetic acid aqueous solution (twice), and 26 mL of ion-exchanged water (twice) in this order. The organic layer after washed was dropped to 330 mL of methanol to precipitate a polymer, followed by stirring the polymer for 1 hour. Subsequently, the obtained precipitate was filtered, and dried to obtain a solid. This solid was dissolved in 62 mL of toluene, and the solution was passed through a silica gel/alumina column through which toluene was passed in advance. The obtained solution was dropped to 350 mL of methanol, and the solution was stirred for 1 hour. The obtained solid was filtered, and dried. Then, 1.34 g of Polymer Compound 4 having the repeating units represented by the following formulas in the following mole ratio was obtained. The polystyrene equivalent weight average molecular weight (Mw) of Polymer Compound 4 measured on analysis condition 2 was 1.5×10$^5$, and the polystyrene equivalent number average molecular weight (Mn) was 5.7×10$^4$.

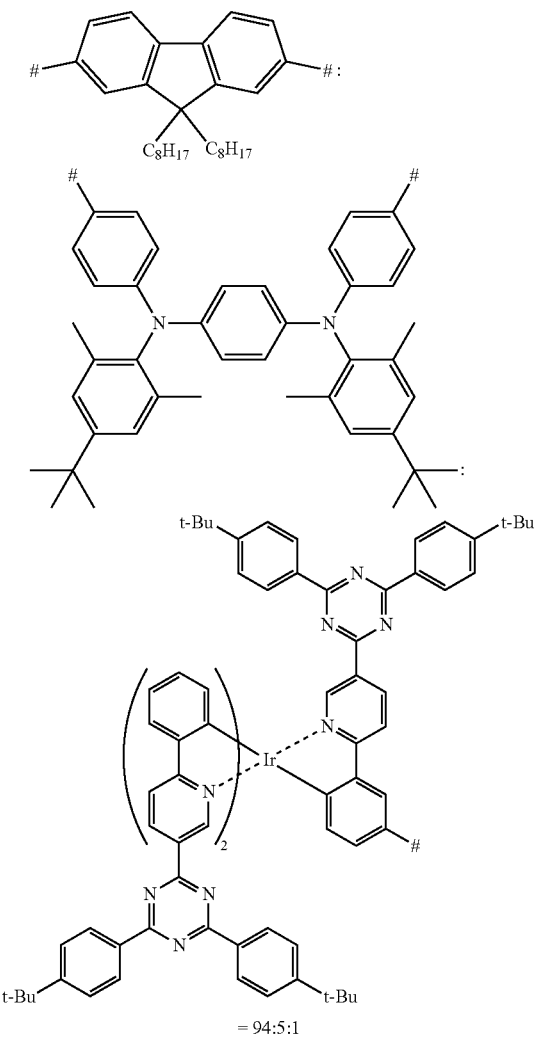

Properties of EL Light Emission of Polymer Compound 4

An EL device was produced by the same method as that in Example 1 except that Polymer Compound 4 was used instead of Polymer Compound 1 in Example 1, and a solution of poly(ethylenedioxythiophene)/polystyrene sulfonate made by H. C. Starck GmbH (trade name: CLEVIOS P AI4083) was used instead of that made by Bayer AG (trade name: Baytron P). By applying voltage to the obtained EL device, red EL light emission having a peak at 605 nm was obtained. This EL device showed luminescence of 1000 cd/m$^2$ at approximately 10.2 V. The maximum luminous efficiency was 8.05 cd/A.

Example 7

Synthesis and Evaluation of Polymer Compound 5

Synthesis of Polymer Compound 5

Into a 200-mL three-neck flask to which a Dimroth condenser was connected, 1.06 g (2.0 mmol) of 9,9-dioctylfluorene-2,7-diboric acid ethylene glycol ester, 1.00 g (1.8 mmol) of 9,9-dioctyl-2,7-dibromofluorene, 0.15 g (0.20 mmol) of N,N'-bis(4-bromophenyl)-N,N'-bis(2,6-dimethyl-4-tert-butylphenyl)-1,4-phenylenediamine, a metal complex (MC-9, 85 mg, 0.04 mmol), 0.26 g of methyltrioctylammonium chloride (trade name: Aliquat 336, made by Sigma-Aldrich Corporation), and 20 mL of toluene were placed. Under an nitrogen atmosphere, 1.4 mg of bis(triphenylphosphine)palladium (II) dichloride was added to the solution, and the solution was heated to 85° C. While 5.4 mL of a 17.5% by weight sodium carbonate aqueous solution was dropped to the obtained solution, the solution was heated to 105° C.; subsequently, the solution was stirred for 4.5 hours. Next, 0.25 g of phenylboric acid, 1.5 mg of bis(triphenylphosphine)palladium(II) dichloride, and 20 mL of toluene were added, and the solution was stirred at 105° C. for 12 hours.

1.22 g of sodium N,N-diethyldithiocarbamate trihydrate and 12 mL of ion-exchanged water were added to obtained solution, and the solution was stirred at 85° C. for 2 hours. By adding 62 mL of toluene to the solution, an organic layer was separated from an aqueous layer. Subsequently, the organic layer was washed with 26 mL of ion-exchanged water (twice), 26 mL of a 3% by weight acetic acid aqueous solution (twice), and 26 mL of ion-exchanged water (twice) in this order.

When the organic layer after washed was dropped to 360 mL of methanol, precipitation occurred; and stirring was continued for 2 hours. Next, the precipitate was filtered, and dried to obtain a solid. This solid was dissolved in 110 mL of toluene, and the solution was passed through a silica gel/alumina column through which toluene was passed in advance. The obtained solution was dropped to 600 mL of methanol, and the solution was stirred for 1 hour. Subsequently, the obtained solid was filtered, and dried. Then, 1.37 g of Polymer Compound 5 having the repeating units represented by the following formulas in the following mole ratio was obtained. The polystyrene equivalent weight average molecular weight (Mw) of Polymer Compound 5 measured on analysis condition 2 was $2.1 \times 10^5$, and the polystyrene equivalent number average molecular weight (Mn) was $8.7 \times 10^4$.

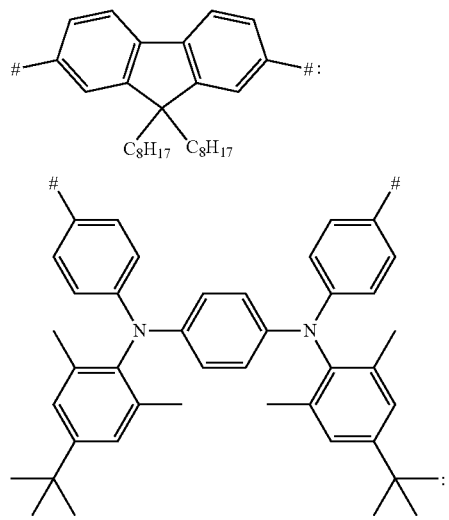

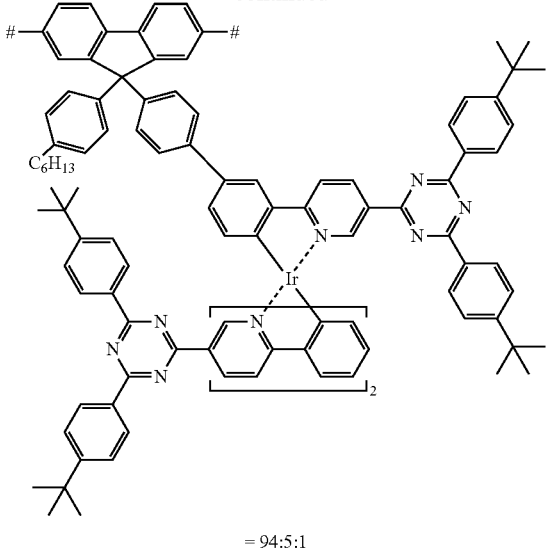

= 94:5:1

Properties of EL Light Emission of Polymer Compound 5

An EL device was produced by the same method as that in Example 1 except that Polymer Compound 5 was used instead of Polymer Compound 1 in Example 1, and a solution of poly(ethylenedioxythiophene)/polystyrene sulfonate made by H. C. Starck GmbH (trade name: CLEVIOS P AI4083) was used instead of that made by Bayer AG (trade name: Baytron P). By applying voltage to the obtained EL device, red EL light emission having a peak at 605 nm was obtained. This EL device showed luminescence of 1000 cd/m² at approximately 10.9 V. The maximum luminous efficiency was 8.99 cd/A.

Comparative Example 1

Synthesis and Evaluation of Polymer Compound 6

Synthesis of Polymer Compound 6

Metal Complex MC-10 was synthesized by a method described in JP 2004-531485 A.

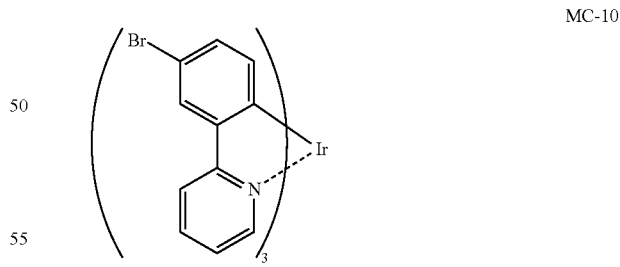

MC-10

Into a 200-mL three-neck flask to which a Dimroth condenser was connected, 1.06 g (2.0 mmol) of 9,9-dioctylfluorene-2,7-diboric acid ethylene glycol ester, 0.95 g (1.8 mmol) of 9,9-dioctyl-2,7-dibromofluorene, 0.14 g (0.19 mmol) of N,N'-bis(4-bromophenyl)-N,N'-bis(2,6-dimethyl-4-tert-butylphenyl)-1,4-phenylenediamine, a metal complex (MC-10, 111 mg, 0.12 mmol), 0.26 g of methyltrioctylammonium chloride (trade name: Aliquat 336, made by Sigma-Aldrich Corporation), and 20 mL of toluene were placed. Under a nitrogen atmosphere, 1.5 mg of bis(triphenylphosphine)palladium(II) dichloride was added to the solution, and the solution was heated to 85° C. While 5.4 mL of a 17.5% by weight sodium carbonate aqueous solution was dropped to the obtained solution, the solution was heated to 105° C. Subsequently, the solution was stirred for 4 hours. 1.7 mg of bis (triphenylphosphine)palladium(II) dichloride was added to the solution, and the solution was further stirred at 105° C. for 4.5 hours. Next, 0.24 g of phenyl boric acid, 1.5 mg of bis (triphenylphosphine)palladium(II) dichloride, and 20 mL of toluene were added to the obtained solution, and the solution was stirred at 105° C. for 12 hours.

1.22 g of sodium N,N-diethyldithiocarbamate trihydrate and 12 mL of ion-exchanged water were added to the solution, and the solution was stirred at 85° C. for 3 hours. An organic layer was separated from an aqueous layer by adding 62 mL of toluene to the obtained solution. Subsequently, the organic layer was washed with 26 mL of ion-exchanged water (twice), 26 mL of a 3% by weight acetic acid aqueous solution (twice), and 26 mL of ion-exchanged water (twice) in this order. The organic layer after washed was condensed to approximately 20 mL, and this condensed organic layer was dropped to 400 mL of methanol. Then, a precipitate was produced; stirring was continued for 1 hour. Next, the precipitate was filtered, and dried to obtain a solid. This solid was dissolved in 62 mL of toluene, and the solution was passed through a silica gel/alumina column through which toluene was passed in advance. This solution was condensed to approximately 30 mL, and the condensed solution was dropped to 400 mL of methanol to precipitate a polymer. After the polymer was stirred for 1 hour, the obtained solid was filtered, and dried. Then, 1.13 g of Polymer Compound 6 having the repeating units represented by the following formulas in the following mole ratio was obtained. The polystyrene equivalent weight average molecular weight (Mw) of Polymer Compound 6 measured on analysis condition 2 was $3.2 \times 10^4$, and the polystyrene equivalent number average molecular weight (Mn) was $1.0 \times 10^4$.

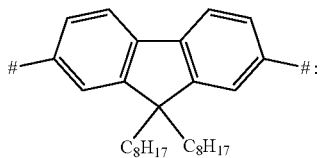

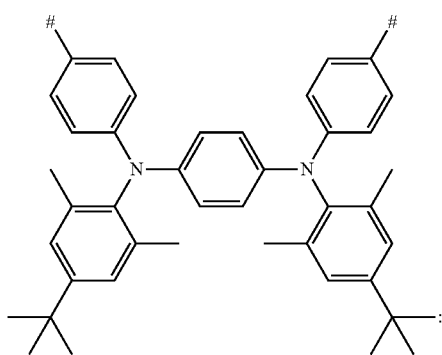

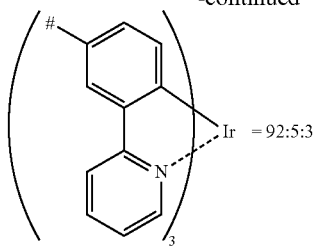

Properties of EL Light Emission of Polymer Compound 6

An EL device was produced by the same method as that in Example 1 except that Polymer Compound 6 was used instead of Polymer Compound 1 in Example 1, and a solution of poly(ethylenedioxythiophene)/polystyrene sulfonate made by H. C. Starck GmbH (trade name: CLEVIOS P AI4083) was used instead of that made by Bayer AG (trade name: Baytron P). By applying voltage to the obtained EL device, white EL light emission having a peak at 470 nm was obtained. This EL device showed luminescence of 1000 cd/m² at approximately 11.6 V. The maximum luminous efficiency was 0.24 cd/A.

Industrial Applicability

The polymer compound and the like according to the present invention are particularly useful for production of devices such as light-emitting devices (for example, electroluminescent devices) and photoelectric devices.

The invention claimed is:

1. A polymer compound comprising:
a residue of a metal complex represented by the following formula (1c):

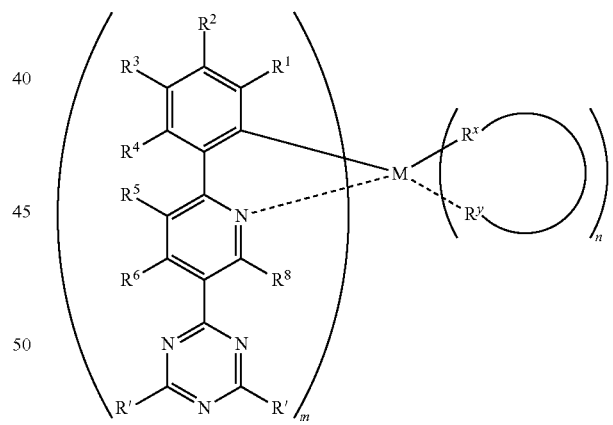

wherein M represents a metal atom of ruthenium, rhodium, palladium, osmium, iridium, or platinum; $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group, or $R^1$ and $R^2$, $R^2$ and $R^3$, $R^3$ and $R^4$, $R^4$ and $R^5$, or $R^5$ and $R^6$ may be bonded to form a ring; m is an integer of 1 to 3 and n is 0; in the case where each of $R^1$, $R^2$, $R^3$, $R^4$, $R^5$, $R^6$, and $R^8$ is plural, a plurality of $R^4$ may be the same or different, a plurality of $R^2$ may be the same or different, a plurality of $R^3$ may be the same or different, a plurality of $R^4$ may be the same or different, a plurality of $R^5$ may be the same or different, a plurality of $R^6$ may be the same or different, and a plurality of $R^8$ may be the same or different; R' represents a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group; a plurality of R' may be the same or different;; and a divalent group represented by the following formula (3-1), (3-2), (3-3), (3-4), or (3-5):

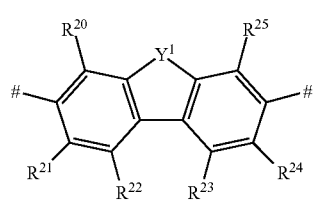
(3-1)

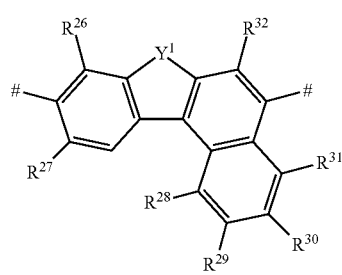
(3-2)

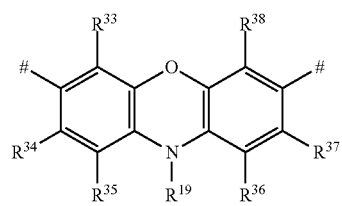
(3-3)

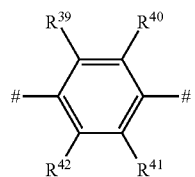
(3-4)

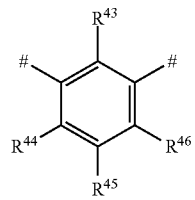
(3-5)

wherein # represents a bond; $Y^1$ represents —C($R^9$)($R^{10}$)—, —O—C($R^{17}$)($R^{18}$)—, —O—, —S—, —B($R^{11}$)—, —Si($R^{12}$)($R^{13}$)—, —P($R^{14}$)—, —P($R^{15}$)(=O)—, or —N($R^{16}$)—; $R^9$, $R^{10}$, $R^{11}$, $R^{12}$, $R^{13}$, $R^{14}$, $R^{15}$, $R^{16}$ $R^{17}$, $R^{18}$, and $R^{19}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; $R^{20}$ $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group.

2. The polymer compound according to claim 1, wherein the $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group; or $R^3$ and $R^4$, or $R^5$ and $R^6$ may be bonded to form a ring.

3. The polymer compound according to claim 1, wherein the M is a platinum atom or an iridium atom.

4. The polymer compound according to claim 1, wherein the residue of a metal complex represented by the formula (1c) is a monovalent to trivalent group.

5. The polymer compound according to claim 1, comprising a residue of a metal complex represented by the formula (1c) and a group represented by the formula (3-1).

6. The polymer compound according to claim 1, further comprising a group represented by the following formula (4):

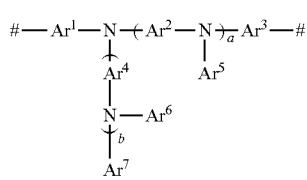

(4)

wherein $Ar^1$, $Ar^2$, $Ar^3$, and $Ar^4$ each independently represent an arylene group or a divalent heterocyclic group; $Ar^5$, $Ar^6$, and $Ar^7$ each independently represent an aryl group or a monovalent heterocyclic group; $Ar^1$, $Ar^2$, $Ar^3$, $Ar^4$, $Ar^5$, $Ar^6$, and $Ar^7$ may have a substituent; a and b each independently represent 0 or 1, and $0 \leq a + b \leq 1$; # represents a bond.

7. A composition comprising a polymer compound according to claim 1.

8. The composition according to claim 7, further comprising a solvent or a dispersion medium.

9. A film comprising a polymer compound according to claim 1.

10. A device comprising a polymer compound according to claim 1.

11. The device according to claim 10, wherein the device is a light-emitting device.

12. A surface light source comprising the device according to claim 11.

13. A light comprising the device according to claim 11.

14. A method for producing a polymer compound comprising: a residue of a metal complex represented by a formula (1c):

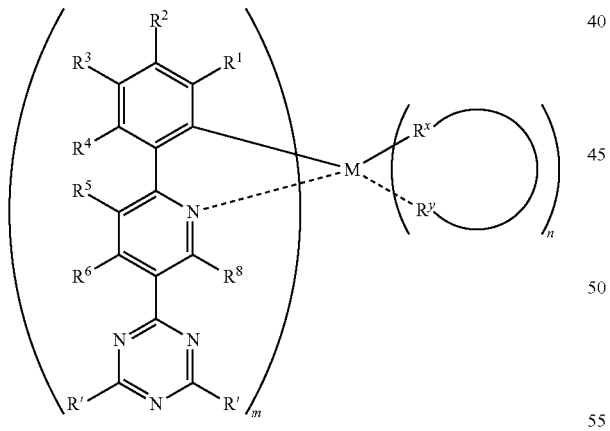

(1c)

wherein M represents a metal atom of ruthenium, rhodium, palladium, osmium, iridium, or platinum; $R^1$, $R^2$, $R^3$, $R^4$, $R^5$, $R^6$, and $R^8$ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group, or $R^1$ and $R^2$, $R^2$ and $R^3$, $R^3$ and $R^4$, $R^4$ and $R^5$, or $R^5$ and $R^6$ may be bonded to form a ring; m is an integer of 1 to 3 and n is 0; in the case where each of $R^1$, $R^2$, $R^3$, $R^4$, $R^5$, $R^6$, and $R^8$ is plural, a plurality of $R^1$ may be the same or different, a plurality of $R^2$ may be the same or different, a plurality of $R^3$ may be the same or different, a plurality of $R^4$ may be the same or different, a plurality of $R^5$ may be the same or different, a plurality of $R^6$ may be the same or different, and a plurality of $R^8$ may be the same or different; R' represents a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group, or a cyano group; a plurality of R' may be the same or different; and a divalent group represented by a formula (3-1), (3-2), (3-3), (3-4), or (3-5):

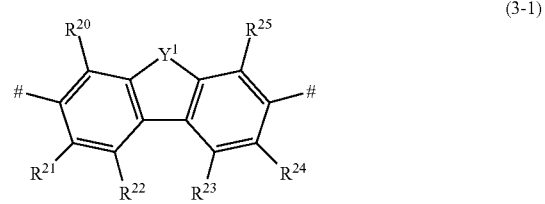

(3-1)

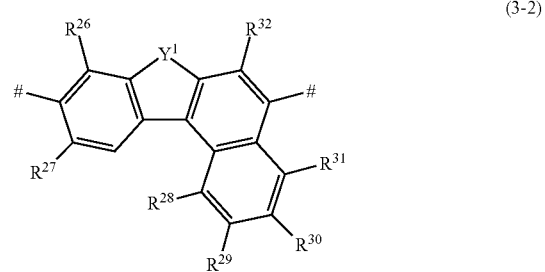

(3-2)

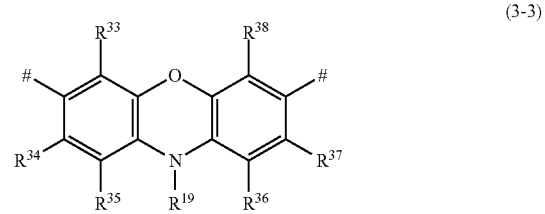

(3-3)

(3-4)

-continued (3-5)

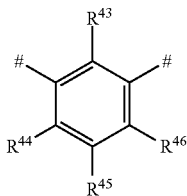

wherein # represents a bond; Y¹ represents —C(R⁹)(R¹⁰)—, —O—C(R¹⁷)(R¹⁸)—, —O—, —S—, —B(R¹¹)—, —Si(R¹²)(R¹³)—, —P(R¹⁴)—, —P(R¹⁵)(=O)—, or —N(R¹⁶)—; R⁹, R¹⁰, R¹¹, R¹², R¹³, R¹⁴, R¹⁵, R¹⁶, R¹⁷, R¹⁸, and R¹⁹ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; ; R²⁰, R²¹, R²², R²³, R²⁴, R²⁵, R²⁶, R²⁷, R²⁸, R²⁹, R³⁰, R³¹, R³², R³³, R³⁴, R³⁵, R³⁶, R³⁷, R³⁸, R³⁹, R⁴⁰, R⁴¹, R⁴², R⁴³, R⁴⁴, R⁴⁵, and R⁴⁶ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group;

the method comprising reacting a metal complex represented by the following formula (5):

(5)

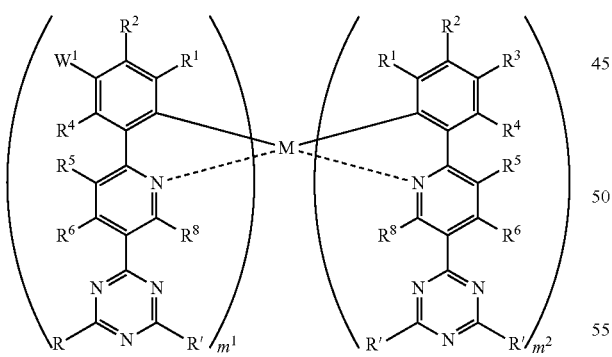

wherein W¹ represents a polymerization reactive group; m¹ is an integer of 1 to 3, and m² is an integer of 0 to 2; M represents a metal atom of ruthenium, rhodium, palladium, osmium, iridium, or platinum; R¹, R², R³, R⁴, R⁵, R⁶, and R⁸ each independently represent a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an acyl group, an acyloxy group, an amide group, an acid imide group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, or R¹ and R², R² and R³, R³ and R⁴, R⁴ and R⁵, or R⁵ and R⁶ may be bonded to form a ring; in the case where each of R¹, R², R³, R⁴, R⁵, R⁶, and R⁸ is plural, a plurality of R¹ may be the same or different, a plurality of R² may be the same or different, a plurality of R³ may be the same or different, a plurality of R⁴ may be the same or different, a plurality of R⁵ may be the same or different, a plurality of R⁶ may be the same or different, and a plurality of R⁸ may be the same or different; with a compound represented by the following formula (6-1), (6-2), (6-3), (6-4), or (6-5):

(6-1)

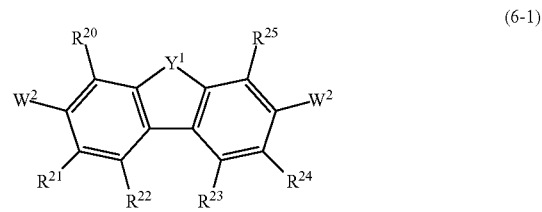

(6-2)

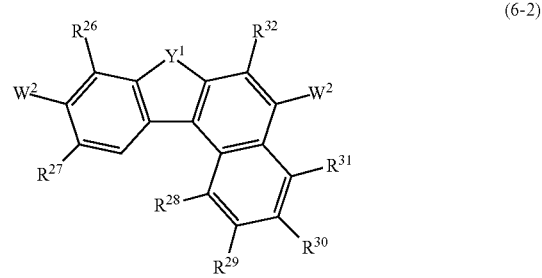

(6-3)

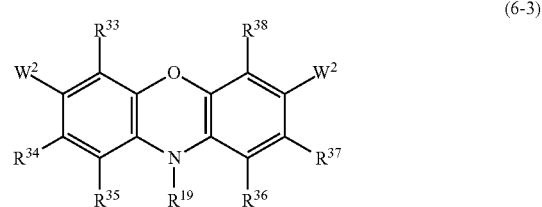

(6-4)

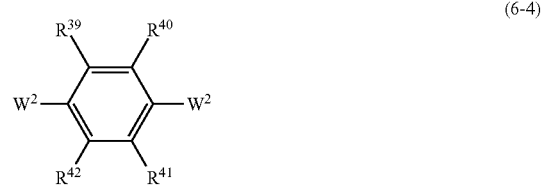

(6-5)

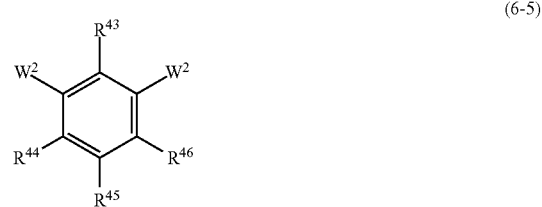

wherein W² represents a polymerization reactive group; a plurality of W² may be the same or different; Y¹ represents —C(R⁹)(R¹⁰)—, —O—C(R¹⁷)(R¹⁸)—, —O—, —S—, —B(R¹¹)—, —Si(R¹²)(R¹³)—, —P(R¹⁴)—, —P($R^{15}$)(=O)—, or —N($R^{16}$)—; $R^9$, $R^{10}$, $R^{11}$, $R^{12}$, $R^{13}$, $R^{14}$, $R^{15}$, $R^{16}$, $R^{17}$, $R^{18}$, and $R^{19}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group, or a halogen atom; $R^{20}$, $R^{21}$, $R^{22}$, $R^{23}$, $R^{24}$, $R^{25}$, $R^{26}$, $R^{27}$, $R^{28}$, R29, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ each independently represent a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a monovalent heterocyclic group, a carboxyl group, a substituted carboxyl group, or a cyano group.

15. The method according to claim 14, wherein the $W^1$ and $W^2$ are each —B(OH)$_2$, a boric acid ester residue, —MgX (X represents a halogen atom), a stannyl group, or a halogen atom.

\* \* \* \* \*